(12) United States Patent
Picker et al.

(10) Patent No.: US 10,532,099 B2
(45) Date of Patent: Jan. 14, 2020

(54) CYTOMEGALOVIRUS VECTORS ELICITING T CELLS RESTRICTED BY MAJOR HISTOCOMPATIBILITY COMPLEX E MOLECULES

(71) Applicant: Oregon Health & Science University, Portland, OR (US)

(72) Inventors: Louis Picker, Portland, OR (US); Scott Hansen, Portland, OR (US); Klaus Frueh, Portland, OR (US); Daniel Malouli, Hillsboro, OR (US); Jay Nelson, Portland, OR (US); Jonah Sacha, Beaverton, OR (US); Meaghan Hancock, Aloha, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 15/786,847

(22) Filed: Oct. 18, 2017

(65) Prior Publication Data
US 2018/0133321 A1    May 17, 2018

Related U.S. Application Data

(60) Provisional application No. 62/409,840, filed on Oct. 18, 2016.

(51) Int. Cl.
| | |
|---|---|
| A61K 45/00 | (2006.01) |
| A61K 39/00 | (2006.01) |
| A61K 39/12 | (2006.01) |
| C12N 7/04 | (2006.01) |
| C12N 15/86 | (2006.01) |
| C12N 15/113 | (2010.01) |

(52) U.S. Cl.
CPC .......... A61K 45/00 (2013.01); A61K 39/0011 (2013.01); A61K 39/12 (2013.01); C12N 7/045 (2013.01); C12N 15/113 (2013.01); C12N 15/86 (2013.01); A61K 2039/5256 (2013.01); A61K 2039/55 (2013.01); A61K 2039/572 (2013.01); C12N 2310/141 (2013.01); C12N 2710/16134 (2013.01); C12N 2710/16143 (2013.01); C12N 2740/15034 (2013.01)

(58) Field of Classification Search
CPC .... C07K 14/005; C12N 15/86; C12N 5/0636; C12N 15/64; C12N 15/67; C12N 2710/16011; C12N 2710/16034; C12N 2710/16041; C12N 2710/16061; C12N 2710/16111; C12N 2710/16134; C12N 2710/16141; C12N 15/113; C12N 7/045; C12N 2710/16143; C12N 2740/15034; C12N 2310/141; C12N 2710/16171; A61K 39/12; A61K 45/00; A61K 2039/545; A61K 2039/53; A61K 48/0008; A61K 39/21; A61K 39/0011; A61K 2039/5256; A61K 2039/55; A61K 2039/572; Y02A 50/412; A61P 31/14
See application file for complete search history.

(56) References Cited

U.S. PATENT DOCUMENTS

| | | | |
|---|---|---|---|
| 5,168,062 | A | 12/1992 | Stinski |
| 5,273,876 | A | 12/1993 | Hock et al. |
| 5,385,839 | A | 1/1995 | Stinski |
| 5,720,957 | A | 2/1998 | Jones et al. |
| 5,830,745 | A | 11/1998 | Hock et al. |
| 5,833,993 | A | 11/1998 | Wardley et al. |
| 6,033,671 | A | 3/2000 | Frueh et al. |
| 7,892,822 | B1 | 2/2011 | Koszinowski et al. |
| 9,249,427 | B2 | 2/2016 | Picker et al. |
| 9,541,553 | B2 | 1/2017 | Picker et al. |
| 9,783,823 | B2 | 10/2017 | Picker et al. |
| 9,862,972 | B2 | 1/2018 | Picker et al. |
| 9,982,241 | B2 | 5/2018 | Picker et al. |
| 10,101,329 | B2 | 10/2018 | Picker et al. |
| 10,167,321 | B2 | 1/2019 | Carfi et al. |
| 2002/0176870 | A1 | 11/2002 | Schall et al. |
| 2003/0118568 | A1 | 6/2003 | Crew |
| 2003/0138454 | A1 | 7/2003 | Hill et al. |
| 2004/0086489 | A1 | 5/2004 | Schall et al. |
| 2004/0110188 | A1 | 6/2004 | Hahn et al. |
| 2004/0248300 | A1 | 12/2004 | Preston |
| 2005/0064394 | A1 | 3/2005 | Liu et al. |
| 2005/0118192 | A1 | 6/2005 | Boursnell et al. |

(Continued)

FOREIGN PATENT DOCUMENTS

| | | |
|---|---|---|
| EP | 0521427 A1 | 1/1993 |
| WO | WO-8810311 A1 | 12/1988 |

(Continued)

OTHER PUBLICATIONS

Geisler A, Fechner H. MicroRNA-regulated viral vectors for gene therapy. World J Exp Med. May 20, 2016;6(2):37-54. doi: 10.5493/wjem.v6.i2.37. eCollection May 20, 2016.*

(Continued)

*Primary Examiner* — Rachel B Gill

(74) *Attorney, Agent, or Firm* — Sterne, Kessler, Goldstein & Fox P.L.L.C.

(57) ABSTRACT

Disclosed are CMV vectors that lack active UL128, UL130, UL146 and UL147 proteins that may also comprise one or more microRNA regulatory elements (MRE) that restrict expression of the CMV. Immunization with the disclosed CMV vectors allow selection of different CD8+ T cell responses—CD8+ T cells restricted by MHC-Ia, MHC-II, or by MHC-E.

67 Claims, 21 Drawing Sheets

Specification includes a Sequence Listing.

(56) References Cited

U.S. PATENT DOCUMENTS

| | | |
|---|---|---|
| 2006/0019369 A1 | 1/2006 | Hahn |
| 2008/0071037 A1 | 3/2008 | Carr et al. |
| 2008/0199493 A1 | 8/2008 | Picker et al. |
| 2009/0148435 A1 | 6/2009 | Lebreton et al. |
| 2009/0148447 A1 | 6/2009 | Ledbetter et al. |
| 2009/0148477 A1 | 6/2009 | Bruder et al. |
| 2009/0203144 A1 | 8/2009 | Beaton et al. |
| 2009/0297555 A1 | 12/2009 | Kemble et al. |
| 2010/0142823 A1 | 6/2010 | Wang et al. |
| 2013/0089559 A1 | 4/2013 | Grawunder et al. |
| 2013/0136768 A1* | 5/2013 | Picker ............ A61K 39/12 424/199.1 |
| 2013/0142823 A1 | 6/2013 | Picker et al. |
| 2013/0156808 A1 | 6/2013 | Jonjic |
| 2013/0202638 A1 | 8/2013 | Thirion et al. |
| 2014/0141038 A1* | 5/2014 | Picker ............ C12N 15/86 424/199.1 |
| 2016/0010112 A1 | 1/2016 | Picker et al. |
| 2016/0114027 A1 | 4/2016 | Picker et al. |
| 2016/0354461 A1 | 12/2016 | Picker et al. |
| 2017/0143809 A1 | 5/2017 | Nelson et al. |
| 2017/0350887 A1 | 12/2017 | Picker et al. |
| 2018/0016599 A1* | 1/2018 | Evans ............ A61K 39/04 |
| 2018/0087069 A1 | 3/2018 | Picker et al. |
| 2018/0282378 A1 | 10/2018 | Frueh et al. |
| 2018/0298404 A1 | 10/2018 | Frueh et al. |

FOREIGN PATENT DOCUMENTS

| | | |
|---|---|---|
| WO | WO-9604383 A1 | 2/1996 |
| WO | WO-9631241 A1 | 10/1996 |
| WO | WO-9906582 A1 | 2/1999 |
| WO | WO-9907869 A1 | 2/1999 |
| WO | WO-02062296 A2 | 8/2002 |
| WO | WO-03093455 A2 | 11/2003 |
| WO | WO-2006031264 A2 | 3/2006 |
| WO | WO-2006125983 A1 | 11/2006 |
| WO | WO-2010101663 A2 | 9/2010 |
| WO | WO-2011093858 A1 | 8/2011 |
| WO | WO-2011119920 A2 | 9/2011 |
| WO | WO-2011138040 A2 | 11/2011 |
| WO | WO-2011143650 A2 | 11/2011 |
| WO | WO-2011143653 A2 | 11/2011 |
| WO | WO-2012170765 A2 | 12/2012 |
| WO | WO-2014138209 A1 | 9/2014 |
| WO | WO-2016011293 A1 | 1/2016 |
| WO | WO-2016130693 A1 | 8/2016 |
| WO | WO-2017087921 A1 | 5/2017 |
| WO | WO-2018005559 A1 | 1/2018 |

OTHER PUBLICATIONS

O'Connor CM, Vanicek J, Murphy EA. Host microRNA regulation of human cytomegalovirus immediate early protein translation promotes viral latency. J Virol. May 2014;88(10):5524-32. doi: 10.1128/JVI.00481-14. Epub Mar 5, 2014. (Year: 2014).*
Geisler A, Fechner H. MicroRNA-regulated viral vectors for gene therapy. World J Exp Med. May 20, 2016;6(2):37-54. doi: 10.5493/wjem.v6.i2.37. eCollection May 20, 2016 (Year: 2016).*
Guo XZ, et. al. Mol Ther Methods Clin Dev. Jan. 27, 2016;3:15054. eCollection 2016. (Year: 2016).*
Hansen SG, et. al. Science. Feb. 12, 2016;351(6274):714-20. Epub Jan. 21, 2016. Supplementary Info. (Year: 2016).*
Altschul, S.F. and Gish W., "Local Alignment Statistics," Methods in Enzymology 266:460-480, Academic Press, United States (1996).
Altschul, S.F., et al., "Basic Local Alignment Search Tool," Journal of Molecular Biology 215(3):403-410, Elsevier, England (Oct. 1990).
Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).
Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).
Basta, S., et al., "Inhibitory Effects of Cytomegalovirus Proteins Us2 and Us11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).
Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).
Borst, E and Messerle, M, "Development of a Cytomegalovirus Vector for Somatic Gene Therapy," Bone Marrow Transplant 25 Suppl 2:S80-S82, Nature Publishing Group (May 2000).
Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).
Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).
Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).
Brondke, H. "Human Herpesvirus 5, Towne Strain," US3 (NCBI GenBank Ace. No. AAS49002), Dep. Apr. 8, 2004.
Brondke, H. "Human Herpesvirus 5, Towne Strain," US6 (NCBI GenBank Ace. No. AAS49004), Dep. Apr. 8, 2004.
Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).
Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.
Cantrell, S.R and Bresnahan, W.A, "Human Cytomegalovirus (Hcmv) UL82 Gene Product (pp71) Relieves hDaxx-mediated Repression of Hcmv Replication," Journal of Virology 80(12):6188-6191, American Society for Microbiology, United States (Jun. 2006).
Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).
Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).
Chau, N.H., et al., "Transcriptional Regulation of the Human Cytomegalovirus Us11 Early Gene," Journal of Virology 73(2):863-870, American Society for Microbiology, United States (Feb. 1999).
Corpet, F, "Multiple Sequence Alignment With Hierarchical Clustering," Nucleic Acids Research 16(22):10881-10890, Oxford University Press, England (Nov. 1988).
Davison, A.J and Stow, N.D, "New Genes From Old: Redeployment of DUTPase by Herpesviruses," Journal of Virology 79(20):12880-12892, American Society for Microbiology, United States (Oct. 2005).
Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).
Dudek, T and Knipe, D.M, "Replication-defective Viruses as Vaccines and Vaccine Vectors," Virology 344(1):230-239, Academic Press, United States (Jan. 2006).

(56) References Cited

OTHER PUBLICATIONS

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).
European Search Report for EP Application No. EP16200334,The Hague, dated May 18, 2017.
European Search Report for EP Application No. EP17197412, Munich, Germany, dated Apr. 23, 2018.
Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).
Final Office Action dated Mar. 14, 2016, in U.S. Appl. No. 14/179,152, inventors Picker, L., et al., filed Feb. 12, 2014, 16 pages.
Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).
Gill, R.B., et al., "Coding Potential of Ul/b' From the Initial Source of Rhesus Cytomegalovirus Strain 68-1," Virology 447(1-2):208-212, Academic Press, United States (Dec. 2013).
Gish, W and States, D.J, "Identification of Protein Coding Regions by Database Similarity Search," Nature Genetics 3(3):266-272, Nature Publishing Group, United States (Mar. 1993).
Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).
Goodrum, F., et al., "Human Cytomegalovirus Persistence," Cellular Microbiology 14(5):644-655, Wiley-Blackwell, England (May 2012).
Gorman, S., et al., "Prior Infection with Murine Cytomegalovirus (Mcmv) Limits the Immunocontraceptive Effects of an MCMV Vector Expressing the Mouse Zona-Pellucida-3 Protein," Vaccine 26(31):3860-3869, Elsevier Science, Netherlands (Jul. 2008).
Grimwood, J., et al. "NCBI GenBank Direct Submission," Acc. No. AC146906, Sub. Nov. 5, 2003.
Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.
Hahn, G., et al., "Human Cytomegalovirus UL 131-128 Genes are Indispensible for Virus Growth in Endothelial Cells and Virus Transfer to Leukocytes," Journal of Virology, 78(18):10023-10033, American Society for Microbiology, United States (Sep. 2004).
Matthews, T.J., et al., "Prospects for Development of a Vaccine Against HTLV-III-Related Disorders," AIDS Research and Human Retroviruses 3(s1):197-206, Mary Ann Liebert, United States (1987).
Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002 ).
Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences," Computer Applications in the Biosciences,10(1):67-70, Oxford University Press, England (Feb. 1994).
Hancock, M.H., et al., "Rhesus Cytomegalovirus Encodes Seventeen Micrornas that are Differentially Expressed In Vitro and In Vivo," Virology 425(2):133-142, Academic Press, United States (Apr. 2012).
Hansen, S.G., et al., "Broadly Targeted Cd8$^+$ T Cell Responses Restricted by Major Histocompatibility Complex E," Science 351(6274):714-720, American Association for the Advancement of Science, United States (Feb. 2016).
Hansen, S.G., et al., "Complete Sequence and Genomic Analysis of Rhesus Cytomegalovirus," Journal of Virology 77(12):6620-6636, American Society for Microbiology, United States (Jun. 2003).

Hansen, S.G., et al., "Cytomegalovirus Vectors Violate CD8+ T Cell Epitope Recognition Paradigms," Science 340(6135):1237874, American Association for the Advancement of Science, United States (May 2013).
Hansen, S.G., et al., "Effector Memory T Cell Responses are Associated With Protection of Rhesus Monkeys From Mucosal Simian Immunodeficiency Virus Challenge," Nature Medicine 15(3):293-299, Nature Publishing Company, United States (Mar. 2009).
Hansen, S.G., et al., "Evasion of Cd8+ T Cells Is Critical for Superinfection by Cytomegalovirus," Science 328(5974):102-106, American Association for the Advancement of Science, United States (Apr. 2010).
Hansen, S.G., et al., "Immune Clearance of Highly Pathogenic SIV Infection," Nature 502(7469):100-104, Nature Publishing Group, United Kingdom (Oct. 2013).
Hansen, S.G., et al., "Profound Early Control of Highly Pathogenic SIV by an Effector Memory T-cell Vaccine," Nature 473(7348):523-527, Nature Publishing Group, England (May 2011).
Higgins, D.G and Sharp, P.M, "CLUSTAL: A Package for Performing Multiple Sequence Alignment on a Microcomputer," Gene 73(1):237-244, Elsevier/North-Holland, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Huang, X., et al., "Parallelization of a Local Similarity Algorithm," Computer Applications in the Biosciences 8(2):155-165, Oxford University Press, England (Apr. 1992).
International Preliminary Report on Patentability for International Application No. PCT/US2016/017373, The International Bureau of WIPO, Geneva, Switzerland, dated Aug. 15, 2017, 8 pages.
International Search Report and Written opinion for International Application No. PCT/US2015/040807, European Patent Office, HV Rijswijk, dated Oct. 28, 2015, 6 pages.
International Search Report and Written opinion for International Application No. PCT/US2016/017373, Korean Intellectual Property Office, Republic of Korea, dated May 23, 2016.
International Search Report for International Application No. PCT/US2011/036657, Korean Intellectual Property Office, Republic of Korea, dated Mar. 28, 2012.
International Search Report for International Application No. PCT/US2012/041475, Korean Intellectual Property Office, Republic of Korea, dated Dec. 14, 2012.
James, SH and Prichard, M.N., "The Genetic Basis of Human Cytomegalovirus Resistance and Current Trends in Antiviral Resistance Analysis, " Infectious Disorders Drug Targets, 11(5):504-513, Bentham Science Publishers, United Arab Emirates (Oct. 2011).
Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).
Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).
Kaech, S.M., et al., "Effector and Memory T-cell Differentiation: Implications for Vaccine Development," Nature Reviews. Immunology 2(4):251-262, Nature Pub. Group, England (2002).
Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).
Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).
Karlin, S, and Altschul, S.F., "Applications and Statistics for Multiple High-scoring Segments in Molecular Sequences," Proceedings

(56) References Cited

OTHER PUBLICATIONS of the National Academy of Sciences USA 90(12):5873-5877, National Academy of Sciences, United States (Jun. 1993).
Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).
Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).
Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).
Mahmood, K., et al., "Human Cytomegalovirus Plasmid-based Amplicon Vector System for Gene Therapy," Genetic vaccines and therapy 3(1):1, BioMed Central, England (Jan. 2005).
Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).
Marshall, K.R., et al., "Activity and Intracellular Localization of the Human Cytomegalovirus Protein PP71," The Journal of general virology 83(Pt 7):1601-1612, Microbiology Society, England (Jul. 2002).
Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).
McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).
McGregor, A., et al., "Molecular, Biological, and in Vivo Characterization of the Guinea Pig Cytomegalovirus (CMV) Homologs of the Human Cmv Matrix Proteins pp71 (UL82) and pp65 (UL83)," Journal of virology 78(18):9872-9889, American Society for Microbiology, United States (Sep. 2004).
Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).
Mohr, C.A., et al., "A Spread-deficient Cytomegalovirus for Assessment of First-target Cells in Vaccination," Journal of virology 84(15):7730-7742, American Society for Microbiology, United States (Aug. 2010 ).
Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).
Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).
Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).
Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).
Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).

Myers, E.W., and Miller, W., "Optimal Alignment in Linear Space," Computer Applications in the Biosciences 4(1):1-13, Oxford University Press, England (Mar. 1988).
Kim, S., et al., "Human Cytomegalovirus MicroRNA miR-US4-1 Inhibits CD8(+) T cell Responses by Targeting the Aminopeptidase ERAP1," Nature Immunology 12(10):984-991, Nature America Inc, United States (Sep. 2011).
Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).
Non-final Office Action dated Jan. 9, 2015, in U.S. Appl. No. 14/179,152, inventors Picker, L., et al., filed Feb. 12, 2014, 20 pages.
Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).
Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).
Oxford, K.L., et al., "Protein Coding Content of the UL)b' Region of Wild-type Rhesus Cytomegalovirus," Virology, 373(1):181-183, Academic Press, United States (Mar. 2008).
Oxford, K.L., et al., "Protein Coding Content of the ULb' Region of Wild-Type Rhesus Cytomegalovirus," Virology 373(1):181-188, Academic Press, United States (Mar. 2008).
Pearce, E.L., et al., "Functional Characterization of MHC Class II-Restricted CD8+CD4− and CD8−CD4− T cell Responses to Infection in CD4−/− Mice," Journal of Immunology 173(4):2494-2499, American Association of Immunologists, United States (Aug. 2004).
Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Hanley, P.J., et al., "Controlling cytomegalovirus: helping the immune system take the lead," Viruses, 6(6):2242-2258, MDPI, Switzerland (May 2014).
Heineman, T.C., "Chapter 71: Human cytomegalovirus vaccines." In: Arvin, A, Campadelli-Fiume, G, Mocarski, E, et al., eds. Human Herpesviruses: Biology, Therapy, and Immunoprophylaxis, Cambridge: Cambridge University Press, 2007.
Picker, L.J., et al., "New paradigms for HIV/AIDS vaccine development," Annual Review of Medicine 63:95-111, Annual Reviews, United States (Feb. 2012).
Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).
International Preliminary Report on Patentability for International Application No. PCT/US2015/040807 , The International Bureau of WIPO, Geneva, Switzerland, dated Jan. 17, 2017, 8 pages.
Joosten, S.A., et al., "Characteristics of HLA-E Restricted T-Cell Responses and Their Role in Infectious Diseases, " Journal of Immunology Research, 2016:2695396, Hindawi Publishing Corporation, Egypt (Sep. 2016).
Lauron, E.J., et al., "Human Cytomegalovirus Infection of Langerhans-Type Dendritic Cells Does Not Require the Presence of the gH/gL/UL128-131A Complex and Is Blocked after Nuclear Deposition of Viral Genomes in Immature Cells, " Journal of Virology, 88(1):403-416, American Society for Microbiology, United States (Jan. 2014).
Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).

(56) References Cited

OTHER PUBLICATIONS

Powers, C and Fruh, K, "Rhesus CMV: An Emerging Animal Model for Human CMV," Medical Microbiology and Immunology 197(2):109-115, Springer-Verlag, Germany (Jun. 2008).
Smith, I.L., et al., "High-level resistance of cytomegalovirus to ganciclovir is associated with alterations in both the UL97 and DNA polymerase genes, " Journal of Infectious Diseases, 176(1): 69-77, Oxford University Press, United States (Jul. 1997). Erratum in: Journal of Infectious Diseases, 177(4):1140-1141 (Apr. 1998).
Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).
Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).
Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).
Sambrook, J., et al., "Molecular Cloning: A Laboratory Manual," Third Edition, Cold Spring Harbor Laboratory Press, United States (1989).
Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).
Schuessler, A., et al., "Charge Cluster-to-Alanine Scanning of UL 12B for Fine Tuning of the Endothelial Cell Tropism of Human Cytomegalovirus," Journal of Virology, 82(22):11239-11246, American Society for Microbiology, United States (Nov. 2008).
Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).
Smith, T.F. and Waterman, M.S., "Comparison of Biosequences," Advances in Applied Mathematics 2(4):482-489, Academic Press, Inc., United States (Dec. 1981).
European Search Report for EP Application No. EP11008462, Munich, Germany, dated Jul. 26, 2012.
GenBank Report, Accession No. NP_057850, (published Aug. 1, 2000).
Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).
Nicholson J.P., et al., "Properties of Virion Transactivator Proteins encoded by Primate Cytomegaloviruses," Journal of Virology, 6:65, BioMed Central, England (May 2009).
Non final Office Action dated Aug. 4, 2015, in U.S. Appl. No. 11/597,457, Picker, L.J. et al., filed Apr. 28, 2008.
Oxxon Therapeutics Licenses Rights to Xenova's DISC-HSV and DISC-GM-CSF Vector Technolgies, BusinessWire, Jan. 13, 2005.
Tessmer, M.S., et al., "Salivary Gland NK Cells Are Phenotypically and Functionally Unique," PLoS Pathogens 7(1):e1001254, Public Library of Science, United States (Jan. 2011).
Ulmer, J.B., et al., "Heterologous Protection against Influenza by injection of DNA Encoding a Viral Protein," Science 259(5102):1745-1749, American Association for the Advancement of Science, United States (Mar. 1993).
Ulmer, J.B, "Tuberculosis DNA Vaccines," Scandinavian Journal of Infectious Diseases 33(4):246-248, Informa Healthcare, England (2001).
Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).
Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).
Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).
Wu, F., et al., "Role of Specific MicroRNAs for Endothelial Function and Angiogenesis," Biochemical and Biophysical Research Communications 386(4):549-553, Elsevier, United States (Sep. 2009).
Written Opinion for International Application PCT/US2014/020690, filed Mar. 5, 2014, International Search Authority, Daejon, Korea, dated Jul. 17, 2014, 6 pages.
Cranage, M., et a., "Carriers for the delivery of a vaccine against respiratory syncytial virus," Expert Opinion on Biological Therapy 5(7): 939-952, Taylor & Francis, England (2005).
Antonis A.F., et al., "Vaccination with recombinant modified vaccinia virus Ankara expressing bovine respiratory syncytial virus (bRSV) proteins protects calves against RSV challenge," Vaccine 25(25):4818-4827, Elsevier, Netherlands (2007).
Kovarik, J., et al., "Induction of adult-like antibody, Th1, and CTL responses to measles hemagglutinin by early life murine immunization with an attenuated vaccinia derived NYVAC (K1L) viral vector," Virvology 285(1):12-20, Elsevier, Netherlands (2001).
Welter, J., et al., "Mucosal vaccination with recombinant poxvirus vaccine protects ferrets against symptomatic CDV infection," Vaccine 17(4):308-318, Elsevier, Netherlands (1999).
Guillaume, V., et al., "Nipah Virus: Vaccination and passive protection studies in a hamster model," Journal of Virology 78(2):834-840, The American Society for Microbiology, United States (2004).
Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).
Kenjiro, I., et al., "Long-term protective immunity to rinderpest in cattle following a single vaccination with a recombinant vaccinia virus expressing the virus haemagglutinin protein," Journal of General Virology 81(6):1439-1446, Microbiology Society, United Kingdom (2000).
International Search Report and Written opinion for International Application No. PCT/US2017/057106, Korean Intellectual Property Office, Daejeon, Korea , dated Jan. 24, 2018, 13 pages.
Bego, M., et al., "Characterization of an Antisense Transcript Spanning the Ul81-82 Locus of Human Cytomegalovirus, " Journal of Virology, 79(17):11022-11034, American Society for Microbiology, United States (Sep. 2005).
Dhuruvasan, K., et al., "Roles of Host and Viral MicroRNAs in Human Cytomegalovirus Biology, "Virus Research, 157(2):180-192, Elsevier Science, Netherlands (May 2011).
Khan, N., et al., "Identification of Cytomegalovirus-Specific Cytotoxic T Lymphocytes In Vitro Is Greatly Enhanced by the Use of Recombinant Virus Lacking the Us2 to Us11 Region or Modified Vaccinia Virus Ankara Expressing Individual Viral Genes, " Journal of Virology, 79(5):2869-2879, American Society for Microbiology, United States (Mar. 2005).
Noriega, V., et al., "Diverse Immune Evasion Strategies by Human Cytomegalovirus, " Immunologic Research, 54(1-3):140-151, Humana Press, United States (Dec. 2012).
Supplementary European Search Report mailed in E.P. Patent Application 16749813, Date of Completion of the Search Aug. 16, 2018, 6 pages.
Bentz, G.L., et al., "Human Cytomegalovirus (HCMV) Infection of endothelial Cells Promotes NaIve Monocyte Extravasation and transfer of Productive Virus to Enhance Hematogenous Dissemination of HCMV," Journal of Virology 80(23):11539-15555, American Society for Microbiology, United States (Dec. 2006).
Fruh, K and Picker, L, "CD8+ T cell programming by cytomegalovirus vectors: applications in prophylactic and therapeutic vaccination," Current Opinion in Immunology 47:52-56, Elsevier, England (Aug. 2017).

(56) References Cited

OTHER PUBLICATIONS

Gerna, G., et al., "Dendritic-cell Infection by Human Cytomegalovirus Is Restricted to Strains Carrying Functional Ul131-128 Genes and Mediates Efficient Viral Antigen Presentation to Cd8+ T Cells," Journal of General Virology 86(Pt 2):275-284, Microbiology Society, United Kingdom(Feb. 2005).

Grey, F., et al., "A Human Cytomegalovirus-encoded Microrna Regulates Expression of Multiple Viral Genes Involved in Replication," PLOS Pathogens 3(11):e163, Public Library of Science, United States (Nov. 2007).

Ojha, M and Barja, F, "Spatial and Cellular Localization of Calcium-dependent Protease (Cdp Ii) in Allomyces Arbuscula," Journal of Cell Science 116(Pt 6):1095-1105, Company of Biologists, England (Mar. 2003).

Bowman, J.J., et al., "Rhesus and Human Cytomegalovirus Glycoprotein L are Required for Infection and Cell-to-Cell Spread of Virus but Cannot Complement Each Other," Journal of Virology, 85(5): 2089-2099, American Society for Microbiology, United States (Mar. 2011).

Hobom, U., et al., "Fast Screening Procedures for Random Transposon Libraries of Cloned Herpesvirus Genomes: Mutational Analysis of Human Cytomegalovirus Envelope Glycoprotein Genes," Journal of Virology, 74(17):7720-7729, American Society for Microbiology (Sep. 2000).

Pietra, G., et al., "The Emerging Role of HLA-E-restricted CD8+ T Lymphocytes in the Adaptive Immune Response to Pathogens and Tumors," Journal of Biomedicine and Biotechnology 2010(9070921):1-8, Hindawi Publishing Corporation, United States (2010).

Powers, C., et al., "The US2-11 region of RhCMV is both necessary and sufficient to counteract CD8+ T-cell immunity during re-infection of rhesus macaques," 341 Annual International Herpesvirus Workshop, Jul. 25, 2009, Ithaca, New York.

Powers, C.J and Fruh, K, "Signal Peptide-dependent Inhibition of MHC Class I Heavy Chain Translation by Rhesus Cytomegalovirus," PLOS Pathogens 4(10):e1000150, Public Library of Science, United States (Oct. 2008).

Prod'Homme, V., et al., "Human Cytomegalovirus UL40 Signal peptide Regulates Cell Surface Expression of the NK Cell Ligands HLA-E and gpUL18," Journal of Immunology 188(6):2794-2804, American Society of Immunologist, United States (Mar. 2012).

Snyder, C.M., et al., "Cross-presentation of a Spread-defective MCMV is Sufficient to Prime the Majority of Virus-specific CD8+T Cells," PLoS One, 5(3):e9681, Public Library of Science, United States (Mar. 2010).

Written Opinion for International Application No. PCT/US2011/036657, Korean Intellectual Property Office, Republic of Korea, dated Mar. 28, 2012.

Retrieved from the Internet: (URL: http://www.microma.org/microma/getTargets.do?matureName=hsa-miR-142-3p&organism=9606), last accessed Oct. 6, 2015.

Smith, M.S., et al., "Roles of Phosphatidylinositol 3-Kinase and NF-B in Human Cytomegalovirus-Mediated Monocyte Diapedesis and Adhesion: Strategy for Viral Persistence," Virology 81(14):7683-7694, American Society for Microbiology, United States (Jul. 2007).

Kenneson, A and Cannon, M.J., "Review and Meta-analysis of the Epidemiology of Congenital Cytomegalovirus (CMV) Infection, " Reviews in Medical Virology 17(4):253-276, Wiley, England (Jul.-Aug. 2007).

European Communication, dated Jun. 15, 2018, in Application No. 16200334.7, 7 pages.

Jarvis, M.A and Nelson, J.A., "Mechanisms of Human Cytomegalovirus Persistence and Latency," Frontiers in Bioscience 7:d1575-d1582, Frontiers in Bioscience Publications, United States (Jun. 2002).

Wu., H.L., et al., "Cytomegalovirus vaccine vector 68-1 elicits universal, MHC-E-restricted CD8 T-cell responses against SIV," Journal of Medical Primatology 44(5):313, Wiley Online Library, United States (Oct. 2015).

\* cited by examiner

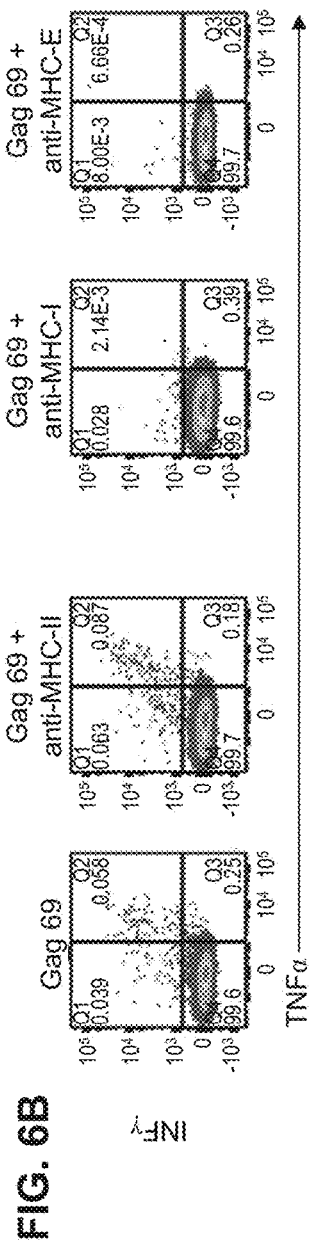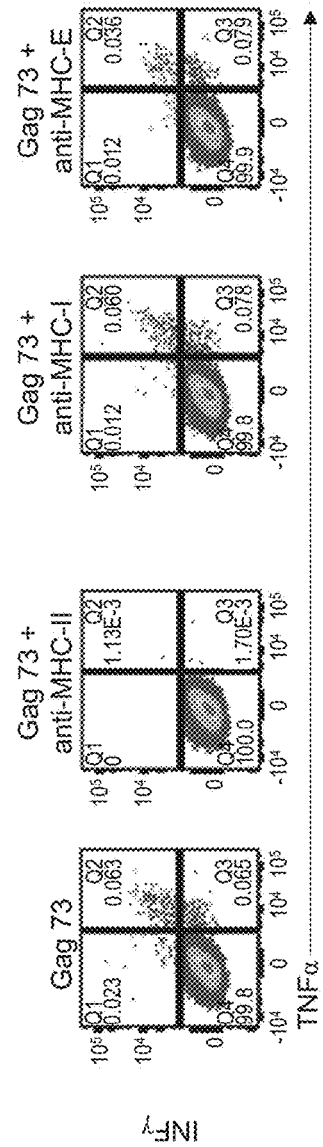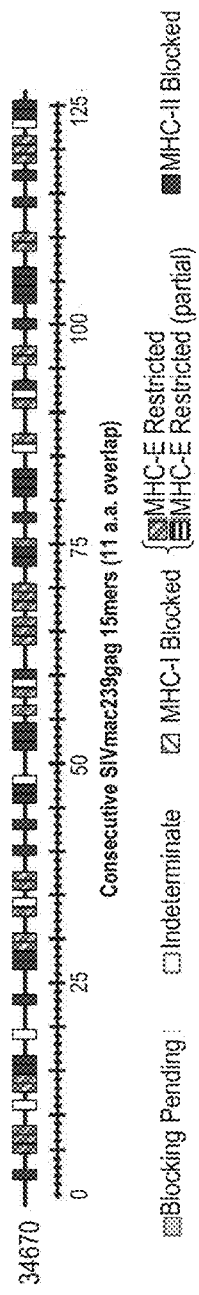
FIG. 6B
FIG. 6C

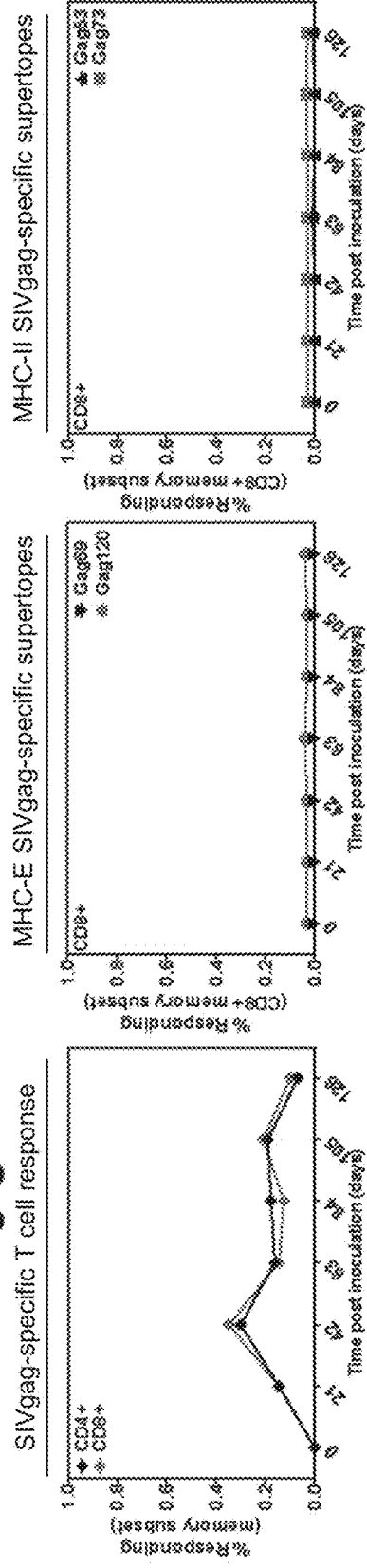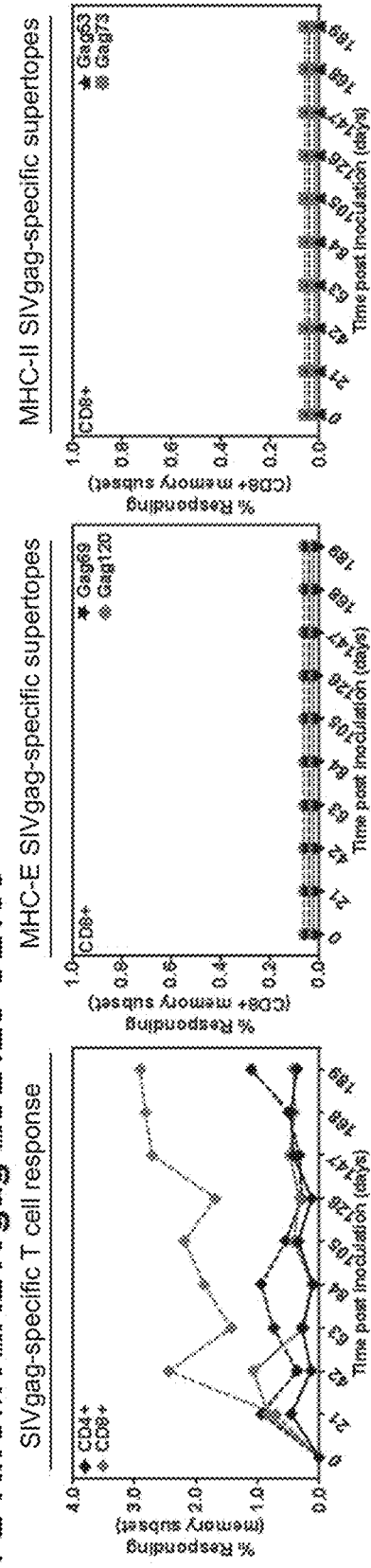
FIG. 8A
FIG. 8B

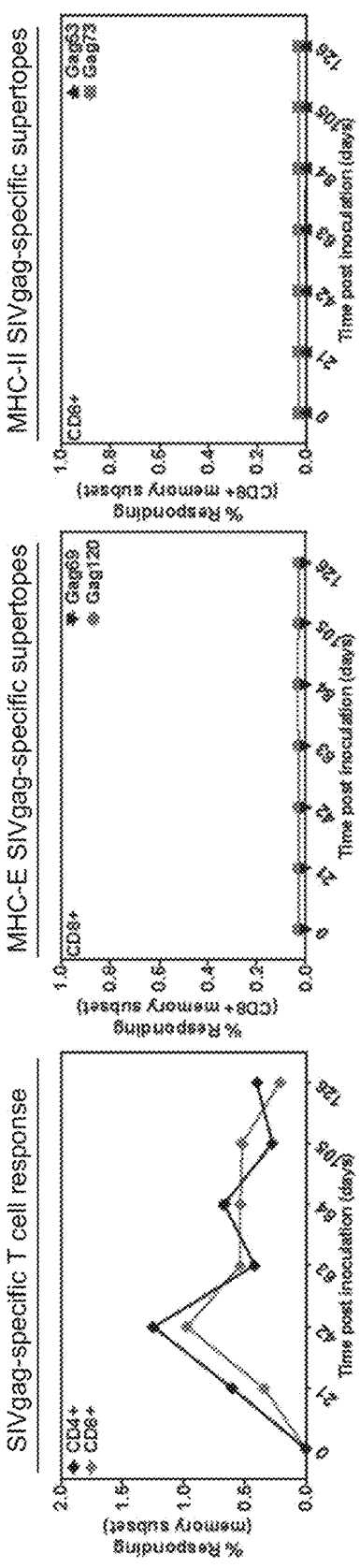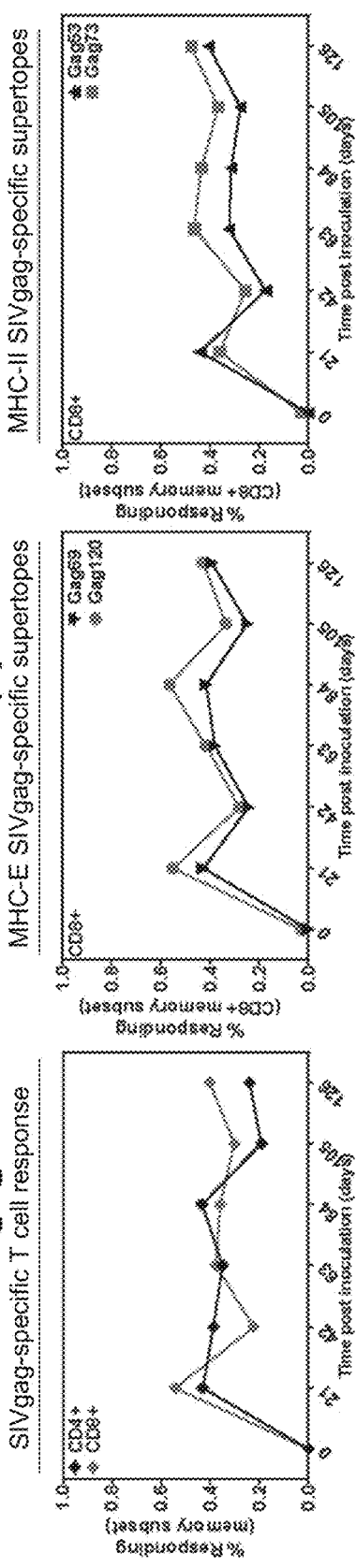
FIG. 8C
FIG. 8D

```
SEQUENCE LISTING

<160> NUMBER OF SEQ ID NOS: 4

<210> SEQ ID NO 1
<211> LENGTH: 22
<212> TYPE: RNA
<213> ORGANISM: Homo sapiens

<400> SEQUENCE: 1
ucguaccgug aguaauaaug cg                                                 22

<210> SEQ ID NO 2
<211> LENGTH: 22
<212> TYPE: DNA
<213> ORGANISM: Homo sapiens

<400> SEQUENCE: 2
cgcattatta ctcacggtac ga                                                 22

<210> SEQ ID NO 3
<211> LENGTH: 23
<212> TYPE: RNA
<213> ORGANISM: Homo sapiens

<400> SEQUENCE: 3
uguaguguuu ccuacuuuau gga                                                23

<210> SEQ ID NO 4
<211> LENGTH: 23
<212> TYPE: DNA
<213> ORGANISM: Homo sapiens

<400> SEQUENCE: 4
tccataaagt aggaaacact aca                                                23
```

CYTOMEGALOVIRUS VECTORS ELICITING T CELLS RESTRICTED BY MAJOR HISTOCOMPATIBILITY COMPLEX E MOLECULES

CROSS-REFERENCE TO RELATED APPLICATIONS

This application claims the benefit of priority from U.S. Provisional Application No. 62/409,840, filed on Oct. 18, 2016, the disclosure of which is incorporated herein by reference in its entirety.

ACKNOWLEDGEMENT OF GOVERNMENT SUPPORT

This disclosure was created with the support of the United States government under the terms of grant numbers P01 AI094417 and R01 AI117802, awarded by the National Institutes of Health. The United States government has certain rights in this disclosure.

TECHNICAL FIELD

The present invention relates to the use of cytomegalovirus (CMV) vectors in immunization, and more specifically, the generation of T cell responses characterized by MHC-E restriction. Particular embodiments relate to the generation of CD8+ T cells that are restricted by MHC-E.

REFERENCE TO A SEQUENCE LISTING SUBMITTED ELECTRONICALLY VIA EFS-WEB

The content of the electronically submitted sequence listing (Name: 3919.014PC01_ST25; Size: 1,063 bytes; and Date of Creation: Oct. 18, 2017) is herein incorporated by reference in its entirety.

SUMMARY

Genetically modified CMV vaccine vectors are disclosed herein. In embodiments of the genetically modified CMV vaccine vectors, the genetic modifications described herein change the epitope targeting and Major Histocompatibility Complex (MHC) restriction of CD8+ T cell responses elicited by the CMV vaccine vectors, including the ability to elicit CD8+ T cell responses that recognize unique epitopes restricted by cell surface MHC-II and MHC-E proteins. The MHC-II and MHC-E-restricted CD8+ T cell responses elicited by the CMV vaccine vectors described herein are unconventional and observed rarely in natural immune responses to infectious agents. In addition, the breadth and potency of the MHC-II and MHC-E-restricted CD8+ T cell responses elicited by the CMV vaccine vectors described herein are not observed with CMV vaccine vectors that are not genetically modified. In some embodiments, and without being bound by a particular theory, the inventors believe that MHC-E restricted CD8+ T cells may exploit a lack of pathogen and tumor immune evasion adaptations to MHC-E restricted immune responses, and that the genetically modified CMV vaccine vectors described herein, which may predominantly or exclusively elicit such responses, provide the potential for uniquely potent vaccines against targeted pathogens and tumors. Consistent with this assumption is the finding that only vaccines that elicit MHC-E restricted CD8+ T cells protect against challenge in a non-human primate model for AIDS. In addition, MHC-E has limited polymorphisms such that protective responses that target MHC-E-restricted epitopes are conserved among individuals. Therefore, in some embodiments, the genetically modified CMV vaccine vectors described herein elicit an MHC-E restricted T cell response that is shared across genetically diverse individuals.

Disclosed herein are CMV vectors comprising a first nucleic acid sequence that encodes at least one heterologous antigen; and a second nucleic acid sequence comprising a microRNA recognition element (MRE) that silences expression in the presence of a microRNA that is expressed by a cell of endothelial lineage. The MRE is operably linked to a CMV gene that is essential or augmenting for CMV growth. The vectors do not express: an active UL128 protein or ortholog thereof; an active UL130 protein or ortholog thereof; an active UL146 protein or ortholog thereof; or an active UL147 protein or orthologs thereof.

Also disclosed herein are CMV vectors comprising a first nucleic acid sequence that encodes at least one heterologous antigen; a second nucleic acid sequence comprising a MRE that silences expression in the presence of a microRNA that is expressed by a cell of endothelial lineage; and a third nucleic acid sequence comprising an MRE that silences expression in the presence of a microRNA that is expressed by a cell of myeloid lineage. The MREs are operably linked to a CMV gene that is essential or augmenting for CMV growth. The vectors do not express: an active UL128 protein or ortholog thereof; an active UL130 protein or ortholog thereof; an active UL146 protein or ortholog thereof; or an active UL147 protein or ortholog thereof.

Also disclosed herein are human cytomegalovirus (HCMV) vectors comprising a nucleic acid sequence that encodes at least one heterologous antigen. The vectors do not express: an active UL128 protein or ortholog thereof; an active UL130 protein or ortholog thereof; an active UL146 protein or ortholog thereof; or an active UL147 protein or ortholog thereof.

Also disclosed herein are methods of generating an immune response to at least one heterologous antigen in a subject. The methods involve administering to the subject a CMV vector of the type disclosed herein in an amount effective to elicit a CD8+ T cell response to the at least one heterologous antigen. In some embodiments, at least 10% of the CD8+ T cells elicited by the vector are restricted by MHC-E or an ortholog thereof. In additional embodiments, fewer than 10% of the CD8+ T cells elicited by the vector are restricted by polymorphic MHC-class Ia or an ortholog thereof. In alternative embodiments, at least 50% of the CD8+ T cells elicited by the vector are restricted by MHC-class Ia or an ortholog thereof. In yet other embodiments, at least 10% of the CD8+ T cells elicited by the vector are restricted by MHC-II or an ortholog thereof.

The heterologous antigen of the CMV vectors disclosed herein may be any heterologous antigen, including a pathogen-specific antigen derived from, for example, human immunodeficiency virus (HIV), simian immunodeficiency virus (SIV), herpes simplex virus type 1 (HSV-1), herpes simplex virus type 2 (HSV-2) hepatitis B virus, hepatitis C virus, papillomavirus, *Plasmodium* parasites, and *Mycobacterium tuberculosis*. In other embodiments, the heterologous antigen may be a tumor antigen including, for example, a tumor antigen related to acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma, and germ cell tumors. In some embodiments, the heterologous antigen may be a tissue-specific antigen or a host self-antigen including, for example, an antigen derived from the variable region of a T cell receptor or an antigen derived from the variable region of a B cell receptor.

Also disclosed herein is a method of generating CD8+ T cells that recognize MHC-E-peptide complexes. This method involves administering to a first subject a CMV vector in an amount effective to generate a set of CD8+ T cells that recognize MHC-E/peptide complexes. The CMV vector comprises a first nucleic acid sequence encoding at least one heterologous antigen and does not express an active UL128 protein or ortholog thereof; an active UL130 protein or ortholog thereof; an active UL146 protein or ortholog thereof; or an active UL147 protein or ortholog thereof. In some embodiments, the CMV vector further comprises a second nucleic acid sequence comprising a MRE that silences expression in the presence of a microRNA that is expressed by a cell of endothelial lineage. The heterologous antigen can be any antigen, including a pathogen specific antigen, a tumor antigen, a self-antigen, or a tissue-specific antigen. In some embodiments, this method may further comprise identifying a first CD8+ T cell receptor from the set of CD8+ T cells, wherein the first CD8+ T cell receptor (TCR) recognizes a MHC-E/heterologous antigen-derived peptide complex. In some embodiments, the first CD8+ T cell receptor is identified by DNA or RNA sequencing. In some embodiments, this method may further comprise transfecting one or more T cells isolated from the first subject or a second subject with an expression vector, wherein the expression vector comprises a nucleic acid sequence encoding a second CD8+ T cell receptor, wherein the second CD8+ T cell receptor comprises CDR3α and CDR3β of the first CD8+ T cell receptor, thereby generating one or more transfected CD8+ T cells that recognize a MHC-E/heterologous antigen-derived peptide complex. In some embodiments, this method may further comprise administering the transfected CD8+ T cells to the first or second subject to treat a disease, such as cancer, a pathogenic infection, or an autoimmune disease or disorder. In some embodiments, this method may further comprise administering the transfected CD8+ T cells to the first or second subject to induce an autoimmune response to a self-antigen or a tissue-specific antigen.

Also disclosed herein is a transfected CD8+ T cell that recognizes MHC-E-peptide complexes prepared by a process comprising the steps of: (1) administering to a first subject a CMV vector in an amount effective to generate a set of CD8+ T cells that recognize MHC-E/peptide complexes, (2) identifying a first CD8+ T cell receptor from the set of CD8+ T cells, wherein the first CD8+ T cell receptor recognizes a MHC-E/heterologous antigen-derived complex; (3) isolating one or more CD8+ T cells from the first subject or a second subject; and (4) transfecting the one or more CD8+ T cells isolated from the first or second subject with an expression vector, thereby creating a transfected T cell that recognizes MHC-E-peptide complexes. The CMV vector comprises a first nucleic acid sequence encoding at least one heterologous antigen and does not express an active UL128 protein or ortholog thereof; an active UL130 protein or ortholog thereof; an active UL146 protein or ortholog thereof; or an active UL147 protein or ortholog thereof. In some embodiments, the CMV vector further comprises a second nucleic acid sequence comprising a MRE that silences expression in the presence of a microRNA that is expressed by a cell of endothelial lineage. The expression vector comprises a nucleic acid sequence encoding a second CD8+ T cell receptor and a promoter operably linked to the nucleic acid sequence encoding the second CD8+ T cell receptor, wherein the second CD8+ T cell receptor comprises CDR3a and CDR30 of the first CD8+ T cell receptor. The heterologous antigen can be any antigen, including a pathogen specific antigen, a tumor antigen, a self-antigen, or a tissue-specific antigen. Also disclosed herein are methods of treating a disease, such as cancer, a pathogenic infection, or an autoimmune disease or disorder, the method comprising administering the transfected CD8+ T cell that recognizes MHC-E-peptide complexes to the first or second subject.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

Figure 4:
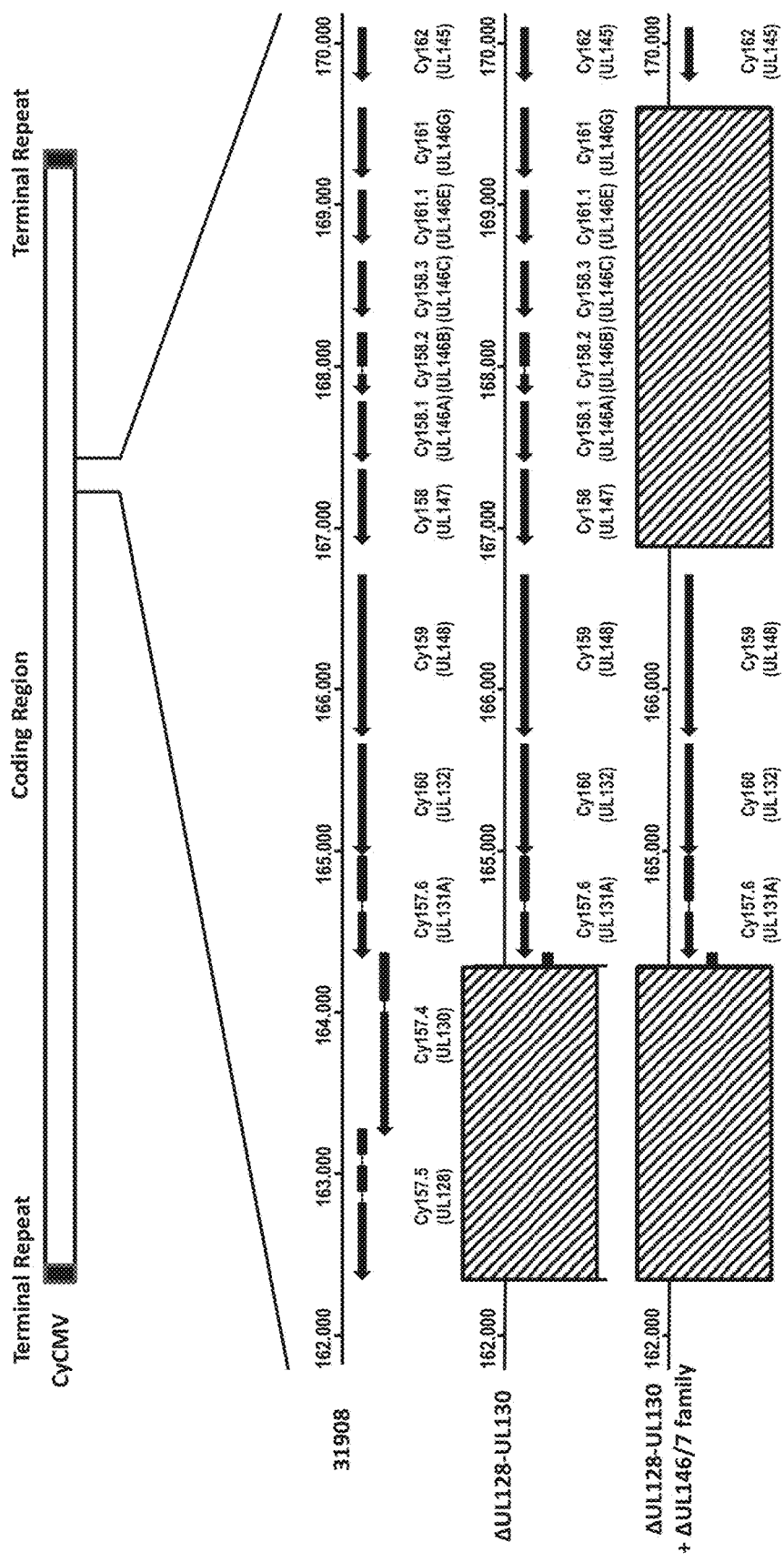

FIG. 4 shows a schematic of CyCMV constructs generated by cloning into a bacterial artificial chromosome (31908) and deleted for genes homologous to HCMV UL128 and UL130 (ΔUL128-UL130) alone or in combination with a family of six genes homologous to HCMV UL146 and UL147 (ΔUL128-UL130+ΔUL146/7 family).

Figure 5A:
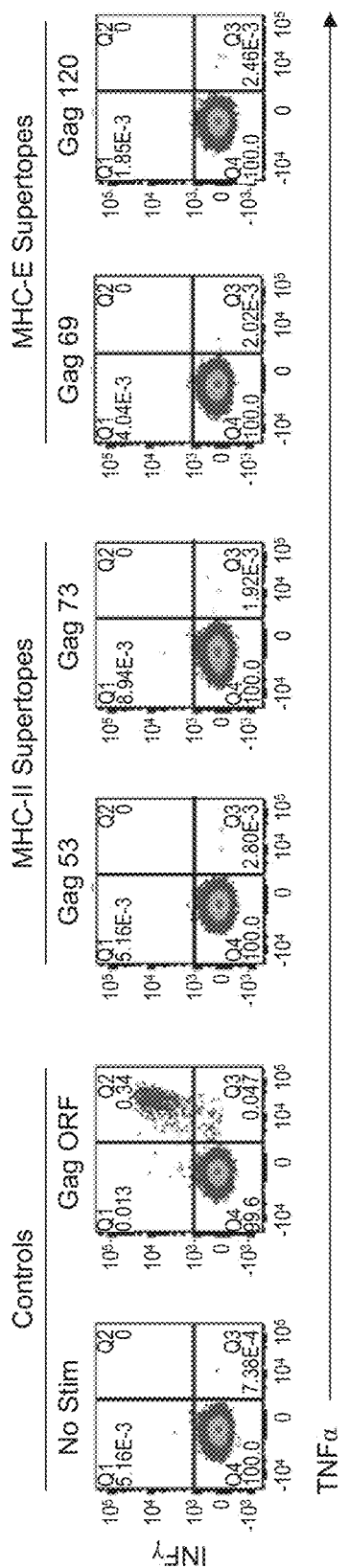
Figure 5B:
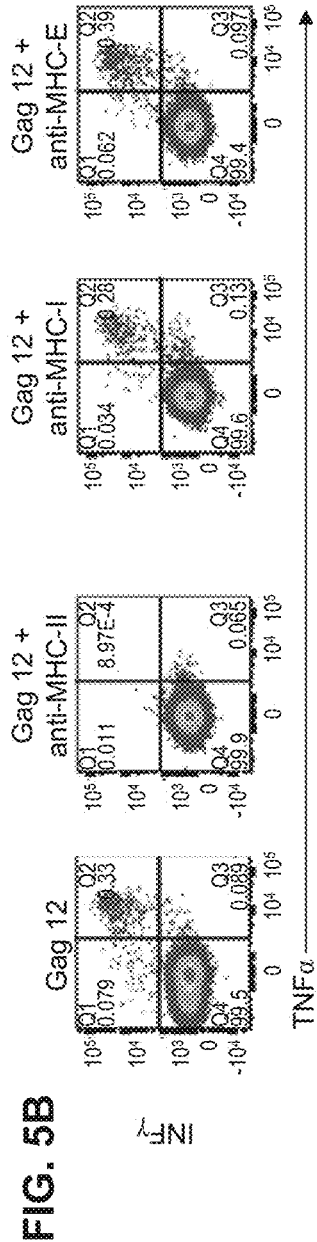
Figure 5C:
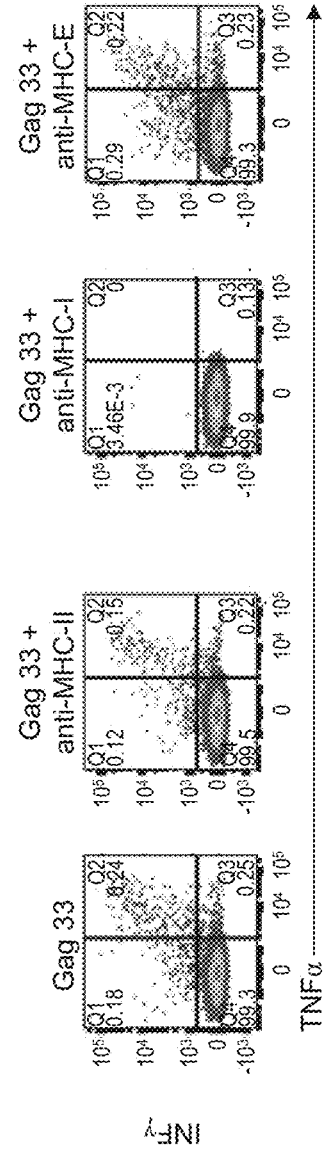
Figure 5C:
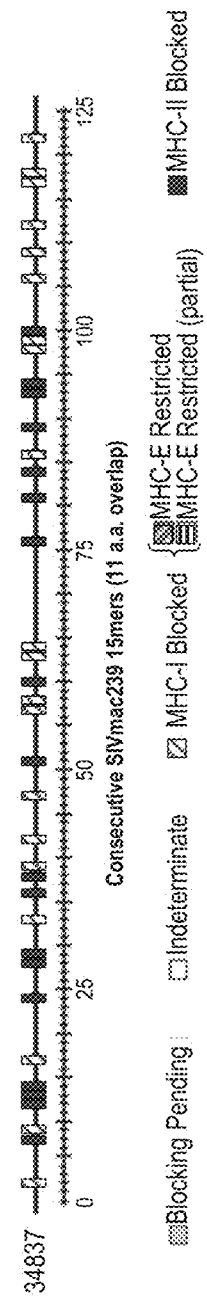

FIGS. 5A-5C show flow cytometry plots of peripheral blood mononuclear cells (PBMC) from CyCMVΔRL13/GagΔUL128-130 vector-vaccinated cynomolgus macaques. FIG. 5A shows flow cytometry plots of PBMC from CyCMVΔRL13/GagΔUL128-130 vector-vaccinated cynomolgus macaques stimulated with 15 mer SIVgag peptides overlapping by four amino acids (GAG ORF) or with the indicated SIVgag peptides corresponding to MHC-II or MHC-E supertopes (Gag53=peptide corresponding to amino-acid sequence 211-222 in the gag protein of SIVmac239; Gag73=AA 290-301, Gag69=AA 276-284, Gag120=AA 482-490). FIG. 5B shows representative flow cytometry plots of CD8+ T cells following incubation with non-supertope MHC-II or MHC-Ia-restricted peptides (Gag12=AA 45-59 in SIVmac239gag, Gag33=132-140 AA) in the presence of the pan-MHC-I blocking mAb W6/32 (anti-MHC-I blocking both MHC-E and MHC-Ia), the MHC-II binding CLIP peptide (anti-MHC-II), or MHC-E binding VL9 peptide (anti-MHC-E). FIG. 5C shows the epitope targeting and MHC restriction of SIVgag-specific CD8+ T cells using flow cytometric ICS to detect recognition of 125 consecutive 15mer gag peptides (with 11 amino acid overlap). Individual peptides resulting in specific CD8+ T cell responses are indicated by a box, with the pattern of the box designating MHC restriction, as determined by blocking with the anti-pan-MHC-I mAb W6/32, the MHC-E blocking peptide VL9, and the MHC-II blocking peptide CLIP. MHC-Ia-, MHC-E-, and MHC-II-restriction was based on >90% response blocking by W6/32 alone (hatch marks directed from bottom left corner to upper right corner), VL9 alone (hatch marks directed from bottom right corner to upper left corner; horizontal hatch marks), and CLIP alone (solid fill), respectively, with responses not meeting these criteria labeled indeterminate (no fill).

Figure 6A:
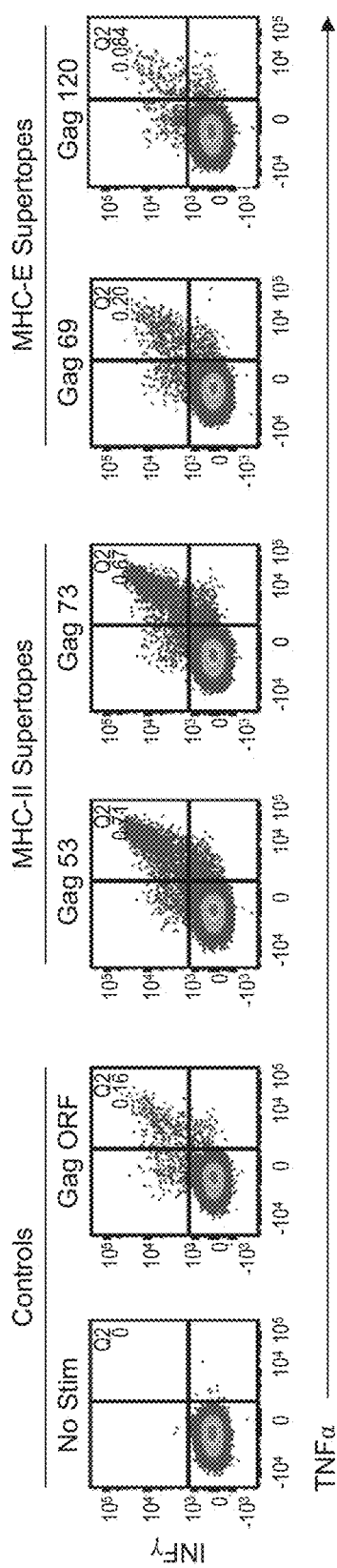

FIGS. 6A-6C show flow cytometry plots of PBMC from CyCMVΔRL13/GagΔUL128-130ΔUL146-147 vector-vaccinated cynomolgus macaques. FIG. 6A shows flow cytometry plots of PBMC from CyCMVΔRL13/GagΔUL128-130ΔUL146-147 vector-vaccinated cynomolgus macaques stimulated with 15 mer SIVgag peptides overlapping by four amino acids (GAG ORF) or with indicated SIVgag peptides corresponding to MHC-II or MHC-E supertopes. FIG. 6B shows representative flow cytometry plots of CD8+ T cells following incubation with supertope MHC-II- or MHC-E-restricted peptides in the presence of the pan-MHC-I blocking mAb W6/32 (anti-MHC-I), the MHC-II binding CLIP peptide (anti-MHC-II), or the MHC-E binding VL9 peptide (anti-MHC-E). FIG. 6C shows the epitope targeting and MHC restriction of SIVgag-specific CD8+ T cells using flow cytometric ICS to detect recognition of 125 consecutive 15mer gag peptides (with 11 amino acid overlap). Individual peptides resulting in specific CD8+ T cell responses are indicated by a box, with the pattern of the box designating MHC restriction, as determined by blocking with the anti-pan-MHC-I mAb W6/32, the MHC-E blocking peptide VL9, and the MHC-II blocking peptide CLIP. MHC-Ia-, MHC-E-, and MHC-II-restriction was based on >90% response blocking by W6/32 alone (hatch marks directed from bottom left corner to upper right corner), VL9 alone (hatch marks directed from bottom right corner to upper left corner; horizontal hatch marks), and CLIP alone (solid fill), respectively, with responses not meeting these criteria labeled indeterminate (no fill).

Figure 7:
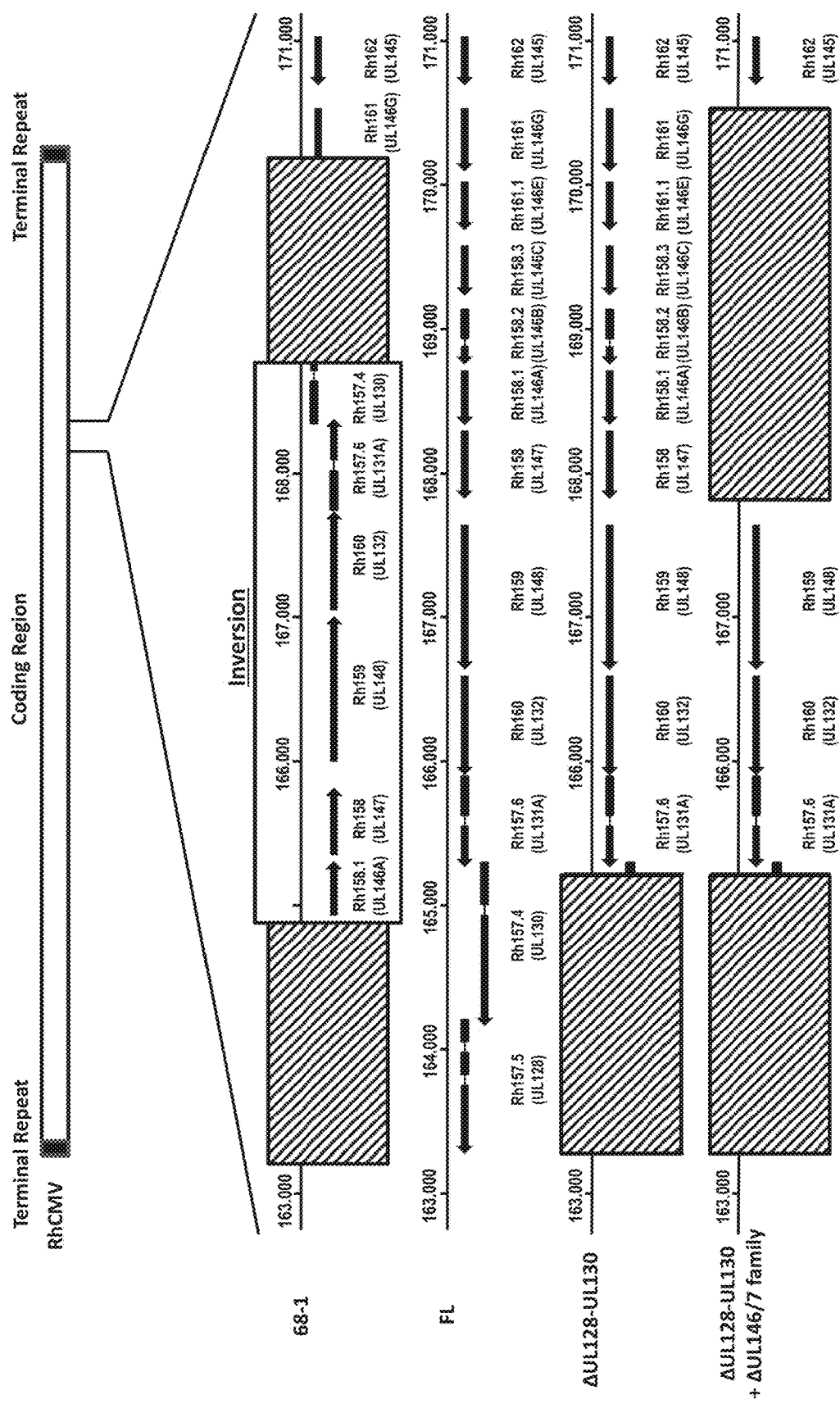

FIG. 7 shows a schematic of RhCMV isolate 68-1 and RhCMV constructs generated by genetic engineering of 68-1 into the wildtype, full-length genome (FL). Certain constructs of FL were deleted for RhCMV genes homologous to HCMV UL128 and UL130 (ΔUL128-UL130) alone or in combination with a family of six RhCMV genes homologous to HCMV UL146 and UL147 (ΔUL128-UL130+ΔUL146/7 family).

FIGS. 8A-8D show CD8+ T cell responses to whole SIVgag (using overlapping peptides) or the indicated MHC-E or MHC-II restricted "supertope" peptides in rhesus monkeys inoculated with the indicated constructs. T cell responses were measured via ICS in PBMC at the indicated days post-inoculation. FIG. 5A shows the CD8+ T cell responses of rhesus monkeys inoculated with FL-RhCMVΔRL13gag. FIG. 8B shows the CD8+ T cell responses of rhesus monkeys inoculated with FL-RhCMVΔRL13gagΔUL128-UL130. FIG. 8C shows the CD8+ T cell responses of rhesus monkeys inoculated with FL-RhCMVΔRL13gagΔUL128-UL130ΔUL146(3). FIG. 8D shows the CD8+ T cell responses of rhesus monkeys inoculated with FL-RhCMVΔRL13gagΔUL128-UL130ΔUL147(6).

Figure 9A:
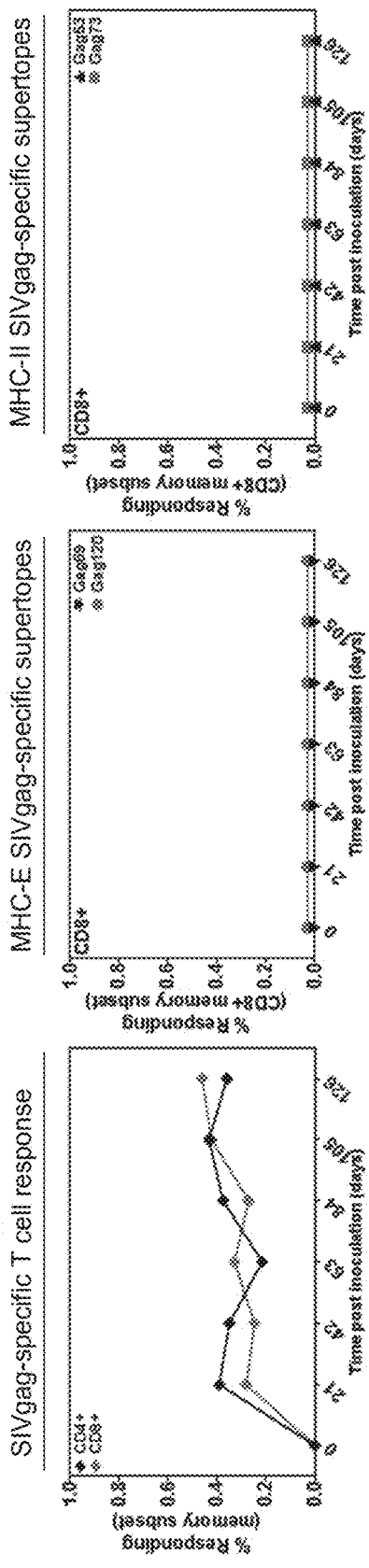
Figure 9B:
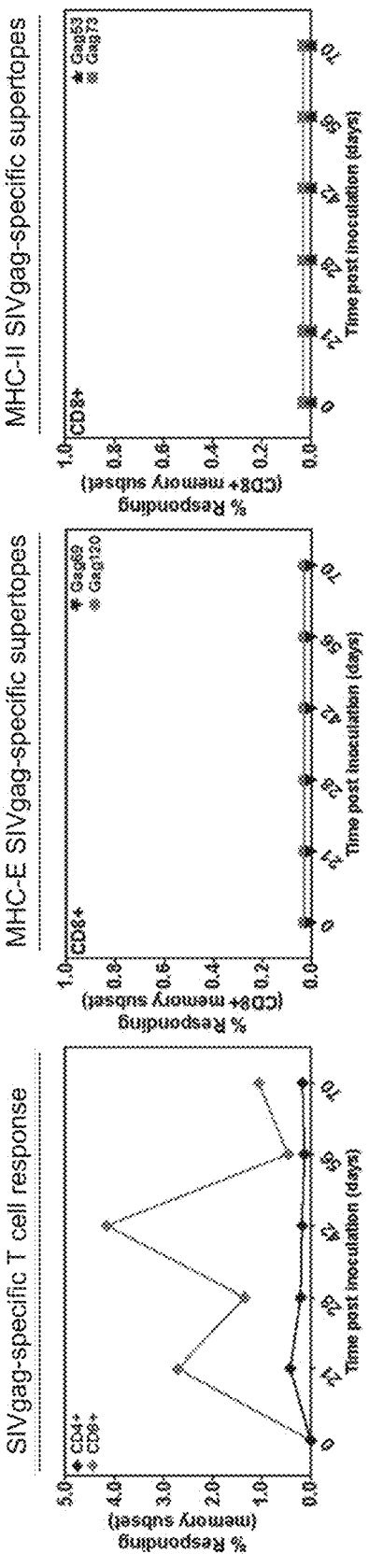
Figure 9C:
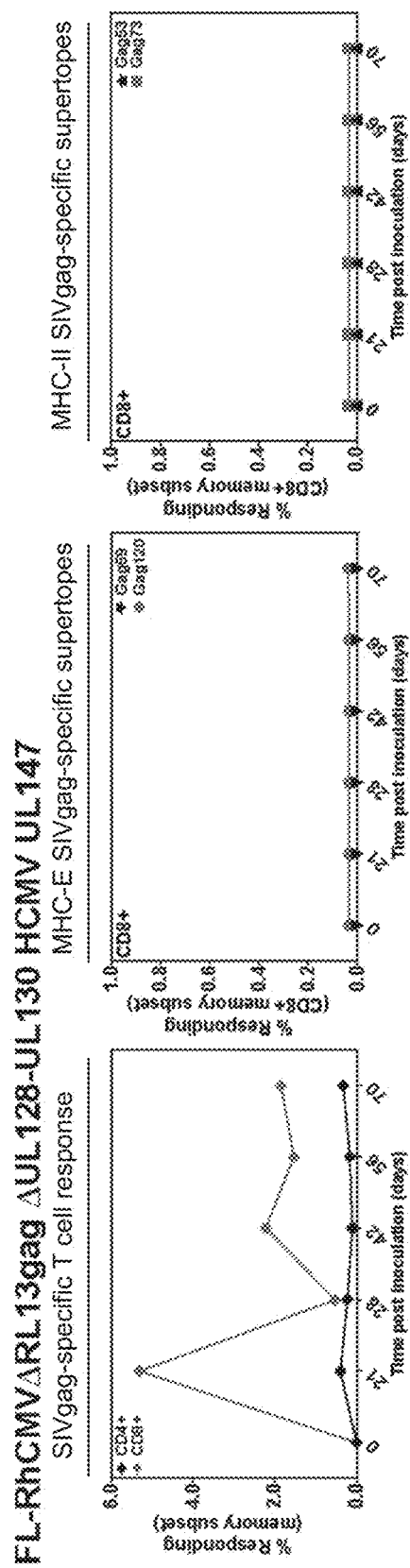

FIGS. 9A-9C show CD8+ T cell responses to whole SIVgag (using overlapping peptides) or the indicated MHC-E or MHC-II restricted "supertope" peptides in rhesus monkeys inoculated with the indicated constructs. T cell responses were measured via ICS in PBMC at the indicated days post-inoculation. FIG. 9A shows the CD8+ T cell responses of rhesus monkeys inoculated with FL-RhCMVΔRL13gagΔUL128-UL130HCMVUL146-UL147. FIG. 9B shows the CD8+ T cell responses of rhesus monkeys inoculated with FL-RhCMVΔRL13gagΔUL128-UL130HCMVUL146. FIG. 9C shows the CD8+ T cell responses of rhesus monkeys inoculated with FL-RhCMVΔRL13gagΔUL128-UL130HCMVUL147.

Figure 10:
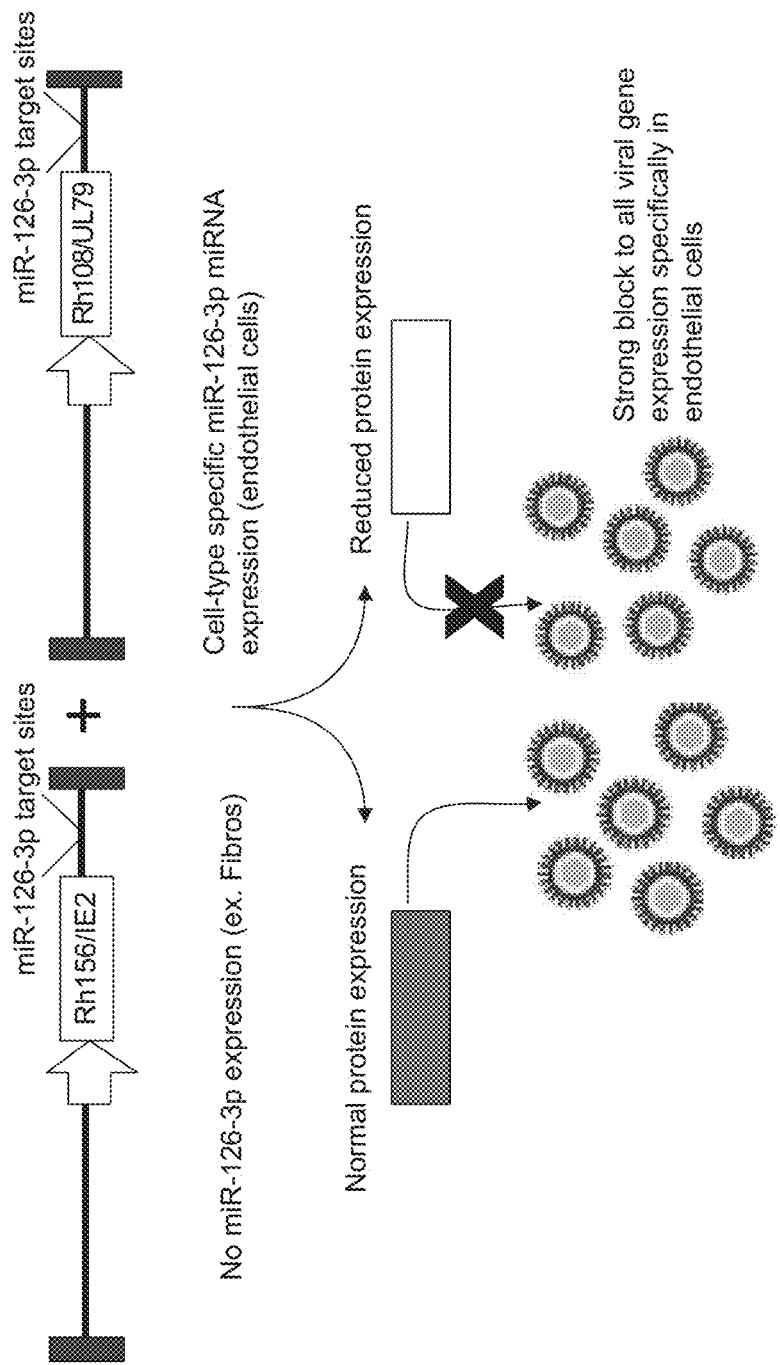

FIG. 10 shows a schematic of the generation of RhCMV Rh156/Rh108 miR-126-3p mutant virus via galK recombination. Rh156 and Rh108 are the RhCMV homologs of the essential HCMV genes UL122 (IE2) and UL79, respectively.

Figure 11:
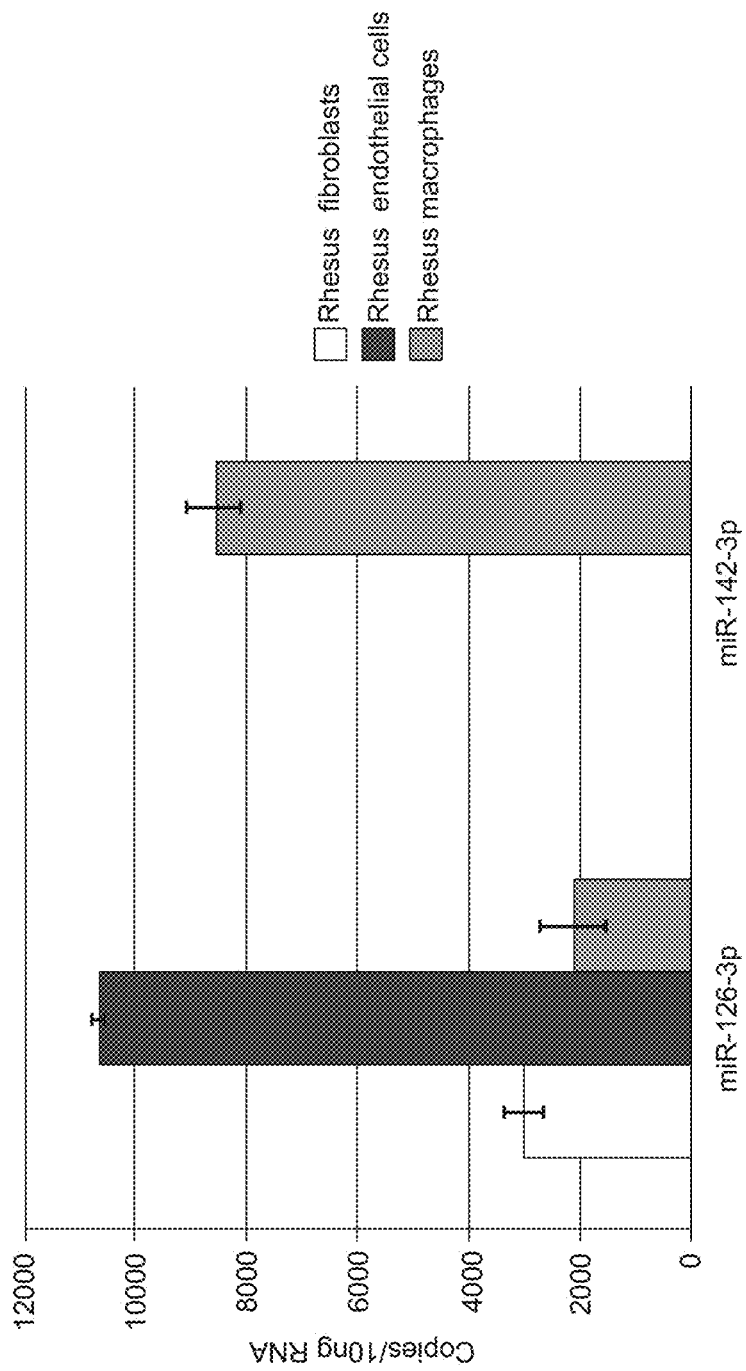

FIG. 11 is a bar graph showing miR-126-3p expression in the indicated cell types (rhesus lung fibroblasts, rhesus umbilical vein endothelial cells, rhesus macrophages derived from CD14+ monocytes obtained from PBMCs and cultured in the presence of m-CSF for 10 days). MiR expression was measured by qPCR from 10 ng of RNA. The copy number was determined by standard curve.

Figure 12:
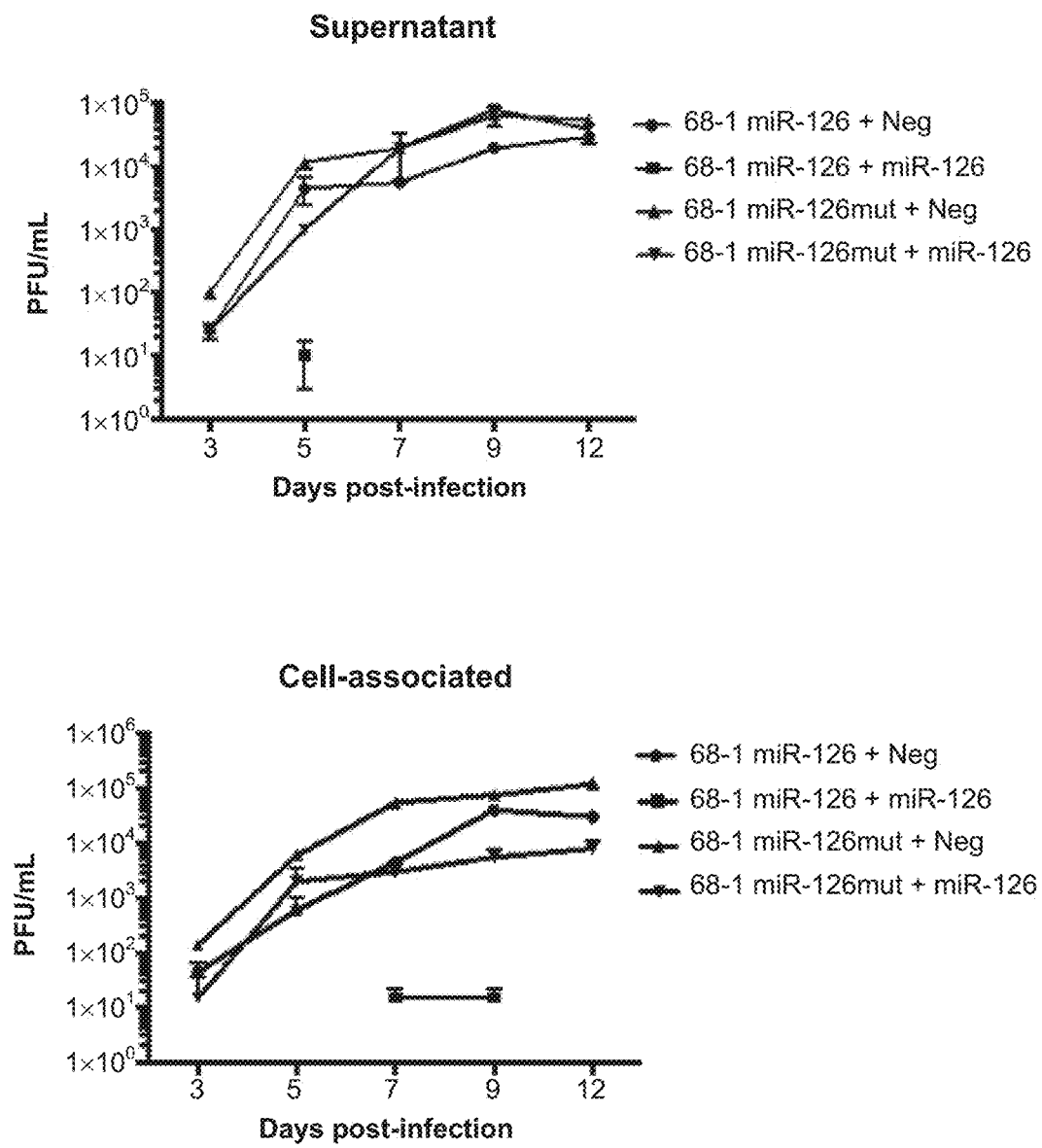

FIG. 12 shows a set of two plots indicating a multi-step growth curve using RhCMV 68-1 RTN Rh156/Rh108 miR-126-3p ("68-1 miR-126") virus or RhCMV 68-1 RTN Rh156/Rh108 miR-126 mutant ("68-1 miR-126mut") virus in rhesus fibroblasts transfected with miR-126-3p mimics ("+miR-126") or control miRNAs ("+Neg"). Strain 68-1 RhCMV lacks homologs of HCMV UL128 and UL130 as well as UL146 and UL147. RTN=a fusion protein of rev, tat and nef proteins of SIVmac239 expressed via the EF1a promoter and inserted into the RhCMV gene Rh211. This virus contains four targeting sequences for mir126-3p in the 3'-untranslated regions of each Rh156 and Rh108.

Figure 13:
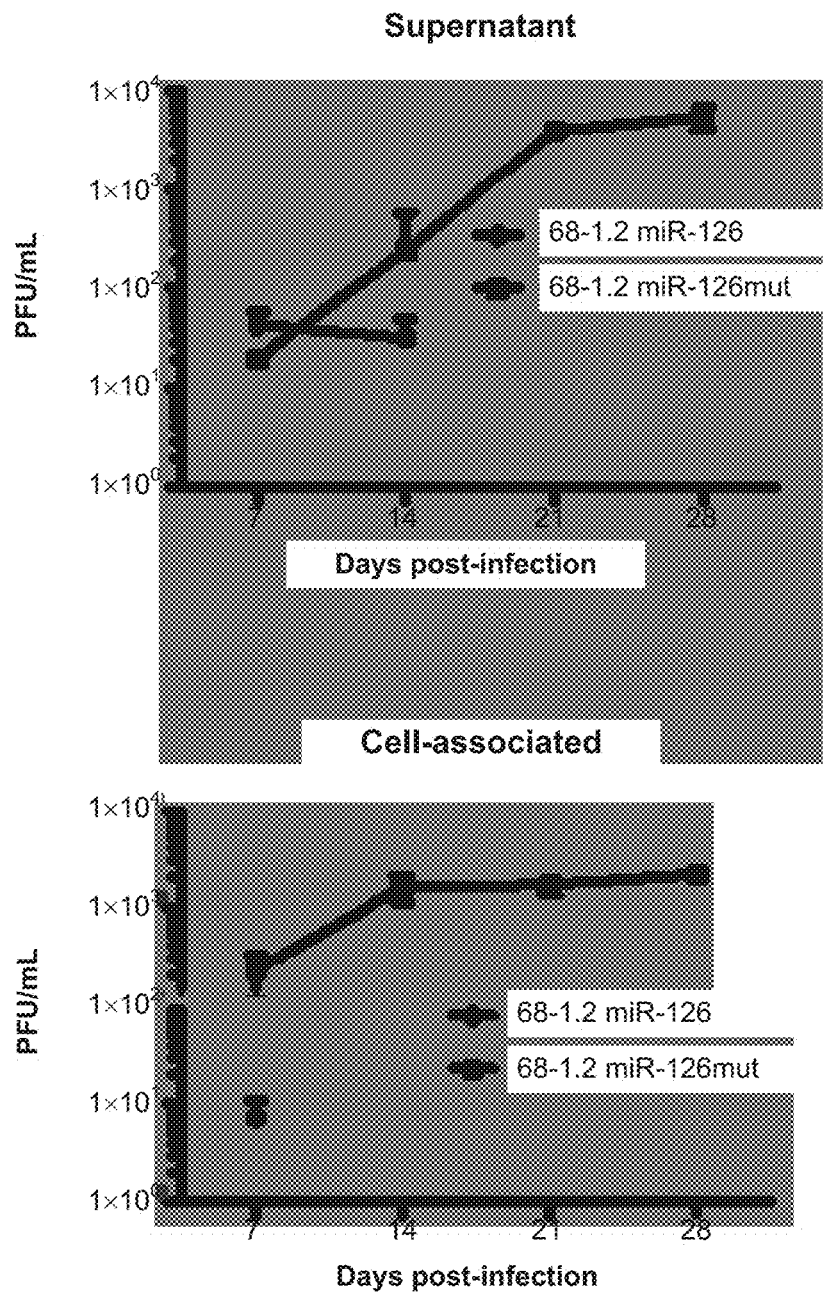

FIG. 13 shows a set of two plots indicating a multi-step growth curve using RhCMV 68-1.2 Rh156/Rh108 miR-126-

3p ("68-1.2 miR-126") virus or RhCMV 68-1 Rh156/Rh108 miR-126 mutant ("68-1.2 miR-126mut") virus in endothelial cells. Strain 68-1.2 contains the UL128 and UL130 homologs of a different RhCMV strain and is deleted for the homologs of UL146 and UL147. This virus contains four targeting sequences for mir126-3p in the 3'-untranslated regions of each Rh156 and Rh108.

Figure 14:
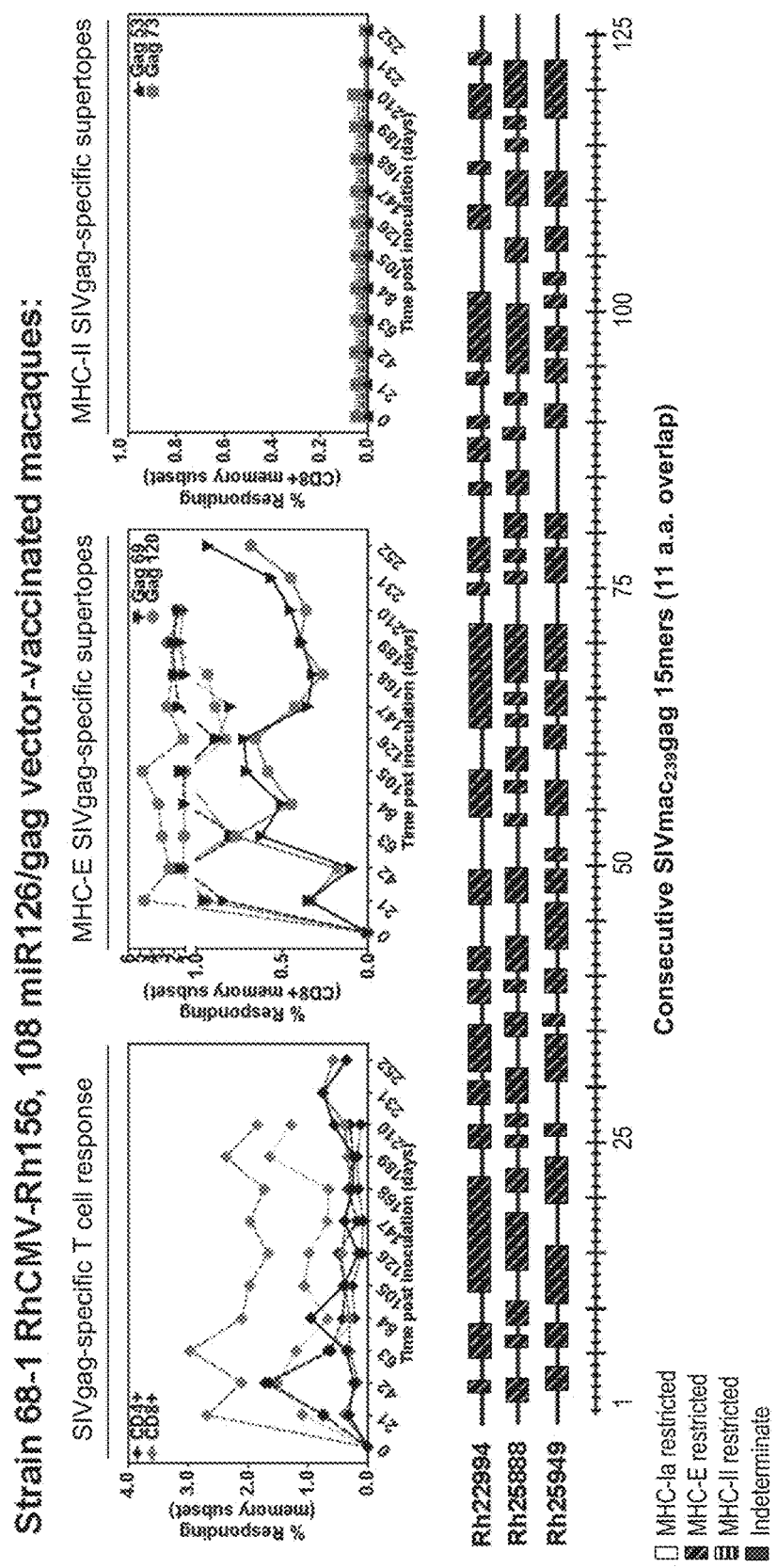

FIG. 14 shows the SIVgag-specific T cell frequencies in rhesus monkeys (RM) inoculated with 68-1 RhCMVmiR126/SIVgag and the associated epitope targeting and MHC restriction of SIVgag-specific CD8+ T cells. Strain 68-1 RhCMV lacks homologs of HCMV UL128 and UL130 as well as UL146 and UL147. SIVgag of SIVmac239 is expressed via the EF1a promoter and inserted into the RhCMV gene Rh211. This virus contains four targeting sequences for mir126-3p in the 3'-untranslated regions of each Rh156 and Rh108.

The top panels of FIG. 14 show the SIVgag-specific T cell frequencies measured over time in 2 RM inoculated with 68-1 RhCMVmir126/SIVgag. The top left panel shows the CD4+ and CD8+ T cell response to SIVgag in each RM to a pool of 125 overlapping 15mer peptides overlapping by 4 amino-acids and covering the entire SIVgag protein. The top middle panel shows the CD8+ T cell response in each RM to the two SIVgag supertope peptides Gag69 and Gag120 presented by MHC-E. The top right panel shows the CD8+ T cell response in each RM to the two SIVgag supertope peptides Gag53 and Gag73 presented by MHC-II. The bottom panel of FIG. 14 shows the epitope targeting and MHC restriction of SIVgag-specific CD8+ T cells with individual peptides resulting in specific CD8+ T cell responses indicated by a box. The pattern of the box designates MHC restriction, as determined by blocking with the anti-pan-MHC-I mAb W6/32, the MHC-E blocking peptide VL9, and the MHC-II blocking peptide CLIP. MHC-Ia-, MHC-E-, and MHC-II-restriction was based on >90% response blocking by W6/32 alone (solid fill), W6/32 and VL9 alone (intermediate fill), and CLIP alone (light fill), respectively, with responses not meeting these criteria labeled indeterminate (no fill).

Figure 15:
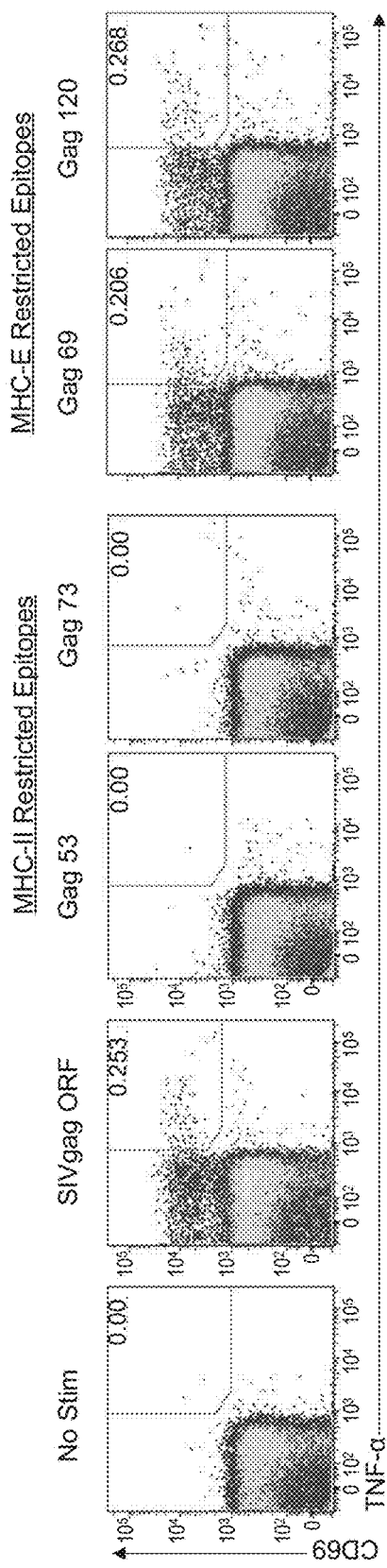

FIG. 15 is a set of flow cytometry plots showing PBMC from strain RhCMV 68-1miR126/gag vector-vaccinated rhesus macaques stimulated with 15 mer SIVgag peptides overlapping by four amino acids (SIVgag ORF) or with indicated SIVgag peptides corresponding to MHC-II or MHC-E supertopes. CD8+ T cells responding to the MHC-E or MHC-II-bound SIVgag peptides were identified via CD69 and TNF-α expression.

Figure 16:
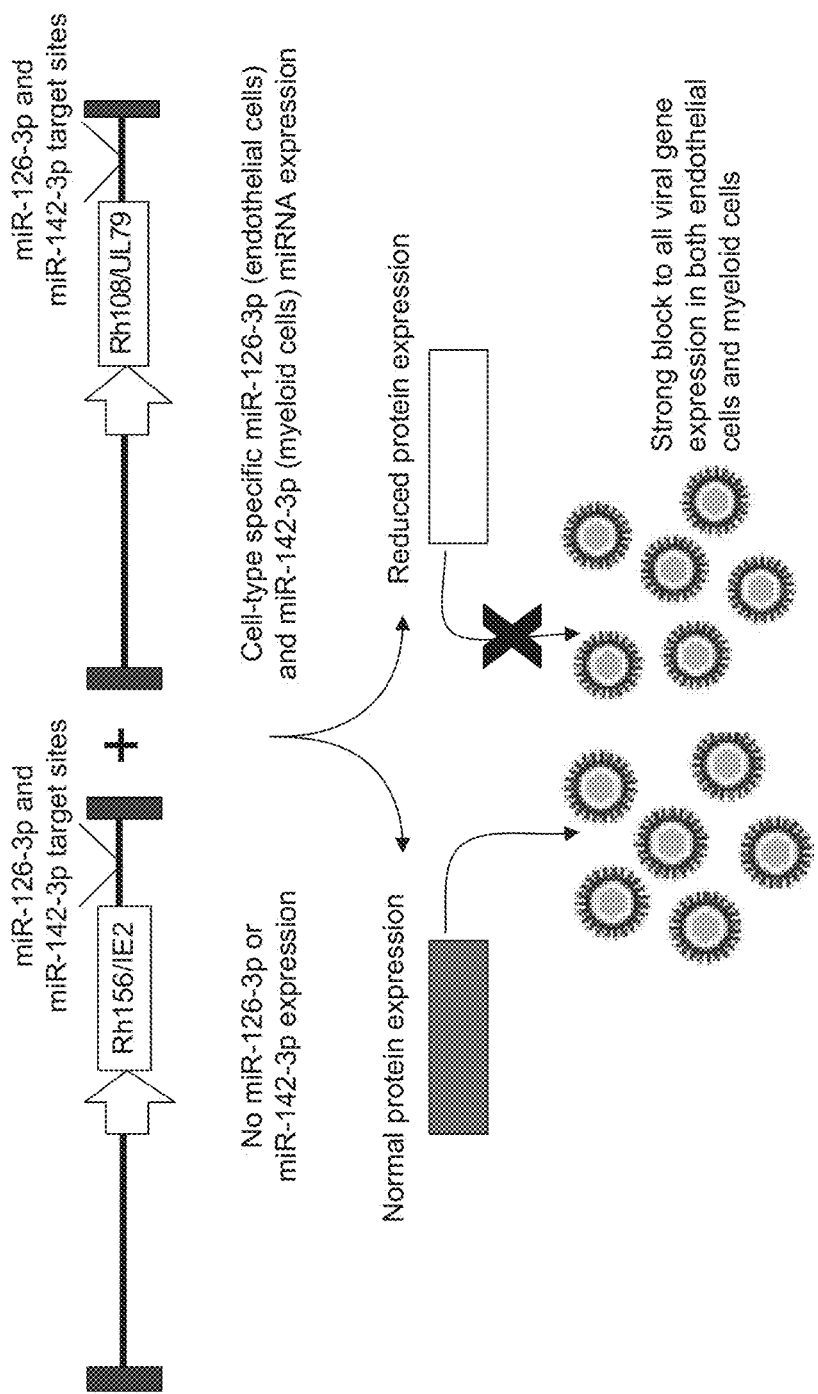

FIG. 16 shows a schematic of the generation of RhCMV Rh156/Rh108 miR-126-3p/miR-142-3p mutant virus via galK recombination. Rh156 and Rh108 are the RhCMV homologs of the essential HCMV genes UL122 (IE2) and UL79, respectively.

Figure 17:
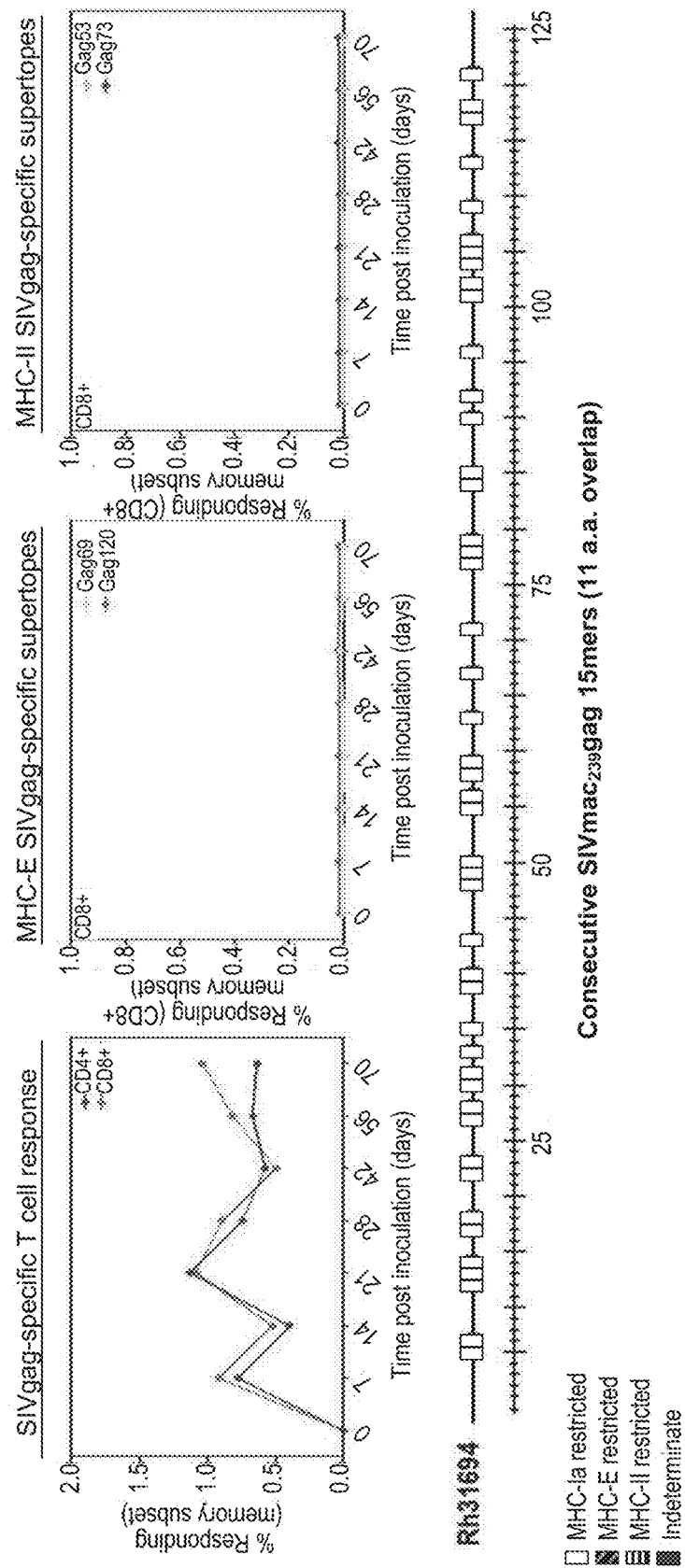

FIG. 17 shows the SIVgag-specific T cell frequencies in rhesus monkeys (RM) inoculated with 68-1 RhCMVmir126mir142/SIVgag and the associated epitope targeting and MHC restriction of SIVgag-specific CD8+ T cells. Strain 68-1 RhCMV lacks homologs of HCMV UL128 and UL130 as well as UL146 and UL147. SIVgag of SIVmac239 is expressed via the EF1a promoter and inserted into the RhCMV gene Rh211. This virus contains two targeting sequences for mir126-3p and two targeting sequences for the myeloid-specific mir142-3p in the 3'-untranslated regions of each Rh156 and Rh108.

The top panel of FIG. 17 show the SIVgag-specific T cell frequencies measured over time in one RM inoculated with 68-1 RhCMVmir126mir142/SIVgag. The top left panel of FIG. 17 shows the CD4+ and CD8+ T cell response to SIVgag in each RM to a pool of 125 overlapping 15mer peptides overlapping by 4 amino-acids and covering the entire SIVgag protein. The top middle panel of FIG. 17 shows the CD8+ T cell response in each RM to two common SIVgag peptides presented by MHC-E. The top right panel of FIG. 17 shows the CD8+ T cell response in each RM to two common SIVgag peptides presented by MHC-II. The bottom panel of FIG. 17 shows the epitope targeting and MHC restriction of SIVgag-specific CD8+ T cells with individual peptides resulting in specific CD8+ T cell responses are indicated by a box. The pattern of the box designates MHC restriction, as determined by blocking with the anti-pan-MHC-I mAb W6/32, the MHC-E blocking peptide VL9 and the MHC-II blocking peptide CLIP. MHC-Ia-, MHC-E-, and MHC-II-restriction was based on >90% response blocking by W6/32 alone (no fill), W6/32 and VL9 alone (diagonal hatch marks), and CLIP alone (horizontal hatch marks), respectively, with responses not meeting these criteria labeled indeterminate (solid fill). These results indicate that 68-1 RhCMV (=deleted for homologs of UL128, UL130, UL146, UL147)mir126mir142/SIVgag elicits only MHC-Ia-restricted CD8+ T cells.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope of the disclosure. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide recombinant CMV vectors including but not limited to recombinant CMV vectors comprising a nucleic acid encoding at least one heterologous protein antigen, and at least one microRNA recognition element specific for a microRNA expressed by a cell of endothelial lineage that is operably linked to a CMV gene that is essential or augmenting for CMV growth. The vectors do not express: an active UL128 protein or ortholog thereof; an active UL130 protein or ortholog thereof; or active UL146/147 proteins or orthologs thereof. Also provided herein are human cytomegalovirus (HCMV) vectors including but not limited to recombinant HCMV vectors comprising a nucleic acid encoding at least one heterologous protein antigen and which do not express: an active UL128 protein or ortholog thereof; an active UL130 protein or ortholog thereof; or active UL146/147 proteins or orthologs thereof. Methods of using the novel, recombinant CMV vectors, such as methods of generating an immune response to the heterologous antigen in the subject are further disclosed.

I. Terms

Unless otherwise noted, technical terms are used according to conventional usage.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

Although methods and materials similar or equivalent to those described herein may be used in the practice or testing of this disclosure, suitable methods and materials are described below. In addition, the materials, methods, and examples are illustrative only and not intended to be limiting. In order to facilitate review of the various embodiments of the disclosure, the following explanations of specific terms are provided:

Antigen: As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) the protein is able to evoke an immune response of the humoral and/or cellular type directed against that protein.

Administration: As used herein, the term "administration" means to provide or give a subject an agent, such as a composition comprising an effective amount of a CMV vector comprising an exogenous antigen by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Effective amount: As used herein, the term "effective amount" refers to an amount of an agent, such as a CMV vector comprising a heterologous antigen or a transfected CD8+ T cell that recognizes a MHC-E/heterologous antigen-derived peptide complex, that is sufficient to generate a desired response, such as reduce or eliminate a sign or symptom of a condition or disease or induce an immune response to an antigen. In some examples, an "effective amount" is one that treats (including prophylaxis) one or more symptoms and/or underlying causes of any of a disorder or disease. An effective amount may be a therapeutically effective amount, including an amount that prevents one or more signs or symptoms of a particular disease or condition from developing, such as one or more signs or symptoms associated with infectious disease, cancer, or autoimmune disease.

MicroRNA: As used herein, the term "microRNA" or "miRNA" refers to a major class of biomolecules involved in control of gene expression. For example, in human heart, liver or brain, miRNAs play a role in tissue specification or cell lineage decisions. In addition, miRNAs influence a variety of processes, including early development, cell proliferation and cell death, and apoptosis and fat metabolism. The large number of miRNA genes, the diverse expression patterns, and the abundance of potential miRNA targets suggest that miRNAs may be a significant source of genetic diversity.

A mature miRNA is typically an 18-25 nucleotide non-coding RNA that regulates expression of an mRNA including sequences complementary to the miRNA. These small RNA molecules are known to control gene expression by regulating the stability and/or translation of mRNAs. For example, miRNAs bind to the 3' UTR of target mRNAs and suppress translation. MiRNAs may also bind to target mRNAs and mediate gene silencing through the RNAi pathway. MiRNAs may also regulate gene expression by causing chromatin condensation.

A miRNA silences translation of one or more specific mRNA molecules by binding to a miRNA recognition element (MRE), which is defined as any sequence that directly base pairs with and interacts with the miRNA somewhere on the mRNA transcript. Often, the MRE is present in the 3' untranslated region (UTR) of the mRNA, but it may also be present in the coding sequence or in the 5' UTR. MREs are not necessarily perfect complements to miRNAs, usually having only a few bases of complementarity to the miRNA and often containing one or more mismatches within those bases of complementarity. The MRE may be any sequence capable of being bound by a miRNA sufficiently that the translation of a gene to which the MRE is operably linked (such as a CMV gene that is essential or augmenting for growth in vivo) is repressed by a miRNA silencing mechanism such as the RISC.

Mutation: As used herein, the term "mutation" refers to any difference in a nucleic acid or polypeptide sequence from a normal, consensus, or "wild type" sequence. A mutant is any protein or nucleic acid sequence comprising a mutation. In addition, a cell or an organism with a mutation may also be referred to as a mutant.

Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence. A mutation that results in a difference in an amino acid may also be called an amino acid substitution mutation. Amino acid substitution mutations may be described by the amino acid change relative to wild type at a particular position in the amino acid sequence.

Nucleotide sequences or nucleic acid sequences: The terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double stranded (duplex). Duplex nucleic acids may be homoduplex or heteroduplex.

Operably Linked: As the term "operably linked" is used herein, a first nucleic acid sequence is operably linked with a second nucleic acid sequence when the first nucleic acid sequence is placed in such a way that it has an effect upon the second nucleic acid sequence. For instance, a MRE is operably linked to a coding sequence that it silences if binding of the miRNA to the MRE silences the expression of the coding sequence. Operably linked DNA sequences may be contiguous, or they may operate at a distance.

Promoter: As used herein, the term "promoter" may refer to any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of ordinary skill in the art. A nucleic acid comprising a promoter operably linked to a nucleic acid sequence that codes for a particular polypeptide may be termed an expression vector.

Recombinant: As used herein, the term "recombinant" with reference to a nucleic acid or polypeptide refers to one that has a sequence that is not naturally occurring or has a sequence that is made by an artificial combination of two or more otherwise separated segments of sequence, for example a CMV vector comprising a heterologous antigen and/or made replication deficient by the addition of a miRNA response element operably linked to a CMV gene that is essential or augmenting for growth in vivo. This artificial combination is often accomplished by chemical synthesis or, more commonly, by the artificial manipulation of isolated segments of nucleic acids, e.g., by genetic engineering techniques. A recombinant polypeptide may also refer to a polypeptide that has been made using recombinant nucleic acids, including recombinant nucleic acids transferred to a host organism that is not the natural source of the polypeptide (for example, nucleic acids encoding polypeptides that form a CMV vector comprising a heterologous antigen).

Replication-deficient: As used herein, a "replication deficient" CMV is a virus that once in a host cell, cannot undergo viral replication, is significantly limited in its ability to replicate its genome and thus produce virions, is dissemination-deficient, or is spread-deficient. For example, replication-deficient viruses that are dissemination-deficient are capable of replicating their genomes, but unable to infect another cell either because virus particles are not released from the infected cell or because non-infectious viral particles are released. In another example, replication-deficient viruses that are spread-deficient are capable of replicating their genomes, and may be able to infect another cell, but are not secreted from the infected host and therefore the virus is unable to spread from host to host. In some embodiments, a replication-deficient CMV is a CMV comprising a mutation that results in a lack of expression of one or more genes essential for viral replication ("essential genes") or required for optimal replication ("augmenting genes"). CMV essential and augmenting genes have been described in the art (in particular US 2013/0136768, which is incorporated by reference herein) and are disclosed herein.

Pharmaceutically acceptable carriers: As used herein, a "pharmaceutically acceptable carrier" of use is conventional. *Remington's Pharmaceutical Sciences*, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers may include, for example, pharmaceutical grades of mannitol, lactose, starch, or magnesium stearate. In addition to biologically neutral carriers, pharmaceutical compositions to be administered may contain minor amounts of non-toxic auxiliary substances, such as wetting or emulsifying agents, preservatives, and pH buffering agents and the like, for example sodium acetate or sorbitan monolaurate.

Polynucleotide: As used herein, the term "polynucleotide" refers to a polymer of ribonucleic acid (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid.

Polypeptide: The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

Sequence identity/similarity: As used herein, the identity/similarity between two or more nucleic acid sequences, or two or more amino acid sequences, is expressed in terms of the identity or similarity between the sequences. Sequence identity may be measured in terms of percentage identity; the higher the percentage, the more identical the sequences are. Sequence similarity may be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) may be called "homologs."

Methods of alignment of sequences for comparison are well known in the art. Various programs and alignment algorithms are described in: Smith & Waterman, *Adv Appl Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J*

*Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information may be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, *Comput Appl Biosci* 10, 67-70 (1994.) Other programs use SEG. In addition, a manual alignment may be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and may possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence may be made using this degeneracy to produce multiple nucleic acid molecules that all encode substantially the same protein. Such homologous nucleic acid sequences can, for example, possess at least about 50%, 60%, 70%, 80%, 90%, 95%, 98%, or 99% sequence identity to a nucleic acid that encodes a protein.

Subject: As used herein, the term "subject" refers to a living multi-cellular vertebrate organisms, a category that includes both human and non-human mammals.

Supertope: As used herein, the term "supertope" or "supertope peptide" refers to a epitope or peptide that is recognized by T cells in greater than 90% of the population regardless of MHC haplotype, i.e., in the presence or absence of given MHC-I or MHC-II alleles.

Treatment: As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect may be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

II. Recombinant CMV Vectors and Methods of Using the Same

Disclosed herein are human or animal cytomegalovirus (CMV) vectors capable of repeatedly infecting an organism. The CMV vectors comprise a nucleic acid sequence that encodes a heterologous protein antigen and lack expression of active UL128, UL130, UL146 and UL147 proteins. The vectors contain active UL40, US27 and US28 genes. In some embodiments, the CMV vector is a human CMV (HCMV) vector, a cynomolgus CMV (CyCMV) vector, or a rhesus CMV (RhCMV) vector.

Also disclosed herein are CMV vectors comprising all of the above modifications and further comprising a nucleic acid sequence that serves as a miRNA response element (MRE) that silences expression in the presence of a miRNA expressed by endothelial cells. Examples of such miRNAs expressed by endothelial cells include miR-126-3p, miR-130a, miR-210, miR-221/222, miR-378, miR-296 and miR-328 (Wu F, Yang Z, Li G. Role of specific microRNAs for endothelial function and angiogenesis. *Biochemical and biophysical research communications.* 2009; 386(4):549. doi:10.1016/j.bbrc.2009.06.075.); incorporated by reference herein). The MRE is operably linked to a CMV gene that is essential or augmenting for CMV growth in vivo. Examples of such genes include IE2 and UL79, or orthologs thereof. One, two, three or more CMV genes may each be operably linked to one, two, three or more MREs in the vector.

In some embodiments, the MRE may be any miRNA recognition element that silences expression in the presence of a miRNA expressed by endothelial cells. In some embodiments, an MRE of the vector silences expression in the presence of one or more of miR-126-3p, miR-130a, miR-210, miR-221/222, miR-378, miR-296, and miR-328. In some embodiments, an MRE of the vector silences expression in the presence of miR-126-3p (SEQ ID NO: 1). In some embodiments, an MRE of the vector comprises the sequence of SEQ ID NO: 2.

In some embodiments, the CMV vectors disclosed herein comprise a first MRE that silences expression in the presence of a microRNA that is expressed by a cell of endothelial lineage and a second MRE that silences expression in the presence of a microRNA that is expressed by a cell of myeloid lineage. In some embodiments, the first MRE silences expression in the presence of one or more of miR-126-3p, miR-130a, miR-210, miR-221/222, miR-378, and miR-296, and miR-328. In some embodiments, the first MRE silences expression in the presence of miR-126-3p (SEQ ID NO: 1). In some embodiments, the first MRE of the vector comprises the sequence of SEQ ID NO: 2. In some embodiments, the second MRE silences expression in the presence of one or more of miR-142-3p, miR-223, miR-27a, miR-652, miR-155, miR146a, miR-132, miR-21, and miR-125. In some embodiments, the second MRE silences expression in the presence of miR-142-3p (SEQ ID NO: 3). In some embodiments, the second MRE of the vector comprises the sequence of SEQ ID NO: 4. CMV vectors comprising MREs that silence expression in the presence of miR-142-3p are disclosed, e.g., in WO 2017/087921, which is incorporate by reference herein in its entirety.

Such MREs may be the exact complement of a miRNA. Alternatively, other sequences may be used as MREs for a given miRNA. For example, MREs may be predicted from sequences. In one example, the miRNA may be searched on the website microRNA.org. In turn, a list of mRNA targets of the miRNA will be listed. For example, microRNA.org, last accessed 6 Oct. 2015, will list putative mRNA targets of miR-142-3p. For each listed target on the page, 'alignment details' may be accessed and putative MREs accessed. In some embodiments, an MRE of the vector silences expression in the presence of one or more of miR-126-3p, miR-130a, miR-210, miR-221/222, miR-378, miR-296, and miR-328. In some embodiments, an MRE of the vector silences expression in the presence of miR-126-3p (SEQ ID NO: 1). In further embodiments, an MRE of the vector may silence expression in the presence of miR-142-3p (SEQ ID NO: 3). In some embodiments, an MRE of the vector has the nucleotide sequence of SEQ ID NO: 2. In further embodiments, an MRE of the vector has the nucleotide sequence of SEQ ID NO: 4.

One of skill in the art may select a validated, putative, or mutated MRE sequence from the literature that would be predicted to induce silencing in the presence of a miRNA expressed in an endothelial cell or a myeloid cell such as a macrophage. One example involves the above-referenced website. The person of skill in the art may then obtain an expression construct whereby a reporter gene (such as a fluorescent protein, enzyme or other reporter gene) has expression driven by a promoter such as a constitutively active promoter or cell-specific promoter. The MRE sequence may then be introduced into the expression construct. The expression construct may be transfected into an appropriate cell, and the cell transfected with the miRNA of interest. A lack of expression of the reporter gene indicates that the MRE silences gene expression in the presence of the miRNA.

Pathogen specific antigens can be derived from any human or animal pathogen. The pathogen may be a viral pathogen and the antigen may be a protein derived from the viral pathogen. Viruses include, but are not limited to Adenovirus, coxsackievirus, hepatitis A virus, poliovirus, rhinovirus, Herpes simplex type 1, Herpes simplex type 2, Varicella-zoster virus, Epstein-Barr virus, Kaposi's sarcoma herpesvirus, Human cytomegalovirus, Human herpesvirus, type 8, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus and Parvovirus B19.

The pathogen may be a bacterial pathogen and the antigen may be a protein derived from the bacterial pathogen. The pathogenic bacteria include, but are not limited to, *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholera* and *Yersinia pestis.*

The pathogen may be a parasite and the antigen may be a protein derived from the parasite pathogen. The parasite may be a protozoan organism or a protozoan organism causing a disease such as, but not limited to, Acanthamoeba, Babesiosis, Balantidiasis, Blastocystosis, Coccidia, Dientamoebiasis, Amoebiasis, Giardia, Isosporiasis, Leishmaniasis, Primary amoebic meningoencephalitis (PAM), Malaria, Rhinosporidiosis, Toxoplasmosis—Parasitic pneumonia, Trichomoniasis, Sleeping sickness and Chagas disease. The parasite may be a helminth organism or worm or a disease caused by a helminth organism such as, but not limited to, Ancylostomiasis/Hookworm, Anisakiasis, Roundworm—Parasitic pneumonia, Roundworm—Baylisascariasis, Tapeworm—Tapeworm infection, Clonorchiasis, *Dioctophyme renalis* infection, Diphyllobothriasis—tapeworm, Guinea worm—Dracunculiasis, Echinococcosis—tapeworm, Pinworm—Enterobiasis, Liver fluke—Fasciolosis, Fasciolopsiasis—intestinal fluke, Gnathostomiasis, Hymenolepiasis, *Loa loa* filariasis, Calabar swellings, Mansonelliasis, Filariasis, Metagonimiasis—intestinal fluke, River blindness, Chinese Liver Fluke, Paragonimiasis, Lung Fluke, Schistosomiasis—bilharzia, bilharziosis or snail fever (all types), intestinal schistosomiasis, urinary schistosomiasis, Schistosomiasis by *Schistosoma japonicum*, Asian intestinal schistosomiasis, Sparganosis, Strongyloidiasis—Parasitic pneumonia, Beef tapeworm, Pork tapeworm, Toxocariasis, Trichinosis, Swimmer's itch, Whipworm and Elephantiasis Lymphatic filariasis. The parasite may be an organism or disease caused by an organism such as, but not limited to, parasitic worm, Halzoun Syndrome, Myiasis, Chigoe flea, Human Botfly and Candiru. The parasite may be an ectoparasite or disease caused by an ectoparasite such as, but not limited to, Bedbug, Head louse—Pediculosis, Body louse—Pediculosis, Crab louse—Pediculosis, Demodex—Demodicosis, Scabies, Screwworm and Cochliomyia.

The antigen may be a protein derived from a cancer. As described herein, cancers include leukemia, lymphoma, sarcoma and those derived from solid tumors. The cancers, include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenstrim; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sezary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrom macroglobulinemia and Wilms tumor (kidney cancer.)

The vector does not express an active UL128, UL130, U146, UL147 protein due to the presence of a mutation in the nucleic acid sequence encoding UL128, UL130, UL146, or UL147 or homologs thereof or orthologs thereof (homologous genes of CMVs that infect other species). The mutation may be any mutation that results in a lack of expression of active proteins. Such mutations may include point mutations, frameshift mutations, deletions of less than all of the sequence that encodes the protein (truncation mutations), or deletions of all of the nucleic acid sequence that encodes the protein, or any other mutations.

In further examples, the vector does not express an active UL128, UL130, UL146 or UL147 protein due to the presence of a nucleic acid sequence in the vector that comprises an antisense or RNAi sequence (siRNA or miRNA) that inhibits the expression of the UL128, UL130, or UL146, or UL147 protein. Mutations and/or antisense and/or RNAi may be used in any combination to generate a CMV vector lacking active UL128, UL130, UL146 or UL147.

The CMV vector may comprise additional inactivating mutations known in the art to provide different immune responses, such as an inactivating US11 mutation or an inactivating UL82 (pp71) mutation, or any other inactivating mutation. The CMV vector may also comprise at least one inactivating mutations in one or more viral genes encoding viral proteins known in the art to be essential or augmenting for viral dissemination (i.e., spread from cell to cell) in vivo. Such inactivating mutations may result from point mutations, frameshift mutations, truncation mutations, or a deletion of all of the nucleic acid sequence encoding the viral protein. Inactivating mutations include any mutation in a viral gene which finally leads to a reduced function or to a complete loss of function of the viral protein. In some embodiments, the CMV vector does not express an active UL82 (pp71) protein, or an ortholog thereof. In some embodiments, the CMV vector does not express an active US11 protein, or an ortholog thereof. In some embodiments, the CMV vector does not express an active UL82 (pp71) protein or an active US11 protein, or orthologs thereof.

Also disclosed herein are methods of generating MHC-E restricted CD8+ T cell responses to heterologous antigens in a subject. The methods involve administering an effective amount of a CMV vector to the subject. In one embodiment, the CMV vector is characterized by having a nucleic acid sequence that encodes at least one heterologous antigen and a nucleic acid sequence that does not express active UL128, UL130, UL146, or UL147 proteins. The CD8+ T cell response elicited by this vector is characterized by having at least 10% of the CD8+ T cells directed against epitopes presented by MHC-E. In further examples, at least 15%, at least 20%, at least 30%, at least 40%, at least 50%, at least 60%, at least 75%, at least 90%, at least 95% or at least 95% of the CD8+ T cells are restricted by MHC-E. In some embodiments, the CD8+ T cells restricted by MHC-E recognize peptides shared by at least 90% of other subjects immunized with the vector. In some embodiments, the CD8+ T cells are directed against a supertope presented by MHC-E. In some embodiments, the method may also generate CD8+ T cells restricted by Class II MHC. In some embodiments, at least 10% of the CD8+ T cells elicited by the vector are restricted by Class II MHC or an ortholog thereof. In some embodiments, at least 15%, at least 20%, at least 30%, at least 40%, at least 50%, at least 60%, or at least 75% of the CD8+ T cells elicited by the vector are restricted by Class II MHC or an ortholog thereof. In some embodiments, the CD8+ T cells restricted by Class II MHC recognize peptides shared by at least 90% of other subjects immunized with the vector. In some embodiments, the CD8+ T cells are directed against a supertope presented by Class II MHC.

In a second embodiment, the CMV vector is characterized by having a nucleic acid sequence that serves as a miRNA response element (MRE) that is operably linked to the essential CMV genes IE2, and UL79 or orthologs thereof. In some embodiments, the MRE silences expression in the presence of a microRNA that is expressed by a cell of endothelial lineage. In some embodiments, the MRE silences expression in the presence of one or more of miR-126-3p, miR-130a, miR-210, miR-221/222, miR-378, miR-296, and miR-328. In some embodiments, the MRE silences expression in the presence of miR-126-3p. The vector also contains at least one heterologous antigen and does not express active UL128, UL130, UL146, or UL147 proteins. The vector also contains an active UL40, US28 and US27. The CD8+ T cell response elicited by this vector is characterized by having at least 10% of the CD8+ T cells directed against epitopes presented by MHC-E. In further examples, at least 15%, at least 20%, at least 30%, at least 40%, at least 50%, at least 60% or at least 75% of the CD8+ T cells are restricted by MHC-E. In some embodiments, some of the CD8+ T cells restricted by MHC-E recognize peptides are shared by at least 90% of other subjects immunized with the vector.

In some embodiments, the method further comprises identifying a CD8+ T cell receptor from the CD8+ T cells elicited by the CMV vector, wherein the CD8+ T cell receptor recognizes a MHC-E/heterologous antigen-derived peptide complex. In some embodiments, the CD8+ T cell receptor is identified by RNA or DNA sequencing.

In a third embodiment, the CMV vector is characterized by having two nucleic acid sequences that serves as MREs that are operably linked to the essential CMV genes IE2, and UL79 or orthologs thereof. In some embodiments, a first MRE silences expression in the presence of a microRNA that is expressed by a cell of endothelial lineage, and a second MRE silences expression in the presence of a microRNA that is expressed by a cell of myeloid lineage. In some embodiments, the first MRE silences expression in the presence of one or more of miR-126-3p, miR-130a, miR-210, miR-221/222, miR-378, miR-296, and miR-328. In some embodiments, the first MRE silences expression in the presence of miR-126-3p. In some embodiments, the second MRE silences expression in the presence of one or more of miR-142-3p, miR-223, miR-27a, miR-652, miR-155, miR146a, miR-132, miR-21, and miR-125. In some embodiments, the second MRE silences expression in the presence of miR-142-3p. The vector also contains at least one heterologous antigen and does not express active UL128, UL130, UL146, or UL147 proteins. The vector also contains an active UL40, US28 and US27. The CD8+ T cell response elicited by this vector is characterized by having at least 50% of the CD8+ T cells directed against epitopes presented by MHC Class Ia.

In some embodiments, the method further comprises identifying a CD8+ T cell receptor from the CD8+ T cells elicited by the CMV vector, wherein the CD8+ T cell receptor recognizes a MHC Class I/heterologous antigen-derived peptide complex. In some embodiments, the CD8+ T cell receptor is identified by RNA or DNA sequencing.

Also disclosed herein is a method of generating CD8+ T cells that recognize MHC-E-peptide complexes. This method involves administering to a first subject (or animal) a CMV vector in an amount effective to generate a set of CD8+ T cells that recognize MHC-E/peptide complexes. The CMV vector comprises a first nucleic acid sequence encoding at least one heterologous antigen and does not express an active UL128 protein or ortholog thereof; an active UL130 protein or ortholog thereof; an active UL146 protein or ortholog thereof; or an active UL147 protein or ortholog thereof. In some embodiments, the CMV vector further comprises a second nucleic acid sequence comprising a MRE that silences expression in the presence of a microRNA that is expressed by a cell of endothelial lineage. The heterologous antigen may be any antigen, including a pathogen specific antigen, a tumor antigen, a tissue-specific antigen, or a host self-antigen. In some embodiments, the host self-antigen is an antigen derived from the variable region of a T cell receptor or a B cell receptor. This method further comprises: identifying a first CD8+ T cell receptor from the set of CD8+ T cells, wherein the first CD8+ T cell receptor recognizes a MHC-E/heterologous antigen-derived peptide complex. In some embodiments, the first CD8+ T cell receptor is identified by DNA or RNA sequencing. In some embodiments, this method may further comprise transfecting the one or more CD8+ T cells with an expression vector, wherein the expression vector comprises a nucleic acid sequence encoding a second CD8+ T cell receptor and a promoter operably linked to the nucleic acid sequence encoding the T cell receptor, wherein the second CD8+ T cell receptor comprises CDR3α and CDR3β of the first CD8+ T cell receptor, thereby generating one or more transfected CD8+ T cells that recognize a MHC-E/heterologous antigen-derived peptide complex. The one or more CD8+ T cells for transfection with the expression vector may be isolated from the first subject or a second subject. In some embodiments, this method may further comprise administering the one or more transfected T cells to the first or second subject to treat a disease, such as cancer, a pathogenic infection, or an autoimmune disease or disorder. In some embodiments, this method may further comprise administering the one or more transfected T cells to the first or second subject to induce an autoimmune response to a tissue-specific antigen or a host self-antigen.

Also disclosed is a transfected CD8+ T cell that recognizes MHC-E-peptide complexes prepared by a process comprising the steps of: (1) administering to a first subject a CMV vector in an amount effective to generate a set of CD8+ T cells that recognize MHC-E/peptide complexes, (2) identifying a first CD8+ T cell receptor from the set of CD8+ T cells, wherein the first CD8+ T cell receptor recognizes a MHC-E/heterologous antigen-derived peptide complex; (3) isolating one or more CD8+ T cells from the first subject or a second subject; and (4) transfecting the one or more CD8+ T cells isolated from the first or second subject with an expression vector, thereby creating a transfected T cell that recognizes MHC-E-peptide complexes. The CMV vector comprises a first nucleic acid sequence encoding at least one heterologous antigen and does not express an active UL128 protein or ortholog thereof; an active UL130 protein or ortholog thereof; an active UL146 protein or ortholog thereof; or an active UL147 protein or ortholog thereof. In some embodiments, the CMV vector further comprises a second nucleic acid sequence comprising a MRE that silences expression in the presence of a microRNA that is expressed by a cell of endothelial lineage. The expression vector comprises a nucleic acid sequence encoding a second CD8+ T cell receptor and a promoter operably linked to the nucleic acid sequence encoding the second CD8+ T cell receptor, wherein the second CD8+ T cell receptor comprises CDR3α and CDR3β of the first CD8+ T cell receptor. The heterologous antigen may be any antigen, including a pathogen-specific antigen, tissue-specific antigen, a host self-antigen, or a tumor antigen. In some embodiments, the first CD8+ T cell receptor is identified by RNA or DNA sequencing. Also disclosed herein are methods of treating a disease, such as cancer, a pathogenic infection, or an autoimmune disease or disorder, the method comprising administering the transfected T cell that recognizes MHC-E-peptide complexes to the first or second subject. Also disclosed herein are methods of inducing an autoimmune response to a host self-antigen or tissue-specific antigen, the method comprising administering the transfected T cell that recognizes MHC-E-peptide complexes to the first or second subject.

In further examples, the methods involve administering an effective amount of a second CMV vector, the second CMV vector comprising a nucleic acid sequence that encodes a second heterologous antigen to the subject. This second vector may be any CMV vector, including a CMV vector with an active UL128 or UL130 proteins and/or an active UL146 or 147 proteins. The second CMV vector may comprise a second heterologous antigen. The second heterologous antigen may be any heterologous antigen, including a heterologous antigen identical to the heterologous antigen in the first CMV vector. The second CMV vector may be administered at any time relative to the administration of the first CMV vector including before, concurrently with, or after the administration of the first CMV vector. This includes administration of the second vector any number of months, days, hours, minutes or seconds before or after the first vector.

Human or animal CMV vectors, when used as expression vectors, are innately non-pathogenic in the selected subjects such as humans. In some embodiments, the CMV vectors have been modified to render them non-pathogenic (incapable of host-to-host spread) in the selected subjects.

A heterologous antigen may be any protein or fragment thereof that is not derived from CMV, including cancer antigens, pathogen specific antigens, model antigens (such as lysozyme KLH, or ovalbumin), tissue-specific antigens, host self-antigens, or any other antigen.

Pathogen-specific antigens may be derived from any human or animal pathogen. The pathogen may be a viral pathogen, a bacterial pathogen, or a parasite, and the antigen may be a protein derived from the viral pathogen, bacterial pathogen, or parasite. The parasite may be an organism or disease caused by an organism. For example, the parasite may be a protozoan organism, a protozoan organism causing a disease, a helminth organism or worm, a disease caused by a helminth organism, an ectoparasite, or a disease caused by an ectoparasite.

The antigen may be a protein derived from cancer. In certain embodiments, the cancer is a leukemia or lymphoma. In certain embodiments, the cancer derives from a solid tumor. In certain embodiments, the cancers include acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma, and germ cell tumors.

The antigen may be a host self-antigen. Host self-antigens include, but are not limited to, antigens derived from the variable region of a T cell receptor or from the variable region of a B cell receptor. The antigen may be a tissue-specific antigen. Tissue-specific antigens include, but are not limited to, sperm antigens or an egg antigens.

The CMV vectors disclosed herein may be used as an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response can, but need not be, protective. An immunogenic composition containing the recombinant CMV virus or vector (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms may be protective compositions).

The CMV vectors disclosed herein may be used in methods of inducing an immunological response in a subject comprising administering to the subject an immunogenic, immunological or vaccine composition comprising the recombinant CMV virus or vector and a pharmaceutically acceptable carrier or diluent. For purposes of this specification, the term "subject" includes all animals, including non-human primates and humans, while "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The CMV vectors disclosed herein may be used in therapeutic compositions containing the recombinant CMV virus or vector and a pharmaceutically acceptable carrier or diluent. The CMV vectors disclosed herein may be prepared by inserting DNA comprising a sequence that encodes the heterologous antigen into an essential or non-essential region of the CMV genome. The method may further comprise deleting one or more regions from the CMV genome. The method may comprise in vivo recombination. Thus, the method may comprise transfecting a cell with CMV DNA in a cell-compatible medium in the presence of donor DNA comprising the heterologous DNA flanked by DNA sequences homologous with portions of the CMV genome, whereby the heterologous DNA is introduced into the genome of the CMV, and optionally then recovering CMV modified by the in vivo recombination. The method may also comprise cleaving CMV DNA to obtain cleaved CMV DNA, ligating the heterologous DNA to the cleaved CMV DNA to obtain hybrid CMV-heterologous DNA, transfecting a cell with the hybrid CMV-heterologous DNA, and optionally then recovering CMV modified by the presence of the heterologous DNA. Since in vivo recombination is comprehended, the method accordingly also provides a plasmid comprising donor DNA not naturally occurring in CMV encoding a polypeptide foreign to CMV, the donor DNA is within a segment of CMV DNA that would otherwise be co-linear with an essential or non-essential region of the CMV genome such that DNA from an essential or nonessential region of CMV is flanking the donor DNA. The heterologous DNA may be inserted into CMV to generate the recombinant CMV in any orientation that yields stable integration of that DNA, and expression thereof, when desired.

The DNA encoding the heterologous antigen in the recombinant CMV vector may also include a promoter. The promoter may be from any source such as a herpes virus, including an endogenous cytomegalovirus (CMV) promoter, such as a human CMV (HCMV), rhesus macaque CMV (RhCMV), murine, or other CMV promoter. The promoter may also be a non-viral promoter such as the EF1α promoter. The promoter may be a truncated transcriptionally active promoter which comprises a region transactivated with a transactivating protein provided by the virus and the minimal promoter region of the full-length promoter from which the truncated transcriptionally active promoter is derived. The promoter may be composed of an association of DNA sequences corresponding to the minimal promoter and upstream regulatory sequences. A minimal promoter is composed of the CAP site plus TATA box (minimum sequences for basic level of transcription; unregulated level of transcription); "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter may be derived from a herpesvirus such as MCMV or HCMV, e.g., HCMV-IE or MCMV-IE. There may be up to a 40% and even up to a 90% reduction in size, from a full-length promoter, based upon base pairs. The promoter may also be a modified non-viral promoter. As to HCMV promoters, reference is made to U.S. Pat. Nos. 5,168,062 and 5,385,839. As to transfecting cells with plasmid DNA for expression therefrom, reference is made to Felgner et al. (1994), *J. Biol. Chem.* 269, 2550-2561. And, as to direct injection of plasmid DNA as a simple and effective method of vaccination against a variety of infectious diseases reference is made to *Science,* 259:1745-49, 1993. It is therefore within the scope of this disclosure that the vector may be used by the direct injection of vector DNA.

Also disclosed is an expression cassette that may be inserted into a recombinant virus or plasmid comprising the truncated transcriptionally active promoter. The expression cassette may further include a functional truncated polyadenylation signal; for instance an SV40 polyadenylation signal which is truncated, yet functional. Considering that nature provided a larger signal, it is indeed surprising that a truncated polyadenylation signal is functional. A truncated polyadenylation signal addresses the insert size limit problems of recombinant viruses such as CMV. The expression cassette may also include heterologous DNA with respect to the virus or system into which it is inserted; and that DNA may be heterologous DNA as described herein.

As to antigens for use in vaccine or immunological compositions, see also *Stedman's Medical Dictionary* (24th edition, 1982, e.g., definition of vaccine (for a list of antigens used in vaccine formulations); such antigens or epitopes of interest from those antigens may be used. As to heterologous antigens, one skilled in the art may select a heterologous antigen and the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

One method to determine T epitopes of an antigen involves epitope mapping. Overlapping peptides of the heterologous antigen are generated by oligo-peptide synthesis. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules.

An immune response to a heterologous antigen is generated, in general, as follows: T cells recognize proteins only when the protein has been cleaved into smaller peptides and is presented in a complex called the "major histocompatibility complex (MHC)" located on another cell's surface. There are two classes of MHC complexes—class I and class II, and each class is made up of many different alleles. Different species, and individual subjects have different types of MHC complex alleles; they are said to have a different MHC type. One type of MHC class I molecule is called MHC-E (HLA-E in humans, Mamu-E in RM, Qa-1b in mice).

It is noted that the DNA comprising the sequence encoding the heterologous antigen may itself include a promoter for driving expression in the CMV vector or the DNA may be limited to the coding DNA of the heterologous antigen. This construct may be placed in such an orientation relative to an endogenous CMV promoter that it is operably linked to the promoter and is thereby expressed. Further, multiple copies of DNA encoding the heterologous antigen or use of a strong or early promoter or early and late promoter, or any combination thereof, may be done so as to amplify or increase expression. Thus, the DNA encoding the heterologous antigen may be suitably positioned with respect to a CMV-endogenous promoter, or those promoters may be translocated to be inserted at another location together with the DNA encoding the heterologous antigen. Nucleic acids encoding more than one heterologous antigen may be packaged in the CMV vector.

Further disclosed are pharmaceutical and other compositions containing the disclosed CMV vectors. Such pharmaceutical and other compositions may be formulated so as to be used in any administration procedure known in the art. Such pharmaceutical compositions may be via a parenteral route (intradermal, intramuscular, subcutaneous, intravenous, or others). The administration may also be via a mucosal route, e.g., oral, nasal, genital, etc.

The disclosed pharmaceutical compositions may be prepared in accordance with standard techniques well known to those skilled in the pharmaceutical arts. Such compositions may be administered in dosages and by techniques well known to those skilled in the medical arts taking into consideration such factors as the breed or species, age, sex, weight, and condition of the particular patient, and the route of administration. The compositions may be administered alone, or may be co-administered or sequentially administered with other CMV vectors or with other immunological, antigenic or vaccine or therapeutic compositions. Such other compositions may include purified native antigens or epitopes or antigens or epitopes from the expression by a recombinant CMV or another vector system; and are administered taking into account the aforementioned factors.

Examples of compositions include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically may contain an adjuvant and an amount of the CMV vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al., *J. Immunol.* 147:410-415 (1991), encapsulation of the protein within a proteoliposome as described by Miller et al., *J. Exp. Med.* 176:1739-1744 (1992), and encapsulation of the protein in lipid vesicles such as Novasome lipid vesicles (Micro Vescular Systems, Inc., Nashua, N.H.) may also be used.

The composition may be packaged in a single dosage form for immunization by parenteral (e.g., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product may range from a few to a few hundred micrograms, e.g., 5 to 500 μg. The CMV vector may be administered in any suitable amount to achieve expression at these dosage levels. In nonlimiting examples: CMV vectors may be administered in an amount of at least $10^2$ pfu; thus, CMV vectors may be administered in at least this amount; or in a range from about $10^2$ pfu to about $10^7$ pfu. Other suitable carriers or diluents may be water or a buffered saline, with or without a preservative. The CMV vector may be lyophilized for resuspension at the time of administration or may be in solution. "About" may mean within 1%, 5%, 10% or 20% of a defined value.

It should be understood that the proteins and the nucleic acids encoding them of the present disclosure may differ from the exact sequences illustrated and described herein. Thus, the disclosure contemplates deletions, additions, truncations, and substitutions to the sequences shown, so long as the sequences function in accordance with the methods of the disclosure. In this regard, substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the proteins described but possessing minor amino acid substitutions that do not substantially affect the immunogenicity of the protein are, therefore, within the scope of the disclosure.

The nucleotide sequences of the present disclosure may be codon optimized, for example the codons may be optimized for use in human cells. For example, any viral or bacterial sequence may be so altered. Many viruses, including HIV and other lentiviruses, use a large number of rare codons and, by altering these codons to correspond to codons commonly used in the desired subject, enhanced expression of the heterologous antigen may be achieved as described in Andre et al., *J. Virol.* 72:1497-1503, 1998.

Nucleotide sequences encoding functionally and/or antigenically equivalent variants and derivatives of the CMV vectors and the glycoproteins included therein are contemplated. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

Sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, *Proc. Natl. Acad. Sci. USA* 1990; 87: 2264-2268, modified as in Karlin & Altschul, *Proc. Natl. Acad. Sci. USA* 1993; 90: 5873-5877.

Another example of a mathematical algorithm used for comparison of sequences is the algorithm of Myers & Miller, *CABIOS* 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, *Proc. Natl. Acad. Sci. USA* 1988; 85: 2444-2448.

Advantageous for use according to the present disclosure is the WU-BLAST (Washington University BLAST) version 2.0 software. WU-BLAST version 2.0 executable programs for several UNIX platforms may be downloaded. This program is based on WU-BLAST version 1.4, which in turn is based on the public domain NCBI-BLAST version 1.4 (Altschul & Gish, 1996, Local alignment statistics, Doolittle ed., *Methods in Enzymology* 266: 460-480; Altschul et al., *Journal of Molecular Biology* 1990; 215: 403-410; Gish & States, 1993; *Nature Genetics* 3: 266-272; Karlin & Altschul, 1993; *Proc. Natl. Acad. Sci. USA* 90: 5873-5877; all of which are incorporated by reference herein).

The various recombinant nucleotide sequences and antibodies and/or antigens of the disclosure are made using standard recombinant DNA and cloning techniques. Such techniques are well known to those of skill in the art. See for example, "*Molecular Cloning: A Laboratory Manual*", second edition (Sambrook et al. 1989).

The nucleotide sequences of the present disclosure may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the viruses of the present disclosure may be used in accordance with the present disclosure. In certain embodiments, the disclosed viruses may be used in vitro (such as using cell-free expression systems) and/or in cultured cells grown in vitro in order to produce the encoded heterologous antigen (e.g., pathogen-specific antigens, HIV antigens, tumor antigens, and antibodies) which may then be used for various applications such as in the production of proteinaceous vaccines. For such applications, any vector that allows expression of the virus in vitro and/or in cultured cells may be used.

For the disclosed heterologous antigens to be expressed, the protein coding sequence of the heterologous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the disclosure lead to the expression of the encoded protein. The expression of the transgenes of the present disclosure may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the disclosure. For example, suitable promoters and/or enhancers may be selected from the Eukaryotic Promoter Database (EPDB).

The disclosure relates to a recombinant viral vector expressing a heterologous protein antigen. In some examples, the antigen is an HIV antigen. Advantageously, the HIV antigens include, but are not limited to, the HIV antigens discussed in U.S. Pub. Nos. 2008/0199493 A1 and 2013/0136768 A1, both of which are incorporated by reference herein. HIV, nucleic acid or immunogenic fragments thereof, may be utilized as an HIV protein antigen. For example, the HIV nucleotides discussed in U.S. Pub. Nos. 2008/0199493 A1 and 2013/0136768 A1 may be used. Any antigen recognized by an HIV antibody may be used as an HIV protein antigen. The protein antigen may also be an SIV antigen. For example, the SIV antigens discussed in U.S. Pub. Nos. 2008/0199493 A1 and 2013/0136768 A1 may be used.

The vectors used in accordance with the present disclosure may contain a suitable gene regulatory region, such as a promoter or enhancer, such that the antigens of the disclosure may be expressed.

Expressing antigens of the disclosure in vivo in a subject, for example in order to generate an immune response against an HIV-1 antigen and/or protective immunity against HIV-1, expression vectors that are suitable for expression on that subject, and that are safe for use in vivo, should be chosen. In some examples, it may be desired to express the antibodies and/or antigens in a laboratory animal, such as for pre-clinical testing of the HIV-1 immunogenic compositions and vaccines of the disclosure. In other examples, one may express the antigens in human subjects, such as in clinical trials and for actual clinical use of the immunogenic compositions and vaccine of the disclosure.

The CMV vectors described herein may contain mutations that may prevent host to host spread, thereby rendering the virus unable to infect immunocompromised or other subjects that could face complications as a result of CMV infection. The CMV vectors described herein may also contain mutations that result in the presentation of immunodominant and nonimmunodominant epitopes as well as non-canonical MHC restriction. However, mutations in the CMV vectors described herein do not affect the ability of the vector to reinfect a subject that has been previously infected with CMV. Such CMV mutations are described in, for example, US Patent Publications 2013-0136768; 2010-

0142823; 2014-0141038; and PCT application publication WO 2014/138209, all of which are incorporated by reference herein.

The disclosed CMV vectors may be administered in vivo, for example where the aim is to produce an immunogenic response, including a CD8+ immune response, including an immune response characterized by a high percentage of the CD8+ T cell response being restricted by MHC-E (or a homolog or ortholog thereof). For example, in some examples it may be desired to use the disclosed CMV vectors in a laboratory animal, such as rhesus macaques for pre-clinical testing of immunogenic compositions and vaccines using RhCMV. In other examples, it will be desirable to use the disclosed CMV vectors in human subjects, such as in clinical trials and for actual clinical use of the immunogenic compositions using HCMV.

For such in vivo applications the disclosed CMV vectors are administered as a component of an immunogenic composition further comprising a pharmaceutically acceptable carrier. The immunogenic compositions of the disclosure are useful to stimulate an immune response against the heterologous antigen, including a pathogen-specific antigen and may be used as one or more components of a prophylactic or therapeutic vaccine against HIV-1 for the prevention, amelioration or treatment of AIDS. The nucleic acids and vectors of the disclosure are particularly useful for providing genetic vaccines, i.e., vaccines for delivering the nucleic acids encoding the antigens of the disclosure to a subject, such as a human, such that the antigens are then expressed in the subject to elicit an immune response.

Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present disclosure, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol. The present methods also include a variety of prime-boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the disclosure to provide priming and boosting regimens. CMV vectors may be used repeatedly while expressing different antigens derived from different pathogens.

EXAMPLES

The following examples are for illustration only. In light of this disclosure, those of skill in the art will recognize that variations of these examples and other examples of the disclosed disclosure be possible without undue experimentation.

Example 1

MHC-E Responses are Important for Protection Against SIV

Strain 68-1 RhCMV/SIV vectors provide the best protection ever observed against highly virulent SIV (Hansen, S. G. et al. Profound early control of highly pathogenic SIV by an effector memory T-cell vaccine. *Nature* 473, 523-7, (2011); Hansen, S. G. et al. Immune clearance of highly pathogenic SIV infection. *Nature* 502, 100-4, (2013); Hansen, S G. et al. Effector memory T cell responses are associated with protection of rhesus monkeys from mucosal simian immunodeficiency virus challenge. *Nature medicine* 15, 293-9, (2009) (hereafter "Hansen 2009")). In particular, Strain 68.1 elicits MHC-E and MHC-II restricted CD8+ T cells (Hansen, S. G. et al. Cytomegalovirus vectors violate CD8+ T cell epitope recognition paradigms. *Science* 340, 1237874 (2013) (hereafter "Hansen *Science* 2013"); Hansen, S. G. et al. Broadly targeted CD8(+) T cell responses restricted by major histocompatibility complex E. *Science* 351, 714-20 (2016) (hereafter "Hansen 2016")); however, the importance of such "unconventional" T cell responses in mediating protection has not previously been determined.

RhCMV 68-1 lacks homologs of HCMV UL128 and UL130, and re-insertion of UL128 and UL130 into RhCMV 68-1 (Strain 68-1.2 RhCMV/gag (UL128/UL130 repaired)) results in a complete switch from MHC-E and MHC-II to MHC-Ia (FIG. 1) (see also Hansen *Science* 2013). Furthermore, deletion of UL128 or UL130 from Strain 68-1.2 (Strain 68-1.2 RhCMV/gag (UL130 repaired) and Strain 68-1.2 RhCMV/gag (UL128 repaired)) results in a mixed phenotype: MHC-I and MHC-II, but not MHC-II supertope-specific or MHC-E-restricted CD8+ t cells (FIG. 1) (see also WO/2014/138209).

Figure 2:
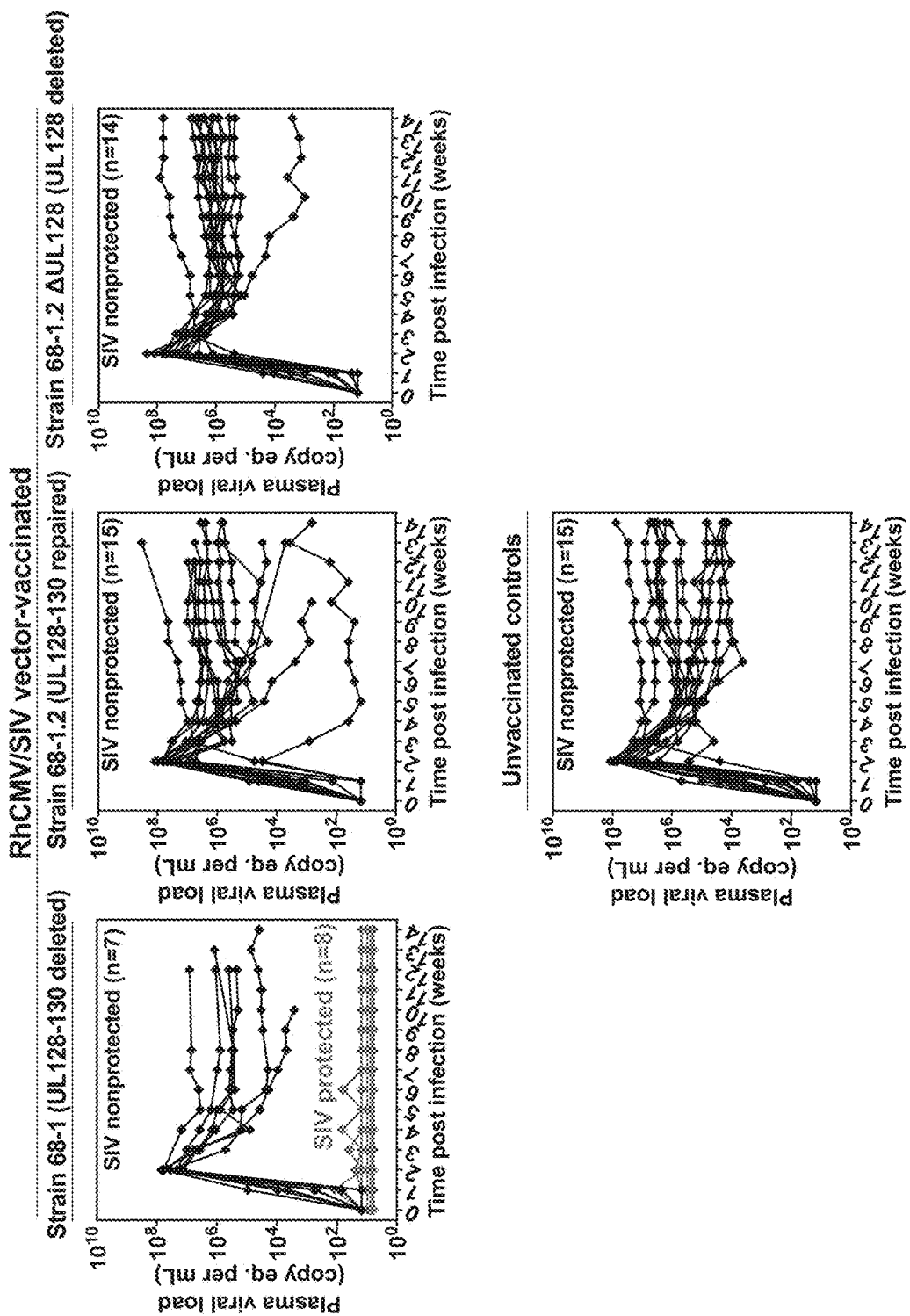
FIG. 2 shows the outcome of repeated, limiting dose, intra-rectal SIVmac239 challenge of rhesus monkeys (RM) either left unvaccinated (n=15; bottom panel) or vaccinated with: strain 68-1 RhCMV/SIV vector (n=15; top left panel); strain 68-1.2 RhCMV vector (n=15; top middle panel); or UL128-deleted (ΔUL128) 68-1.2 RhCMV vector (n=14; top right panel). All vectors expressed the same SIV Gag, Retanef (Rev/Nef/Tat fusion) and 5'-Pol inserts.

To determine whether vectors lacking the ability to elicit MHC-E-restricted CD8+ T cells would be able to protect rhesus macaques (RM) against highly virulent SIV, RM were vaccinated with one of three vectors: RhCMV 68-1 (deleted for UL128 and UL130); 68-1.2 (intact for UL128 and UL130); and 68-1.2 deleted for UL128 (intact for UL130). Each vector expressed the SIV antigens SIVgag, SIVrev-tat-nef- and SIVpol. Using the method described in Hansen 2009, the RhCMV/SIV vectors were administered subcutaneously ($5 \times 10^6$ PFU per vector) twice at t=0 and t=18 weeks, and repeated, limiting dose, intra-rectal SIV-mac239 challenge was initiated at week 91. All RM were repeatedly challenged with low dose SIVmac239 until SIV infection "take" was confirmed by the de novo development of SIV Vif-specific T cell responses, with outcome determined only on definitively SIV-infected animals. SIV Vif was not included in the vaccine, so these responses derive from SIV infection. While 8 of 15 68-1 RhCMV/SIV-vaccinated RM showed (typical) stringent SIV control, all 68-1.2 and UL128-deleted 68-1.2 RhCMV/SIV-vaccinated RM show overt progressive infection post-challenge, similar to unvaccinated controls (FIG. 2). Identical results were observed in an independent experiment comparing 68-1 vs. 68-1.2 RhCMV/SIV vaccination in female RM challenged with SIVmac239 via the intravaginal route. The magnitude and functional phenotype of the SIV-specific CD4+ and CD8+ T cell responses were comparable in all 3 vaccine groups, with the only notable difference in vector immunogencity being the nature of the epitopes targeted by the SIV-specific CD8+ T cells. Specifically, 68-1 was MHC-E- or MHC-II-restricted; (ΔUL128) 68-1.2 was MHC-Ia- or MHC-II-restricted (excluding MHC-II supertopes); and 68-1.2 was MHC-Ia-restricted only. These results strongly indicate that MHC-E restricted CD8+ T cells, and potentially MHC-II supertope-specific CD8+ T cells, are important for protection against SIV.

Example 2

Deletion of UL146 and UL147 Homologous Genes, in Addition to the Homologs of UL128 and UL130, are Required for Induction of MHC-E Responses in Cynomolgus Macaques RhCMV 68-1 is a fibroblast-adapted virus that contains multiple gene deletions, gene inversions, and single point mutations (Malouli, D. et al., Reevaluation of the Coding Potential and Proteomic Analysis of the BAC-Derived Rhesus Cytomegalovirus Strain 68-1. *J Virol* 86, 8959-73 (2012)). Additionally, wildtype RhCMV does not elicit MHC-II and MHC-E responses (Hansen *Science* 2013 and Hansen 2016). Similar to RhCMV, wildtype HCMV elicits HLA-E-restricted CD8+ T cells only in exceptional circumstances (Pietra, G. et al. HLA-E-restricted recognition of cytomegalovirus-derived peptides by human CD8+ cytolytic T lymphocytes. Proc Natl Acad Sci USA 100, 10896-10901 (2003)). It is believed that wildtype RhCMV in RM, and presumably wildtype HCMV in humans, does not elicit MHC-E responses due to the presence of UL128 and UL130. However, this does not exclude the possibility that other mutations in 68-1 are required for MHC-E responses. To address this possibility, the genetic changes required to elicit MHC-E responses were determined for a different species, cynomolgus macaques (*M. fascicularis*).

Figure 3:
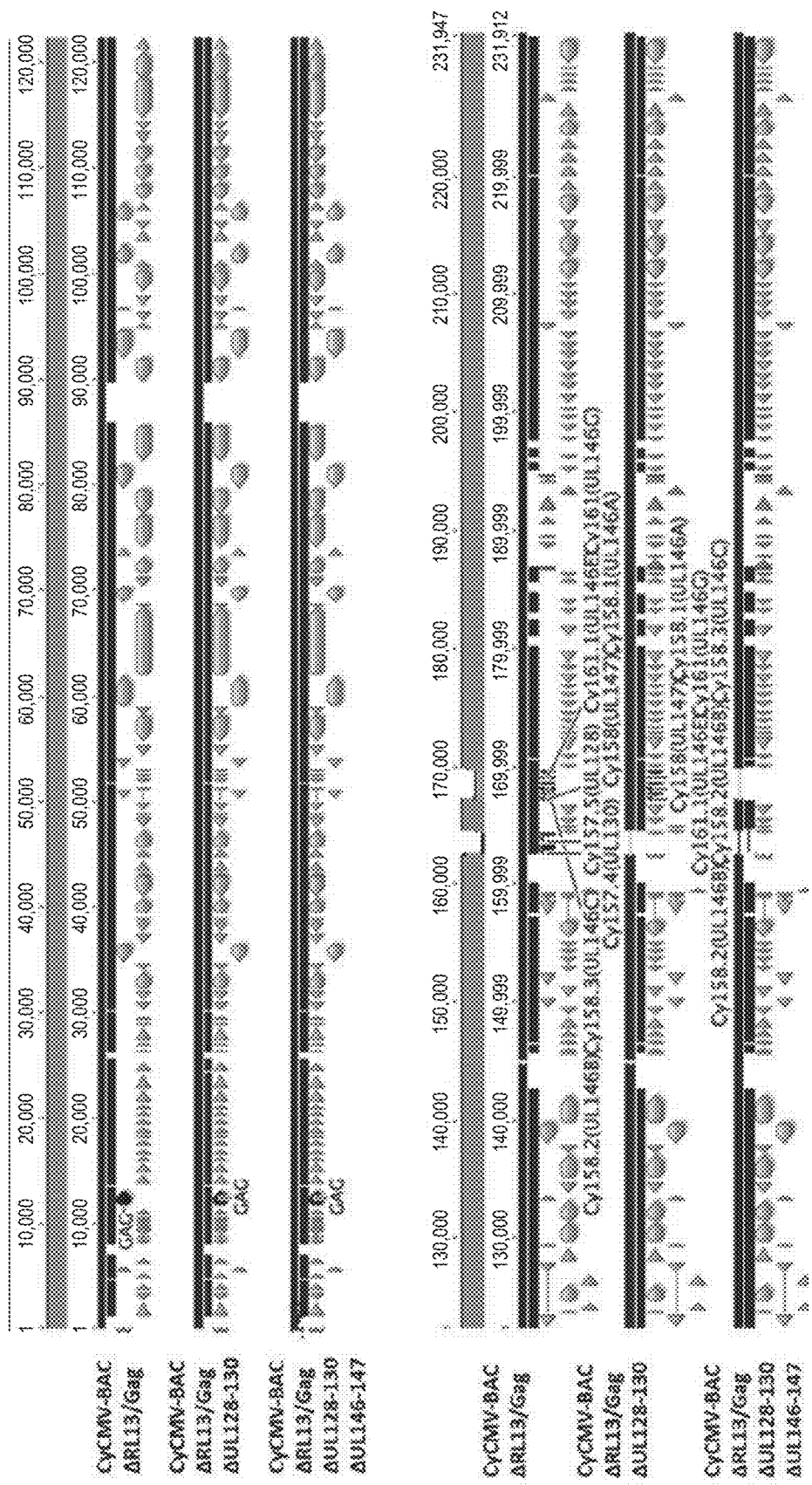
FIG. 3 shows a sequencing coverage map for CyCMV constructs. Upon Next Generation Sequencing of the CyCMV-BACs, all sequencing reads passing quality control were aligned to the de novo assembled consensus sequence of CyCMV-BAC. Shown is the ORF map of the consensus sequence for each of the constructs. The top bar indicates the percentage of nucleotide identity between a given BAC and the parental BAC sequence with dark gray being 100% identical. The SIVgag sequence replacing the Cy13.1 ORF and the CyCMV homologs of HCMV UL128, UL130, UL146 and UL147 are depicted in light gray in the top bar. The only sequence difference between the parental BAC and CyCMVΔRL13/Gag is the replacement of the CyCMV homolog of RL13 with SIVgag. CyCMVΔRL13/GagΔUL128-130 additionally lacks the homologs of UL128 and UL130, whereas the six homologs of HCMV UL146 and UL147 are additionally deleted in CyCMVΔRL13/Gag ΔUL128-130ΔUL146-147. No unwanted recombinations or spurious mutations are present in the majority sequence.

To determine whether unconventional CD8+ T cells could be elicited in Cynomolgus macaques, Cynomolgus CMV (CyCMV) was cloned as a bacterial artificial chromosome (BAC). The Cy13.1 gene, the homologue of RhCMV Rh13.1 and HCMV RL13, was replaced with SIVgag. The resulting CyCMV BAC was completely sequenced by next generation sequencing, which demonstrated the presence of all expected open reading frames (FIG. 3). To examine whether deletion of UL128-130 would be sufficient to elicit MHC-E restricted CD8+ T cells, CyCMV genes homologous to HCMV UL128 and UL130 were deleted from the precursor construct to generate CyCMV ΔRL13/SIVgag ΔUL128-130 (FIG. 4).

The immunogenicity of CyCMV ΔRL13/SIVgag ΔUL128-130 was assessed in vivo by inoculating cynomolgus macaques and monitoring the peripheral blood CD8+ memory T cell response to SIVgag peptides. PBMC from CyCMV ΔRL13/SIVgag ΔUL128-130 vector-vaccinated cynomolgus macaques were stimulated with 15 mer SIVgag peptides overlapping by four amino acids (GAG ORF) or with indicated SIVgag peptides corresponding to MHC-II or MHC-E supertopes, and flow cytometric intracellular cytokine staining (ICS) was performed. Supertope peptides are peptides that are recognized in 90% or greater of animals regardless of MHC haplotype, i.e., in the presence or absence of given MHC-I or MHC-II alleles. CD8+ T cells responding to the MHC-E or MHC-II-bound SIVgag peptides were identified via IFN-γ and TNF-α expression (FIG. 5A). The animals elicited robust, CD8 T cell responses to SIVgag when T cells were stimulated with overlapping peptides covering the entire protein (GAG ORF). However, CyCMV ΔRL13/SIVgag ΔUL128-130 did not elicit CD8+ T cell responses recognizing MHC-E supertope responses (peptides Gag69 and Gag120, described in Hansen *Science* 2013 and Hansen 2016) or MHC-II supertope responses (Gag53 and Gag73, described in Hansen *Science* 2013 and Hansen 2016) that were previously detected in all RhCMV 68-1-immunized macaques (FIG. 5B). Instead, CyCMV ΔRL13/SIVgag ΔUL128-130 induced a mixture of MHC-I and MHC-II restricted CD8+ T cell responses (FIG. 5C). However, MHC-II supertope responses were not observed. These results indicate that deletion of UL128 and UL130 from a wildtype cynomolgus CMV is insufficient for the elicitation of MHC-E restricted and MHC-II supertope-specific CD8+ T cells.

At least two different possibilities might have explained these results: a) Cynomolgus macaques are incapable of eliciting MHC-E restricted and MHC-II supertope-specific CD8+ T cells, or b) additional mutations in RhCMV 68-1 enable this virus to elicit MHC-E restricted CD8+ T cells in rhesus macaques. In addition to homologs of UL128 and UL130, RhCMV 68-1 also lacks genes with homology to HCMV UL146 and UL147 (Oxford, K. L., M. K. Eberhardt, K. W. Yang, L. Strelow, S. Kelly, S. S. Zhou, and P. A. Barry. 2008. Protein coding content of the ULb' region of wild-type rhesus cytomegalovirus. *Virology* 373:181-8; incorporated by reference herein). Wildtype RhCMV encodes six copies of these CXC-chemokine like proteins, three of which are deleted in RhCMV 68-1, and expression of the remaining 3 genes is not known. To recapitulate this feature of RhCMV 68-1, a CyCMV was generated lacking not only the homologs of UL128 and UL130, but also all six homologs of UL146 and UL147. (FIG. 4). PBMC from CyCMVΔRL13/gagΔUL128-130ΔUL146-147 vector-vaccinated cynomolgus macaques were stimulated with 15 mer SIVgag peptides overlapping by four amino acids (GAG ORF) or with indicated SIVgag peptides corresponding to MHC-II or MHC-E supertopes and flow cytometric intracellular cytokine staining (ICS) was performed. CD8+ T cells responding to the MHC-E or MHC-II-bound SIVgag peptides were identified via IFN-γ and TNF-α expression. Inoculation of cynomolgus macaques with CyCMV ΔRL13/ SIVgagΔUL128/130AUL146 elicited CD8+ T cells that recognized both MHC-E and MHC-II supertopes (FIG. 6A). In particular, Gag69 was blocked by anti-MHC-I and VL9 peptide, but not with CLIP peptide, consistent with MHC-E restriction (MHC-E is a non-polymorphic MHC-1 molecule), whereas Gag73 was blocked with CLIP peptide, but not with anti-MHC-I or VL9 peptide, consistent with MHC-II restriction (FIG. 6B). These results indicate that CyCMV ΔRL13/SIVgagΔUL128-130ΔUL146-147 elicits MHC-E and MHC-II-restricted CD8+ T cells but not polymorphic MHC-Ia-restricted CD8+ T cells (FIG. 6C).

Collectively, these data suggest that the CXC chemokine-like proteins of the UL146/147 family prevent the induction of MHC-E-restricted CD8+ T cells as well as MHC-II supertope-restricted CD8+ T cells. Accordingly, these data support the notion that MHC-E restricted and MHC-II supertope-specific CD8+ T cells may only be induced by CMV vectors that lack both UL128 and UL130, as well as all or some or all of the homologs of UL146 and UL147. The induction of MHC-E restricted CD8+ T cell responses by RhCMV has also previously been shown to require the presence of homologs of UL40 and US28. Since CyCMV also contained these genes, these results suggest that CMV vectors will only elicit MHC-E responses if they have the following genetic makeup: deletion of UL128 and UL130 or homologs; deletion of some or all of UL146 and UL147 or homologs; presence of UL40 or homologs; and presence of US28 or homologs.

Example 3

UL146 Homologs of Rhesus CMV and Human CMV Prevent Induction of MHC-E Responses in Rhesus Macaques To demonstrate that the UL146/147-homologous genes of RhCMV would similarly prevent the induction of MHC-E responses in RM even when UL128 and UL130 are deleted, a wildtype version of RhCMV was generated by restoring the original sequence of the RhCMV isolate that gave rise to the highly mutated RhCMV 68-1. The ULb'-region of the RhCMV 68-1 precursor virus was sequenced from the original isolate described by Gill et al. (Gill, R. B. et al., Coding potential of UL/b' from the initial source of rhesus cytomegalovirus Strain 68-1. *Virology* 447, 208-212). Using genetic engineering of the RhCMV 68-1 bacterial artificial chromosome (BAC), the wildtype, full-length genome (FL-RhCMV) was re-created in a series of mutagenesis steps (FIG. 7). Using the FL-RhCMV-BAC as a starting point, SIVgag was inserted into the RhCMV homolog of HCMV RL13 to generate FL-RhCMVΔRL13gag. Upon inoculation of RM, CD8+ T cell responses to SIVgag were observed, but no responses to MHC-II or MHC-E supertopes (FIG. 8A). Next, the RhCMV homologs of UL128 and UL130 were deleted to generate FL-RhCMVΔRL13gagΔUL128-130. Upon inoculation of RM, SIVgag-specific CD8+ T cell responses were similarly observed, but no responses to MHC-E or MHC-II supertopes (FIG. 8B). These observations strongly suggested that the RhCMV homologs of the HCMV UL146/147 gene family of chemokines inhibited the induction of MHC-E restricted and MHC-II supertope-specific CD8+ T cells.

Since 68-1 RhCMV lacks only 3 of the 6 homologs of HCMV UL146 and UL147, the central 3 homologs of HCMV UL146 and UL147 were deleted to determine whether this would enable UL128-130 deleted RhCMV to elicit MHC-E restricted and MHC-II supertope-specific CD8+ T cells. Surprisingly, however, FL-RhCMVΔRL13gagΔUL128-130ΔUL146(3) was unable to elicit CD8+ T cells to supertope peptides restricted by MHC-II or MHC-E (FIG. 8C). These results suggest that more than 3 of the 6 homologs need to be deleted or inactivated to elicit MHC-E restricted CD8+ T cells. Therefore, all 6 homologs of UL146 and UL147 were deleted to generate FL-RhCMVΔRL13gagΔUL128-130ΔUL146(6). RM inoculated with this vector were able to elicit CD8+ T cells recognizing MHC-II and MHC-E supertopes (FIG. 8D). These results demonstrate that deletion of all 6 homologs of UL146 and UL147 enables RhCMV lacking UL128+130 to elicit MHC-E-restricted and MHC-II supertope-specific CD8+ T cells.

Both CyCMV and RhCMV contain 6 genes homologous to the two HCMV genes UL146 and UL147. Taken together, that above data suggest that these chemokine-like genes of both cynomolgus CMV and rhesus CMV prevent the induction of MHC-E restricted CD8+ T cell responses. To determine whether this inhibitory effect was conserved in HCMV, HCMV UL146 and UL147 were inserted, alone or in combination, into FL-RhCMVΔRL13gagΔUL128-130ΔUL146(6) by BAC recombineering. Three different chimeric vectors were generated: FL-RhCMVΔRL13gagΔUL128-130hcmvUL146-UL147 (which contains both HCMV genes instead of the corresponding RhCMV homologs); FL-RhCMVΔRL13gagΔUL128-130hcmvUL146 (which contains HCMV UL146 instead of the corresponding RhCMV homologs); and FL-RhCMVΔRL13gagΔUL128-130hcmvUL147 (which contains HCMV UL147 instead of the corresponding RhCMV homologs). When RM were inoculated with these three constructs, none of the three recombinant vectors elicited CD8+ T cells recognizing MHC-II or MHC-E supertopes (FIGS. 9A-9C). These results indicate that the ability to prevent MHC-E restricted and MHC-II supertope-specific CD8+ T cells is a conserved feature in HCMV. Based on these and previous results, it is also apparent that an HCMV vector needs to have the following characteristics to elicit MHC-E restricted and MHC-II supertope-specific CD8+ T cells: a) lack of both UL128 and UL130; b) lack of both UL147 and UL147; c) presence of UL40; d) presence of either US28 or US27.

Example 4

CMV Vectors Comprising Endothelial Cell-Specific MicroRNA Recognition Elements (MRE) Elicit CD8+ T Cell Responses that are Mostly Restricted by MHC-E In order to limit the ability of the RhCMV-based vectors to replicate in endothelial lineage cells, RhCMV 68-1 was engineered to contain endothelial-specific miR-126-3p target sequences in the 3' UTRs of essential viral genes. Similar to myeloid lineage cells that exhibit tissue specific expression of miR-142-3p, endothelial cells express miR-126-3p that is cell lineage specific. It was hypothesized that insertion of miR-126-3p target sites into the 3' UTRs of two essential RhCMV genes (Rh156, an essential immediate early gene homologous to HCMV UL122 (IE2), and Rh108, an essential early gene homologous to HCMV UL79) would block viral replication in endothelial cells that highly express miR-126-3p due to inhibition of translation of mRNAs encoding these viral essential proteins.

Using galK-mediated BAC recombination, the galK selection cassette was inserted within the 3' UTR of Rh156 and then replaced with an artificial cassette containing 4 copies of the miR-126-3p binding site separated by 8 random nucleotides. A second series of recombinations was then performed, thereby inserting the galK cassette into the 3' UTR of Rh108 and replacing this with an artificial cassette as above (FIG. 10). These vectors additionally expressed a heterologous antigen derived from SIVgag by inserting this antigen (under control of the EF1α promoter) into the gene Rh211. Successful recombinations were confirmed using PCR with primers designed to regions flanking the insertion site and subsequent sequencing of the PCR products. Intact BAC DNA was subsequently electroporated into primary rhesus fibroblasts to recover virus, and viral DNA was also sequenced.

Lung fibroblasts, umbilical vein endothelial cells, and macrophages were derived from rhesus macaques. RNA was isolated from each cell type and qRT-PCR for miR-126-3p and miR-142-3p was performed on all samples. miR-126-3p and miR-142-3p copy numbers were determined from 10 ng of RNA using a standard curve. miR-126-3p miRNA is highly expressed in rhesus macaque endothelial cells, but expressed in lower levels in macrophages derived from the peripheral blood or in primary fibroblasts. In contrast, miR-142-3p is expressed highly in macrophages but not in endothelial cells or fibroblasts (FIG. 11). These data demonstrate that rhesus macaque endothelial lineage cells express much higher levels of miR-126-3p compared to rhesus fibroblasts or macrophages and provide a rationale for using this miRNA to target essential RhCMV transcripts in endothelial cells.

In cells in which miR-126-3p levels are high, viruses containing miR-126-3p binding sites in essential genes (such as Rh156 and Rh108) are severely limited for growth, as the miR-126-3p-loaded RNA Induced Silencing Complex (RISC) will bind to the 3' UTRs of Rh156 and Rh108 and block translation. To demonstrate the impact of miR-126-3p expression on viral replication, miR-126-3p or negative control mimics were transfected into rhesus fibroblasts, and viral growth of 68-1 RhCMV containing miR-126-3p target sites or a scrambled sequence of equivalent size (68-1 Rh156/Rh108 miR-126mut) was monitored. Specifically, telomerized rhesus fibroblasts were transfected with negative control miRNA or a miR-126 RNA mimic, and 24 hours after transfection, cells were infected with RhCMV 68-1 Rh156/Rh108 miR-126 or RhCMV 68-1 Rh156/Rh10 miR-126mut at an MOI of 0.01. Cells and supernatant were harvested at the indicated times and titered on rhesus fibroblasts. As shown in FIG. 12, viral growth in cells and viral release into the supernatant was severely inhibited for 68-1 RhCMV Rh156/Rh108 miR-126 but not for 68-1 RhCMV Rh156/Rh108 miR-126mut upon transfection of miR-126-3p mimics, but not upon transfection of control miRNAs.

Figure 1:
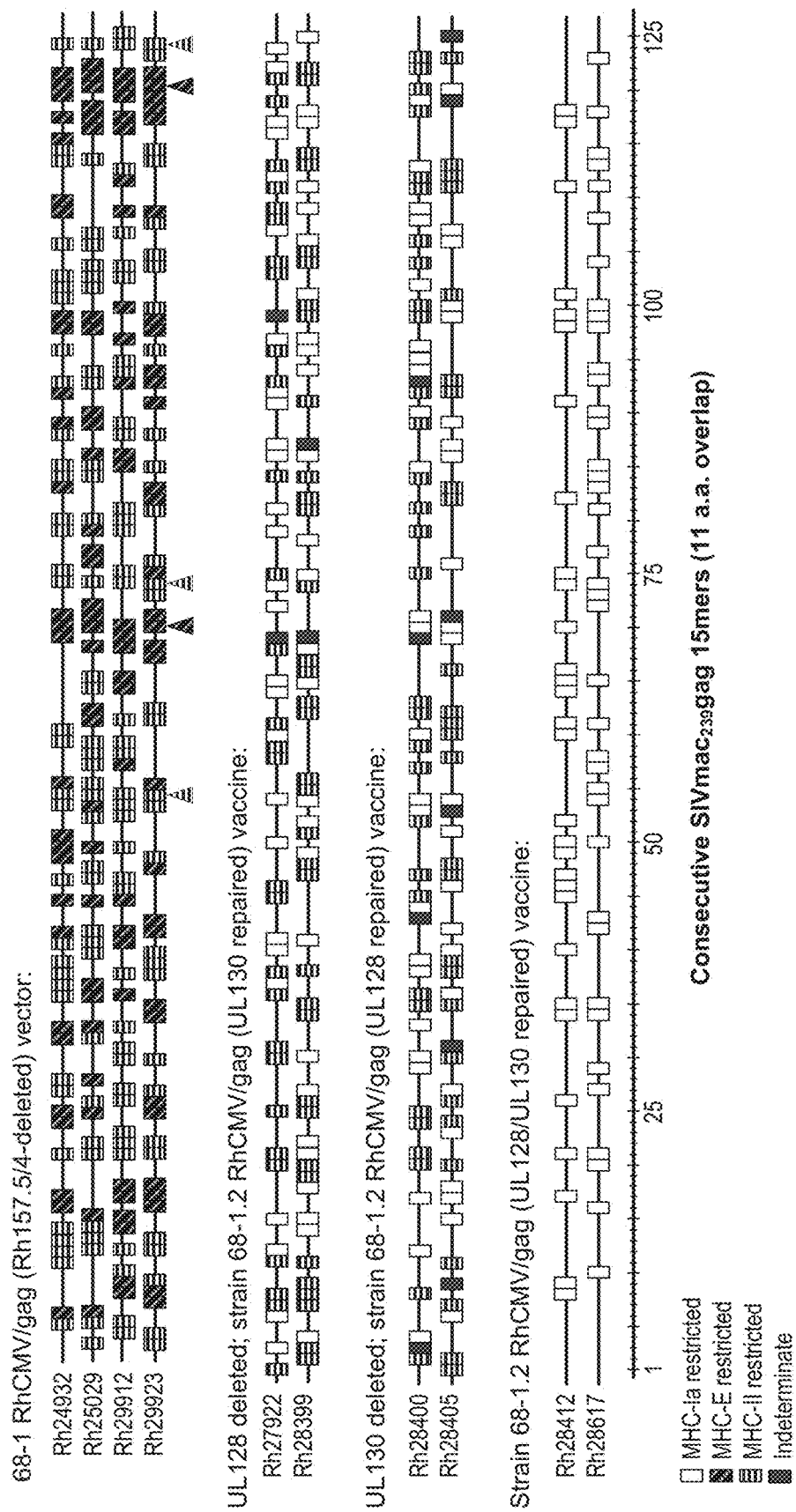
FIG. 1 shows the epitope targeting and MHC restriction of SIVgag-specific CD8+ T cells elicited by differentially programmed RhCMV/SIVgag vectors. SIVgag-specific CD8+ T cell responses elicited by the designated RhCMV vectors were epitope-mapped using flow cytometric intracellular cytokine staining (ICS) to detect recognition of 125 consecutive 15mer gag peptides (with 11 amino acid overlap). Individual peptides resulting in specific CD8+ T cell responses are indicated by a box, with the pattern of the box designating MHC restriction, as determined by blocking with the anti-pan-MHC-I mAb W6/32 (which blocks recognition of both the non-polymorphic MHC-E and polymorphic MHC-Ia molecules), the MHC-E blocking peptide VL9, and the MHC-II blocking peptide CLIP. MHC-Ia-, MHC-E-, and MHC-II-restriction was based on >90% response blocking by W6/32 alone (no fill), VL9 alone (diagonal hatch marks), and CLIP alone (horizontal hatch marks), respectively, with responses not meeting these criteria labeled indeterminate (solid fill). Arrows indicate MHC-II supertopes (horizontal hatch marks) and MHC-E supertopes MHC-E supertopes (diagonal hatch marks).

To further demonstrate that miR-126-3p inhibits viral growth in endothelial cells, miR-126-3p target sites were inserted into the 3' UTRs of IE2 and UL79 homologs in RhCMV 68-1.2, which infects endothelial cells in vitro more efficiently than RhCMV 68-1 due to an intact pentameric complex. Primary rhesus endothelial cells were infected with 68-1.2 RhCMV Rh156/Rh108 miR-126 or 68-1.2 RhCMV Rh156/Rh108 miR-126mut at an MOI of 0.01. Infected cells or supernatants were harvested at 7 days, 14 days, 21 days, and 28 days post-infection, followed by titration of virus on rhesus fibroblasts. As shown in FIG. 13, 68-1.2 RhCMV Rh156/Rh108 miR-126-3p, but not a control RhCMV 68-1.2 containing scrambled miR-126-3p target sequences (68-1.2 RhCMV Rh156/Rh108 miR-126mut), was severely limited in its ability to grow in rhesus endothelial cells.

The immunogenicity of the miR-126-restricted viruses was assessed in vivo. A rhesus macaque was inoculated with the 68-1 RhCMV Rh156/Rh108 miR-126/SIVgag vector (which lacks the homologs of UL128, UL130, UL146, and UL147, but contains functional homologs of HCMV UL40 and US28, as well as the SIVgag transgene under control of the EF1α promoter) and peripheral blood CD8+ memory T cells were isolated and analyzed for responses to overlapping SIVgag peptides via flow cytometric ICS (FIG. 15). The animal elicited robust, CD8 T cell responses to the whole proteins as shown by upregulation of CD69 and TNFα in the presence of overlapping peptides for SIVgag. This result indicated that the overall immunogenicity of the vaccine vector is not compromised by the introduction of miR-126-3p target sites. However, while the vector elicited CD8+ T cells restricted by MHC-E, it did not elicit CD8+ T cells to MHC-II restricted epitopes. To further characterize this T cell phenotype, two RM were inoculated with 68-1 RhCMV miR-126/SIVgag, and the MHC-restriction of each of 125 SIVgag peptides was determined by measuring T cell responses by ICS in the presence or absence of VL9 or CLIP peptide, which prevent MHC-E or MHC-II restricted CD8+ T cell responses, respectively. As shown in FIG. 14, all peptides recognized by CD8+ T cells obtained from 68-1 RhCMV miR-126/SIVgag-immunized RM were presented by MHC-E. These results indicate that RhCMV 68-1 elicits MHC-E and MHC-II restricted CD8+ T cells because it lacks homologs of UL128, UL130, UL146, and UL147 and expresses homologs of UL40 and US28. By inserting miR-126-3p into this backbone, MHC-II responses were eliminated.

These data demonstrate that infection of endothelial cells is required for the induction of MHC-II restricted CD8+ T cells. The insertion of miR-126-3p target sites thus results in an "MHC-E only" vector, i.e., a vector that exclusively elicits MHC-E restricted CD8+ T cells, but not T cells restricted by polymorphic MHC-I or MHC-II molecules. Since MHC-E restricted CD8+ T cells are required for protection against SIV, and persumably HIV, these data also suggest that vector efficacy might be improved by miR-126-3p insertion, which will focus the CD8+ T cell response onto protective epitopes. Accordingly, an MHC-E-optimized HCMV vector should have the following characteristics: a) lack of both UL128 and UL130; b) lack of both UL146 and UL147; c) presence of UL40; d) presence of either US28 or US27; and e) insertion of miR-126-3p target sites into the 3' UTR of essential genes, e.g., IE2 or UL79 (or any of the genes known to be essential for HCMV growth).

Example 5

CMV Vectors Comprising Both Endothelial Cell-Specific and Myeloid-Specific MicroRNA Recognition Elements (MRE) Elicit CD8+ T Cell Responses that are Mostly Restricted by MHC-Ia We previously demonstrated that RhCMV 68-1 engineered to contain myeloid-specific miR-142-3p target sequences in the 3' UTRs of essential viral genes had the exact opposite phenotype of miR-126-3p insertion complete loss of MHC-E responses, while maintaining MHC-II responses resulting in a MHC-II-only vector design (see WO/2017/087921). To determine the impact of the combined insertion of miR-142-3p and miR-126-3p we used BAC recombination to insert two copies of each miR-126-3p and miR-142-3p into the 3' UTR of Rh156 and Rh108 (FIG. 16). These vectors additionally expressed a heterologous antigen derived from SIVgag by inserting this antigen (under control of the EF1α promoter) into the gene Rh211. Successful recombinations were confirmed using PCR with primers designed to regions flanking the insertion site and subsequent sequencing of the PCR products. Intact BAC DNA was subsequently electroporated into primary rhesus fibroblasts to recover virus, and viral DNA was also sequenced.

The immunogenicity of the miR-126/mir-142-restricted viruses was assessed in vivo. A rhesus macaque was inoculated with the 68-1 RhCMV Rh156/Rh108 miR-126 miR-142/SIVgag vector (which lacks the homologs of UL128, UL130, UL146, and UL147, but contains functional homologs of HCMV UL40 and US28, as well as the SIVgag transgene under control of the EF1α promoter) and peripheral blood CD8+ memory T cells were isolated and analyzed for responses to SIVgag peptides via flow cytometric ICS (FIG. 17). The animal elicited robust, CD8 T cell responses to the whole SIVgag protein as measured in ICS using overlapping peptides. However, the vector did elicit CD8+ T cells recognizing either MHC-II or MHC-E restricted supertope peptides. To further characterize this T cell phenotype, the MHC-restriction of each of 125 SIVgag peptides was determined by measuring T cell responses by ICS in the presence or absence of pan-MHC-I (blocks both MHC-Ia and MHC-E), VL9 peptide (blocks MH-E) or CLIP peptide (blocks MHC-II). As shown in FIG. 17, all peptides recognized by CD8+ T cells obtained from 68-1 RhCMV miR-126miR-142/SIVgag-immunized RM were presented by MHC-Ia. These results indicate that a vector that lacks UL128, UL130, UL146, and UL147 or homologs thereof and expresses homologs of UL40 and US28 can be reprogrammed to elicit MHC-Ia restricted CD8+ T cells by inserting both miR-126-3p and miR-142-3p.

Table 1 summarizes the results from the above Examples. Wildtype CMV that is intact for all genes and is not restricted by cell type-specific miRs elicits conventional, MHC-I restricted CD8+ T cells. Deletion of UL128 and UL130 (either alone or in combination) results in vectors that elicit a mixture of MHC-I and (non-supertope) MHC-II restricted CD8+ T cell responses. Deletion of UL128 and UL130 together with homologs of UL146 or UL147 elicits T cell responses restricted by MHC-II and by MHC-E, including responses to MHC-II and MHC-E supertopes. Only vectors in which all of these genes have been deleted elicit MHC-E and MHC-II restricted CD8+ T cells. Vectors that lack the homologs of UL146 and UL147 but contain the UL128 and UL130 homologs do not elicit MHC-E or MHC-II restricted CD8+ T cells, but instead elicit conventional MHC-I restricted CD8+ T cells. By restricting viral gene expression in endothelial cells via miR-126-3p targeting, the induction of MHC-II restricted CD8+ T cells may be prevented, resulting in vectors that induce exclusively MHC-E restricted CD8+ T cells. By restricting viral gene expression in both endothelial and myeloid-lineage cells via miR-126-3p and miR-142-3p targeting, the induction of both MHC-II and MHC-E-restricted CD8+ T cells may be prevented, resulting in vectors that induce exclusively MHC-Ia restricted CD8+ T cells.

Example 6

Generation of CD8+ T Cells Specific for Peptides of Interest in the Context of MHC-E T cell receptors recognizing antigen-derived peptides of interest in the context of classical, polymorphic MHC-Ia molecules can be used to transfect autologous T cells for immunotherapy of disease, such as cancer or infectious disease. A major obstacle to this approach is the MHC-Ia diversity in the human population that limits the use of a given TCR to MHC-1a matched patients. By generating TCR recognizing antigen-derived peptides of interest (e.g., tumor antigen-derived peptides and pathogen-derived peptides) in the context of non-classical, non-polymorphic MHC-E molecules, MHC-matching becomes obsolete, and the resulting TCR can be used in all patients.

CD8+ T cells recognizing MHC-E/peptide complexes are rare in nature, and there is not currently a reliable method to generate such T cells directed against antigens of interest, such as tumor antigens, pathogen-derived antigens, tissue-specific antigens, or host self-antigens. The method described herein is based upon the finding that rhesus cytomegalovirus (RhCMV) and cynomolgus cytomegalovirus (CyCMV) vectors lacking genes homologous to HCMV UL128, UL130, UL146, and UL147 elicit MHC-E-restricted CD8+ T cells at an increased frequency. By inserting an antigen of interest into RhCMV or CyCMV deleted for UL128, UL130, UL146, and UL147, CD8+ T cells directed against individual peptides presented by MHC-E can be generated. The CMV vector may be further modified by including an MRE that silences gene expression in the presence of microRNA that is expressed by a cell of endothelial lineage, such as miR-126-3p. The MHC-E/peptide-recognizing TCRs can be identified by any of a number of methods but generally rely on sequencing the alpha and beta chains either directly by PCR from the cDNA of single cells, clonally expanded single cells, or deep sequencing pools of peptide specific CD8+ T cells. Alternatively the sequence may be derived indirectly by expanding the RNA template by first creating a whole transcriptome library for a single cell, clonally expanded single cell, or pool of peptide specific CD8+ T cells. Peptide specific variable sequences may be generated by rapid amplification

TABLE 1

Summary of genetic modifications that produce a particular MHC-restriction of a CMV vector

| Genetic Modifications of CMV Vector | | | | MHC-Restriction of Vector-Elicited CD8+ T Cells | | | | |
|---|---|---|---|---|---|---|---|---|
| Rh157.5 (UL128) | Rh157.4 (UL130) | Rh158/161 (UL146/147) | MicroRNA restriction* | MHC-Ia | MHC-II | MHC-II supertopes | MHC-E | MHC-E supertopes |
| intact | Intact | intact | None | yes | no | no | no | no |
| deleted | Intact | intact or deleted | None | yes | yes | no | no | no |
| intact | Deleted | intact or deleted | None | yes | yes | no | no | no |
| deleted | Deleted | intact | None | yes | yes | no | no | no |
| intact | Intact | deleted | None | yes | no | no | no | no |
| deleted | Deleted | deleted | None | no | yes | yes | yes** | yes** |
| deleted | Deleted | deleted | miR-126-3p | no | no | no | yes** | yes** |
| deleted | deleted | deleted | miR-142-3p | no | yes | yes | no | no |
| deleted | deleted | deleted | miR-126-3p; miR-142-3p | yes | no | no | no | no |

*Insertion of four copies of the miR target sequences into the 3' UTRs of the essential viral genes IE2 (Rh156) and UL79 (Rh108)
**MHC-E-restricted response priming also depends on intact function of Rh67 and Rh214/220 or their HCMV orthologs (UL40 and US27/28)

of cDNA ends (RACE) or switching mechanism at 5'end of RNA template (SMART) protocols performed on the mRNA. PCR anchored in flanking constant regions or similarly from whole transcriptome libraries of single peptide reactive CD8+ cells can be sequenced directly or deep sequenced for their respective TCR variable regions. Validated combinations of alpha and beta chains derived from the TCR sequence of individual or pools of peptide reactive CD8+ T-cells can further be synthesized or cloned. The resulting TCR constructs can then be transfected into T cells that can in turn be administered to patients as a therapy (e.g., cancer therapy or infectious disease therapy). Methods of cloning and transfecting TCR variable regions are also discussed in Barsov E V et al., *PLoS One* 6, e23703 (2011), which is incorporated by reference herein.

an active UL147 protein or ortholog thereof; and wherein the microRNA is miR-126-3p, miR-130a, miR-210, miR-221/222, miR-378, miR-296, or miR-328.

2. The CMV vector of claim 1, wherein the microRNA is miR-126-3p.

3. The CMV vector of claim 2, wherein the gene that is essential or augmenting for CMV growth is UL122 (IE2) or UL79.

4. The CMV vector of claim 1, wherein the at least one heterologous antigen comprises a pathogen-specific antigen, a tumor antigen, a tissue-specific antigen, or a host self-antigen.

5. The CMV vector of claim 4, wherein the host self-antigen is an antigen derived from the variable region of a

The invention claimed is:

1. A cytomegalovirus (CMV) vector comprising:
   (a) a first nucleic acid sequence that encodes at least one heterologous antigen; and
   (b) a second nucleic acid sequence comprising a first heterologous microRNA recognition element (MRE) operably linked to a CMV gene that is essential or augmenting for CMV growth, wherein the MRE is complementary to a microRNA that is expressed by a cell of endothelial lineage;
   wherein the vector does not express an active UL128 protein or ortholog thereof; does not express an active UL130 protein or ortholog thereof; does not express an active UL146 or ortholog thereof; and does not express T cell receptor (TCR) or an antigen derived from the variable region of a B cell receptor.

6. The CMV vector of claim 4, wherein the pathogen specific antigen is derived from a pathogen selected from the group consisting of: human immunodeficiency virus, simian immunodeficiency virus, herpes simplex virus type 1, herpes simplex virus type 2, hepatitis B virus, hepatitis C virus, papillomavirus, *Plasmodium* parasites, and *Mycobacterium tuberculosis*.

7. The CMV vector of claim 4, wherein the tumor antigen is related to a cancer selected from the group consisting of: acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors.

8. The CMV vector of claim 1, wherein the CMV vector does not express an active UL82 (pp71) protein, or an ortholog thereof.

9. The CMV vector of claim 1, wherein the CMV vector does not express an active US11 protein, or an ortholog thereof.

10. The CMV vector of claim 1, wherein the CMV vector does not express an active UL82 (pp71) protein or an active US11 protein, or orthologs thereof.

11. The CMV vector of claim 1, wherein the CMV vector is a human CMV vector (HCMV), a cynomolgus CMV (CyCMV) vector, or a rhesus CMV (RhCMV) vector.

12. A method of generating an immune response in a subject to at least one heterologous antigen, the method comprising:
administering to the subject the CMV vector of claim 1 in an amount effective to elicit a CD8+ T cell response to the at least one heterologous antigen.

13. The method of claim 12, wherein at least 10% of the CD8+ T cells elicited by the CMV vector are restricted by MHC-E or an ortholog thereof.

14. The method of claim 13, wherein at least 20% of the CD8+ T cells elicited by the CMV vector are restricted by MHC-E or an ortholog thereof.

15. The method of claim 12, wherein fewer than 10% of the CD8+ T cells elicited by the CMV vector are restricted by MHC-class Ia or an ortholog thereof.

16. The method of claim 12, wherein some of the CD8+ T cells restricted by MHC-E recognize peptides shared by at least 90% of other subjects immunized with the vector.

17. The method of claim 12, further comprising administering to the subject a second CMV vector comprising a nucleic acid sequence that encodes at least one heterologous antigen.

18. The method of claim 17, wherein the second CMV vector expresses one or more active proteins selected from the group consisting of: UL128, or an ortholog thereof; UL129, or an ortholog thereof; UL146, or an ortholog thereof; and UL147, or an ortholog thereof.

19. The method of claim 17, wherein the at least one heterologous antigen of the first CMV vector and the second CMV vector are the same antigen.

20. The method of claim 17, wherein the second CMV vector is administered before, concurrently with, or after the first CMV vector.

21. The method of claim 12, wherein the subject has been previously exposed to CMV.

22. The method of claim 12, wherein the subject is a human or nonhuman primate.

23. The method of claim 12, wherein administering the CMV vector comprises subcutaneous, intravenous, intramuscular, intraperitoneal, or oral administration of the CMV vector.

24. The method of claim 13, further comprising identifying a CD8+ TCR from the CD8+ T cells elicited by the CMV vector, wherein the CD8+ TCR recognizes a MHC-E/heterologous antigen-derived peptide complex.

25. The method of claim 24, wherein the CD8+ TCR is identified by DNA or RNA sequencing.

26. A cytomegalovirus (CMV) vector comprising:
(a) a first nucleic acid sequence that encodes at least one heterologous antigen;
(b) a second nucleic acid sequence comprising a first heterologous microRNA recognition element (MRE) operably linked to a CMV gene that is essential or augmenting for CMV growth, wherein the MRE is complementary to a first microRNA that is expressed by a cell of endothelial lineage; and
(c) a third nucleic acid sequence comprising a second heterologous MRE operably linked to a CMV gene that is essential or augmenting for CMV growth, wherein the second MRE is complementary to a second microRNA that is expressed by a cell of myeloid lineage;
wherein the vector does not express an active UL128 protein or ortholog thereof; does not express an active UL130 protein or ortholog thereof; does not express an active UL146 protein or ortholog thereof; and does not express an active UL147 protein or ortholog thereof; wherein the first microRNA is miR-126-3p, miR-130a, miR-210, miR-221/222, miR-378, miR-296, or miR-328: and wherein the second microRNA is miR-142-3p, miR-223, miR-27a, miR-652, miR-155, miR-146a, miR-132, miR-21, or miR-125.

27. The CMV vector of claim 26, wherein the first microRNA is miR-126-3p.

28. The CMV vector of claim 27, wherein the CMV gene that is essential or augmenting for CMV growth is UL122 (IE2) or UL79.

29. The CMV vector of claim 26, wherein the second microRNA is miR-142-3p.

30. The CMV vector of claim 26, wherein the at least one heterologous antigen comprises a pathogen-specific antigen, a tumor antigen, a tissue-specific antigen, or a host self-antigen.

31. The CMV vector of claim 30, wherein the host self-antigen is an antigen derived from the variable region of a T cell receptor (TCR) or an antigen derived from the variable region of a B cell receptor.

32. The CMV vector of claim 30, wherein the pathogen-specific antigen is derived from a pathogen selected from the group consisting of: human immunodeficiency virus, simian immunodeficiency virus, herpes simplex virus type 1, herpes simplex virus type 2, hepatitis B virus, hepatitis C virus, papillomavirus, *Plasmodium* parasites, and *Mycobacterium tuberculosis*.

33. The CMV vector of claim 30, wherein the tumor antigen is related to a cancer selected from the group consisting of: acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors.

34. The CMV vector of claim 26, wherein the CMV vector does not express an active UL82 (pp71) protein, or an ortholog thereof.

35. The CMV vector of claim 26, wherein the CMV vector does not express an active US11 protein, or an ortholog thereof.

36. The CMV vector of claim 26, wherein the CMV vector does not express an active UL82 (pp71) protein or an active US11 protein, or orthologs thereof.

37. The CMV vector of claim 26, wherein the CMV vector is a human CMV vector (HCMV), a cynomolgus CMV (CyCMV) vector, or a rhesus CMV (RhCMV) vector.

38. A method of generating an immune response in a subject to at least one heterologous antigen, the method comprising:

administering to the subject the CMV vector of claim 26, in an amount effective to elicit a CD8+ T cell response to the at least one heterologous antigen.

39. The method of claim 38, wherein at least 50% of the CD8+ T cells elicited by the CMV vector are restricted by MHC Class Ia or an ortholog thereof.

40. The method of claim 38, further comprising administering to the subject a second CMV vector comprising a nucleic acid sequence that encodes at least one heterologous antigen.

41. The method of claim 40, wherein the second CMV vector expresses one or more active proteins selected from the group consisting of: UL128, or an ortholog thereof, UL129, or an ortholog thereof, UL146, or an ortholog thereof; and UL147, or an ortholog thereof.

42. The method of claim 40, wherein the at least one heterologous antigen of the first CMV vector and the second CMV vector are the same antigen.

43. The method of claim 40, wherein the second CMV vector is administered before, concurrently with, or after the first CMV vector.

44. The method of claim 38, wherein the subject has been previously exposed to CMV.

45. The method of claim 38, wherein the subject is a human or nonhuman primate.

46. The method of claim 38, wherein administering the CMV vector comprises subcutaneous, intravenous, intramuscular, intraperitoneal, or oral administration of the CMV vector.

47. A method of generating CD8+ T cells that recognize MHC-E-peptide complexes, the method comprising:
(1) administering to a subject the CMV vector of claim 1 in an amount effective to generate a set of CD8+ T cells that recognize MHC-E/peptide complexes;
(2) identifying a first CD8+ TCR from the set of CD8+ T cells, wherein the first CD8+ TCR recognizes a MHC-E/heterologous antigen-derived peptide complex;
(3) isolating one or more CD8+ T cells from the subject; and
(4) transfecting the one or more CD8+ cells with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating one or more transfected CD8+ T cells that recognize a MHC-E/heterologous antigen-derived peptide complex.

48. A method of generating CD8+ T cells that recognize MHC-E-peptide complexes, the method comprising:
(1) administering to a first subject the CMV vector of claim 1 in an amount effective to generate a set of CD8+ T cells that recognize MHC-E/peptide complexes;
(2) identifying a first CD8+ TCR from the set of CD8+ T cells, wherein the first CD8+ TCR recognizes a MHC-E/heterologous antigen-derived peptide complex;
(3) isolating one or more CD8+ T cells from a second subject; and
(4) transfecting the one or more CD8+ T cells with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating one or more transfected CD8+ T cells that recognize a MHC-E/heterologous antigen-derived peptide complex.

49. A transfected CD8+ T cell generated by the method of claim 47.

50. A method of treating cancer, a pathogenic infection, or an autoimmune disease or disorder, the method comprising administering the CD8+ T cell of claim 49 to a subject.

51. A method of inducing an autoimmune response to a host self-antigen or tissue-specific antigen, the method comprising administering the CD8+ T cell of claim 49 to the subject.

52. A transfected CD8+ T cell generated by the method of claim 48.

53. A method of treating cancer, a pathogenic infection, or an autoimmune disease or disorder in a subject, the method comprising administering the CD8+ T cell of claim 52 to the subject.

54. A method of inducing an autoimmune response to a host self-antigen or tissue-specific antigen in a subject, the method comprising administering the CD8+ T cell of claim 52 to the subject.

55. A method of generating CD8+ T cells that recognize MHC-E-peptide complexes, the method comprising:
(1) administering to a subject the CMV vector of claim 1 in an amount effective to generate a set of CD8+ T cells that recognize MHC-E/peptide complexes, wherein the CMV vector is a human cytomegalovirus (HCMV) vector;
(2) identifying a first CD8+ TCR from the set of CD8+ T cells, wherein the first CD8+ TCR recognizes a MHC-E/heterologous antigen-derived peptide complex;
(3) isolating one or more additional CD8+ T cells from the subject; and
(4) transfecting the one or more CD8+ cells from step (3) with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating one or more transfected CD8+ T cells that recognize a MHC-E/heterologous antigen-derived peptide complex.

56. A method of generating CD8+ T cells that recognize MHC-E-peptide complexes, the method comprising:
(1) administering to a first subject the CMV vector of claim 1 in an amount effective to generate a set of CD8+ T cells that recognize MHC-E/peptide complexes, wherein the CMV vector is a HCMV vector;
(2) identifying a first CD8+ TCR from the set of CD8+ T cells, wherein the first CD8+ TCR recognizes a MHC-E/heterologous antigen-derived peptide complex;
(3) isolating one or more CD8+ T cells from a second subject; and
(4) transfecting the one or more CD8+ T cells isolated from the second subject with an expression vector, wherein the expression vector comprises a nucleic acid sequence encoding a second CD8+ TCR and a promoter operably linked to the nucleic acid sequence encoding the second CD8+ TCR, wherein the second CD8+ TCR comprises CDR3α and CDR3β of the first CD8+ TCR, thereby generating one or more transfected CD8+ T cells that recognize a MHC-E/heterologous antigen-derived peptide complex.

57. A transfected CD8+ T cell generated by the method of claim 55.

58. A method of treating cancer, a pathogenic infection, or an autoimmune disease or disorder in a subject, the method comprising administering the CD8+ T cell of claim 57 to the subject.

59. A method of inducing an autoimmune response to a host self-antigen or tissue-specific antigen in a subject, the method comprising administering the CD8+ T cell of claim 57 to the subject.

60. A transfected CD8+ T cell generated by the method of claim 56.

61. A method of treating cancer, a pathogenic infection, or an autoimmune disease or disorder in a subject, the method comprising administering the CD8+ T cell of claim 60 to the subject.

62. A method of inducing an autoimmune response to a host self-antigen or tissue-specific antigen in a subject, the method comprising administering the CD8+ T cell of claim 60 to the subject.

63. The method of claim 13, wherein at least 30% of the CD8+ T cells elicited by the CMV vector are restricted by MHC-E or an ortholog thereof.

64. The method of claim 13, wherein at least 40% of the CD8+ T cells elicited by the CMV vector are restricted by MHC-E or an ortholog thereof.

65. The method of claim 13, wherein at least 50% of the CD8+ T cells elicited by the CMV vector are restricted by MHC-E or an ortholog thereof.

66. The method of claim 13, where in at least 60% of the CD8+ T cells elicited by the CMV vector are restricted by MHC-E or an ortholog thereof.

67. The method of claim 13, wherein at least 75% of the CD8+ T cells elicited by the CMV vector are restricted by MHC-E or an ortholog thereof.

* * * * *